(12) United States Patent
Khairkhahan et al.

(10) Patent No.: US 11,419,722 B2
(45) Date of Patent: Aug. 23, 2022

(54) DEVICE, SYSTEM, AND METHOD FOR TRANSCATHETER TREATMENT OF VALVE REGURGITATION

(71) Applicant: Polares Medical Inc., Palo Alto, CA (US)

(72) Inventors: Alexander Khairkhahan, Palo Alto, CA (US); Michael D. Lesh, Mill Valley, CA (US)

(73) Assignee: Polares Medical Inc., Palo Alto, CA (US)

( * ) Notice: Subject to any disclaimer, the term of this patent is extended or adjusted under 35 U.S.C. 154(b) by 306 days.

(21) Appl. No.: 16/717,363

(22) Filed: Dec. 17, 2019

(65) Prior Publication Data
US 2020/0214841 A1 Jul. 9, 2020

Related U.S. Application Data

(63) Continuation of application No. 15/455,567, filed on Mar. 10, 2017, now Pat. No. 10,512,542, which is a
(Continued)

(51) Int. Cl.
*A61F 2/24* (2006.01)
*A61F 2/00* (2006.01)
(Continued)

(52) U.S. Cl.
CPC ........ *A61F 2/2457* (2013.01); *A61B 17/0401* (2013.01); *A61F 2/2418* (2013.01);
(Continued)

(58) Field of Classification Search
CPC ...... A61F 2/246; A61F 2/2418; A61F 2/2454; A61F 2/2466; A61F 2210/0014;
(Continued)

(56) References Cited

U.S. PATENT DOCUMENTS

| 3,491,376 A | 1/1970 | Shiley |
| 3,503,079 A | 3/1970 | Smith |

(Continued)

FOREIGN PATENT DOCUMENTS

| CN | 102256568 | 12/2002 |
| CN | 1984621 | 6/2007 |

(Continued)

OTHER PUBLICATIONS

Office Action for CA 2,877,344 dated Jul. 21, 2020.
(Continued)

*Primary Examiner* — Julian W Woo
(74) *Attorney, Agent, or Firm* — Knobbe, Martens, Olson & Bear, LLP

(57) ABSTRACT

The invention relates to a device for use in the transcatheter treatment of mitral valve regurgitation, specifically a coaptation enhancement element for implantation across the valve; a system including the coaptation enhancement element and anchors for implantation; a system including the coaptation enhancement element, catheter and driver; and a method for transcatheter implantation of a coaptation element across a heart valve.

18 Claims, 43 Drawing Sheets

Related U.S. Application Data continuation of application No. 14/542,091, filed on Nov. 14, 2014, now Pat. No. 9,592,118, which is a continuation of application No. 13/531,407, filed on Jun. 22, 2012, now Pat. No. 8,888,843, which is a continuation-in-part of application No. 13/099,532, filed on May 3, 2011, now Pat. No. 8,845,717.

(60) Provisional application No. 61/437,397, filed on Jan. 28, 2011.

(51) Int. Cl.
    *A61B 17/04*     (2006.01)
    *A61L 27/04*     (2006.01)
    *A61L 27/36*     (2006.01)
    *A61L 27/06*     (2006.01)
    *A61L 27/50*     (2006.01)
    *A61B 17/068*     (2006.01)
    *A61B 17/064*     (2006.01)
    *A61B 90/00*     (2016.01)

(52) U.S. Cl.
CPC .......... *A61F 2/2454* (2013.01); *A61F 2/2466* (2013.01); *A61L 27/042* (2013.01); *A61L 27/06* (2013.01); *A61L 27/3625* (2013.01); *A61L 27/50* (2013.01); *A61B 17/068* (2013.01); *A61B 2017/0406* (2013.01); *A61B 2017/0409* (2013.01); *A61B 2017/0414* (2013.01); *A61B 2017/0443* (2013.01); *A61B 2017/0448* (2013.01); *A61B 2017/0649* (2013.01); *A61B 2090/08021* (2016.02); *A61F 2210/0014* (2013.01); *A61F 2220/0008* (2013.01); *A61F 2400/16* (2013.01); *A61L 2430/20* (2013.01)

(58) Field of Classification Search
CPC .. A61F 2/2457; A61L 27/3625; A61L 27/042; A61B 17/0401; A61B 2090/08021; A61B 17/068; A61B 2017/0443; A61B 2017/0414; A61B 2017/0448; A61B 2017/0649; A61B 2017/0409
USPC .......... 606/151; 623/2.11, 2.3, 2.38; 600/30, 600/37; 128/831
See application file for complete search history.

(56) References Cited

U.S. PATENT DOCUMENTS

| | | |
|---|---|---|
| 3,656,185 A | 4/1972 | Carpentier |
| 3,671,979 A | 6/1972 | Moulopoulos |
| 3,874,388 A | 4/1975 | King et al. |
| 3,898,701 A | 8/1975 | La Russa |
| 3,938,197 A | 2/1976 | Milo |
| 4,007,743 A | 2/1977 | Blake |
| 4,011,601 A | 3/1977 | Clune et al. |
| 4,042,979 A | 8/1977 | Angell |
| 4,078,268 A | 3/1978 | Possis |
| 4,204,283 A | 5/1980 | Bellhouse et al. |
| 4,218,783 A | 8/1980 | Reul et al. |
| 4,261,342 A | 4/1981 | Aranguren Duo |
| 4,263,680 A | 4/1981 | Ruel et al. |
| 4,275,469 A | 6/1981 | Gabbay |
| RE31,040 E | 9/1982 | Possis |
| 4,352,211 A | 10/1982 | Parravicini |
| 4,488,318 A | 12/1984 | Kaster |
| 4,490,859 A | 1/1985 | Black et al. |
| 4,491,986 A | 1/1985 | Gabbay |
| 4,561,129 A | 12/1985 | Arpesella |
| 4,687,483 A | 8/1987 | Fisher et al. |
| 4,705,516 A | 11/1987 | Barone et al. |
| 4,759,758 A | 7/1988 | Gabbay |
| 4,790,843 A | 12/1988 | Carpentier et al. |
| 4,960,424 A | 10/1990 | Grooters |
| 4,994,077 A | 2/1991 | Dobben |
| 5,002,567 A | 3/1991 | Bona et al. |
| 5,078,737 A | 1/1992 | Bona et al. |
| 5,131,905 A | 7/1992 | Grooters |
| 5,197,980 A | 3/1993 | Gorshkov et al. |
| 5,217,484 A | 6/1993 | Marks |
| 5,258,023 A | 11/1993 | Reger |
| 5,332,402 A | 7/1994 | Teitelbaum |
| 5,344,442 A | 9/1994 | Deac |
| 5,370,662 A | 12/1994 | Stone et al. |
| 5,397,347 A | 3/1995 | Cuilleron et al. |
| 5,397,348 A | 3/1995 | Campbell et al. |
| 5,413,599 A | 5/1995 | Imachi et al. |
| 5,487,760 A | 1/1996 | Villafana |
| 5,500,015 A | 3/1996 | Deac |
| 5,522,886 A | 6/1996 | Milo |
| 5,554,186 A | 9/1996 | Guo et al. |
| 5,582,616 A | 12/1996 | Bolduc et al. |
| 5,593,435 A | 1/1997 | Carpentier et al. |
| 5,626,613 A | 5/1997 | Schmieding |
| 5,658,313 A | 8/1997 | Thal |
| 5,662,683 A | 9/1997 | Kay |
| 5,662,704 A | 9/1997 | Gross |
| 5,716,370 A | 2/1998 | Williamson, IV et al. |
| 5,733,331 A | 3/1998 | Peredo |
| 5,824,065 A | 10/1998 | Gross |
| 5,824,066 A | 10/1998 | Gross |
| 5,824,067 A | 10/1998 | Gross |
| 5,855,601 A | 1/1999 | Bessler et al. |
| 5,888,240 A | 3/1999 | Carpentier et al. |
| 5,957,949 A | 9/1999 | Leonhardt et al. |
| 6,007,577 A | 12/1999 | Vanney et al. |
| 6,024,096 A | 2/2000 | Buckberg |
| 6,042,607 A | 3/2000 | Williamson, IV et al. |
| 6,045,497 A | 4/2000 | Schweich et al. |
| 6,045,573 A | 4/2000 | Wenstrom et al. |
| 6,063,114 A | 5/2000 | Nash et al. |
| 6,066,160 A | 5/2000 | Colvin et al. |
| 6,086,612 A | 7/2000 | Jansen |
| 6,113,631 A | 9/2000 | Jansen |
| 6,162,233 A | 12/2000 | Williamson, IV et al. |
| 6,217,610 B1 | 4/2001 | Carpentier et al. |
| 6,221,104 B1 | 4/2001 | Buckberg et al. |
| 6,250,308 B1 | 6/2001 | Cox |
| 6,264,602 B1 | 7/2001 | Mortier et al. |
| 6,287,339 B1 | 9/2001 | Vazquez et al. |
| 6,296,662 B1 | 10/2001 | Caffey |
| 6,299,637 B1 | 10/2001 | Shaolian et al. |
| 6,312,447 B1 | 11/2001 | Grimes |
| 6,312,464 B1 | 11/2001 | Navia |
| 6,332,893 B1 | 12/2001 | Mortier et al. |
| 6,358,277 B1 | 3/2002 | Duran |
| 6,383,147 B1 | 5/2002 | Stobie |
| 6,391,053 B1 | 5/2002 | Brendzel et al. |
| 6,391,054 B2 | 5/2002 | Carpentier et al. |
| 6,402,679 B1 | 6/2002 | Mortier et al. |
| 6,402,780 B2 | 6/2002 | Williamson, IV et al. |
| 6,409,758 B2 | 6/2002 | Stobie et al. |
| 6,419,695 B1 | 7/2002 | Gabbay |
| 6,439,237 B1 | 8/2002 | Buckberg et al. |
| 6,450,171 B1 | 9/2002 | Buckberg et al. |
| 6,451,024 B1 | 9/2002 | Thompson et al. |
| 6,454,799 B1 | 9/2002 | Schreck |
| 6,458,153 B1 | 10/2002 | Bailey et al. |
| 6,482,228 B1 | 11/2002 | Norred |
| 6,540,782 B1 | 4/2003 | Snyders |
| 6,544,167 B2 | 4/2003 | Buckberg et al. |
| 6,565,603 B2 | 5/2003 | Cox |
| 6,569,198 B1 | 5/2003 | Wilson |
| 6,602,288 B1 | 8/2003 | Cosgrove et al. |
| 6,602,289 B1 | 8/2003 | Colvin et al. |
| 6,626,930 B1 | 9/2003 | Allen et al. |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,682,559 B2 | 1/2004 | Myers et al. |
| 6,702,852 B2 | 3/2004 | Stobie et al. |

(56) References Cited

U.S. PATENT DOCUMENTS

| | | |
|---|---|---|
| 6,719,790 B2 | 4/2004 | Brendzel et al. |
| 6,752,813 B2 | 6/2004 | Goldfarb et al. |
| 6,764,510 B2 | 7/2004 | Vidlund et al. |
| 6,780,200 B2 | 8/2004 | Jansen |
| 6,790,237 B2 | 9/2004 | Stinson |
| 6,797,002 B2 | 9/2004 | Spence et al. |
| 6,800,090 B2 | 10/2004 | Alferness et al. |
| 6,805,710 B2 | 10/2004 | Bolling et al. |
| 6,821,297 B2 | 11/2004 | Snyders |
| 6,837,247 B2 | 1/2005 | Buckberg et al. |
| 6,840,246 B2 | 1/2005 | Downing |
| 6,846,324 B2 | 1/2005 | Stobie |
| 6,869,444 B2 | 3/2005 | Gabbay |
| 6,908,478 B2 | 6/2005 | Alferness et al. |
| 6,911,043 B2 | 6/2005 | Myers et al. |
| 6,926,730 B1 | 8/2005 | Nguyen et al. |
| 6,966,925 B2 | 11/2005 | Stobie |
| 6,991,649 B2 | 1/2006 | Sievers |
| 6,997,950 B2 | 2/2006 | Chawla |
| 7,018,408 B2 | 3/2006 | Bailey et al. |
| 7,037,333 B2 | 5/2006 | Myers et al. |
| 7,048,754 B2 | 5/2006 | Martin et al. |
| 7,056,280 B2 | 6/2006 | Buckberg et al. |
| 7,070,618 B2 | 7/2006 | Streeter |
| 7,077,861 B2 | 7/2006 | Spence |
| 7,077,862 B2 | 7/2006 | Vidlund et al. |
| 7,083,628 B2 | 8/2006 | Bachman |
| 7,087,064 B1 | 8/2006 | Hyde |
| 7,112,207 B2 | 9/2006 | Allen et al. |
| 7,122,043 B2 | 10/2006 | Greenhalgh et al. |
| 7,160,322 B2 | 1/2007 | Gabbay |
| 7,166,126 B2 | 1/2007 | Spence et al. |
| 7,175,656 B2 | 2/2007 | Khairkhahan |
| 7,195,641 B2 | 3/2007 | Palmaz et al. |
| 7,217,284 B2 | 5/2007 | Houser et al. |
| 7,226,467 B2 | 6/2007 | Lucatero et al. |
| 7,275,546 B2 | 10/2007 | Buckberg et al. |
| 7,291,168 B2 | 11/2007 | Macoviak et al. |
| 7,294,148 B2 | 11/2007 | McCarthy |
| 7,296,577 B2 | 11/2007 | Taylor et al. |
| 7,316,706 B2 | 1/2008 | Bloom et al. |
| 7,320,704 B2 | 1/2008 | Lashinski et al. |
| 7,335,213 B1 | 2/2008 | Hyde et al. |
| 7,338,520 B2 | 3/2008 | Bailey et al. |
| 7,341,584 B1 | 3/2008 | Starkey |
| 7,357,814 B2 | 4/2008 | Gabbay |
| 7,374,572 B2 | 5/2008 | Gabbay |
| RE40,377 E | 6/2008 | Williamson, IV et al. |
| 7,381,220 B2 | 6/2008 | Macoviak et al. |
| 7,396,364 B2 | 7/2008 | Moaddeb et al. |
| 7,404,824 B1 | 7/2008 | Webler et al. |
| 7,435,257 B2 | 10/2008 | Lashinski et al. |
| 7,445,630 B2 | 11/2008 | Lashinski et al. |
| 7,455,689 B2 | 11/2008 | Johnson |
| 7,485,143 B2 | 2/2009 | Webler et al. |
| 7,510,573 B2 | 3/2009 | Gabbay |
| 7,510,576 B2 | 3/2009 | Langberg et al. |
| 7,527,646 B2 | 5/2009 | Rahdert et al. |
| 7,527,647 B2 | 5/2009 | Spence |
| 7,530,998 B1 | 5/2009 | Starkey |
| 7,534,259 B2 | 5/2009 | Lashinski et al. |
| 7,556,645 B2 | 7/2009 | Lashinski et al. |
| 7,559,936 B2 | 7/2009 | Levine |
| 7,563,267 B2 | 7/2009 | Goldfarb et al. |
| 7,563,273 B2 | 7/2009 | Goldfarb et al. |
| 7,591,847 B2 | 9/2009 | Navia et al. |
| 7,608,091 B2 | 10/2009 | Goldfarb et al. |
| 7,611,534 B2 | 11/2009 | Kapadia et al. |
| 7,621,948 B2 | 11/2009 | Herrmann et al. |
| 7,648,532 B2 | 1/2010 | Greenhalgh et al. |
| 7,655,015 B2 | 2/2010 | Goldfarb et al. |
| 7,658,762 B2 | 2/2010 | Lashinski et al. |
| 7,658,763 B2 | 2/2010 | Stable |
| 7,666,224 B2 | 2/2010 | Vidlund et al. |
| 7,674,286 B2 | 3/2010 | Alfieri et al. |
| 7,678,145 B2 | 3/2010 | Vidlund et al. |
| 7,682,391 B2 | 3/2010 | Johnson |
| 7,691,144 B2 | 4/2010 | Chang et al. |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,736,388 B2 | 6/2010 | Goldfarb et al. |
| 7,740,638 B2 | 6/2010 | Hyde |
| 7,744,609 B2 | 6/2010 | Allen et al. |
| 7,753,923 B2 | 7/2010 | St. Goar et al. |
| 7,758,491 B2 | 7/2010 | Buckner et al. |
| 7,758,595 B2 | 7/2010 | Allen et al. |
| 7,776,084 B2 | 8/2010 | Johnson |
| 7,785,366 B2 | 8/2010 | Maurer et al. |
| 7,799,038 B2 | 9/2010 | Sogard et al. |
| 7,803,187 B2 | 9/2010 | Hauser |
| 7,819,915 B2 | 10/2010 | Stobie et al. |
| 7,846,203 B2 | 12/2010 | Cribier |
| 7,887,552 B2 | 2/2011 | Bachman |
| 7,901,454 B2 | 3/2011 | Kapadia et al. |
| 7,909,866 B2 | 3/2011 | Stobie |
| 7,914,576 B2 | 3/2011 | Navia et al. |
| 7,927,370 B2 | 4/2011 | Webler et al. |
| 7,935,144 B2 | 5/2011 | Robin et al. |
| 7,935,145 B2 | 5/2011 | Alfieri et al. |
| 7,938,827 B2 | 5/2011 | Hauck et al. |
| 7,942,928 B2 | 5/2011 | Webler et al. |
| 7,951,195 B2 | 5/2011 | Antonsson et al. |
| 7,951,196 B2 | 5/2011 | McCarthy |
| 7,955,385 B2 | 6/2011 | Crittenden |
| 7,959,673 B2 | 6/2011 | Carpentier et al. |
| 7,981,139 B2 | 7/2011 | Martin et al. |
| 7,988,725 B2 | 8/2011 | Gross et al. |
| 7,993,396 B2 | 8/2011 | McCarthy |
| 7,998,151 B2 | 8/2011 | St. Goar et al. |
| 8,012,201 B2 | 9/2011 | Lashinski et al. |
| 8,012,202 B2 | 9/2011 | Alameddine |
| 8,016,882 B2 | 9/2011 | Macoviak et al. |
| 8,029,518 B2 | 10/2011 | Goldfarb et al. |
| 8,052,751 B2 | 11/2011 | Aklog et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,092,525 B2 | 1/2012 | Eliasen et al. |
| 8,118,866 B2 | 2/2012 | Herrmann et al. |
| 8,128,691 B2 | 3/2012 | Keranen |
| 8,133,272 B2 | 3/2012 | Hyde |
| 8,142,494 B2 | 3/2012 | Rahdert et al. |
| 8,142,495 B2 | 3/2012 | Hasenkam et al. |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,207 B2 | 5/2012 | Machold et al. |
| 8,187,299 B2 | 5/2012 | Goldfarb et al. |
| 8,187,323 B2 | 5/2012 | Mortier et al. |
| 8,204,605 B2 | 6/2012 | Hastings et al. |
| 8,206,439 B2 | 6/2012 | Gomez Duran |
| 8,216,230 B2 | 7/2012 | Hauck et al. |
| 8,216,256 B2 | 7/2012 | Raschdorf, Jr. et al. |
| 8,216,302 B2 | 7/2012 | Wilson et al. |
| 8,216,303 B2 | 7/2012 | Navia |
| 8,221,493 B2 | 7/2012 | Boyle et al. |
| 8,226,711 B2 | 7/2012 | Mortier et al. |
| 8,241,304 B2 | 8/2012 | Bachman |
| 8,241,351 B2 | 8/2012 | Cabiri |
| 8,252,050 B2 | 8/2012 | Maisano |
| 8,252,051 B2 | 8/2012 | Chau et al. |
| 8,262,725 B2 | 9/2012 | Subramanian |
| 8,277,502 B2 | 10/2012 | Miller et al. |
| 8,287,591 B2 | 10/2012 | Keidar et al. |
| 8,292,884 B2 | 10/2012 | Levine et al. |
| 8,308,796 B2 | 11/2012 | Lashinski et al. |
| 8,323,336 B2 | 12/2012 | Hill et al. |
| 8,337,390 B2 | 12/2012 | Ferrazzi |
| 8,353,956 B2 | 1/2013 | Miller et al. |
| 8,361,086 B2 | 1/2013 | Allen et al. |
| 8,377,118 B2 | 2/2013 | Lashinski et al. |
| 8,382,796 B2 | 2/2013 | Blaeser et al. |

(56) References Cited

U.S. PATENT DOCUMENTS

| | | |
|---|---|---|
| 8,382,828 B2 | 2/2013 | Roberts |
| 8,382,829 B1 | 2/2013 | Call et al. |
| RE44,075 E | 3/2013 | Williamson, IV et al. |
| 8,398,708 B2 | 3/2013 | Meiri et al. |
| 8,408,214 B2 | 4/2013 | Spenser |
| 8,413,573 B2 | 4/2013 | Rebecchi |
| 8,414,644 B2 | 4/2013 | Quadri et al. |
| 8,449,606 B2 | 5/2013 | Eliasen et al. |
| 8,454,683 B2 | 6/2013 | Rafiee et al. |
| 8,500,800 B2 | 8/2013 | Maisano et al. |
| 8,506,624 B2 | 8/2013 | Vidlund et al. |
| 8,523,881 B2 | 9/2013 | Cabiri et al. |
| 8,545,553 B2 | 10/2013 | Zipory et al. |
| 8,608,797 B2 | 12/2013 | Gross et al. |
| 8,657,872 B2 | 2/2014 | Seguin |
| 8,690,939 B2 | 4/2014 | Miller et al. |
| 8,715,342 B2 | 5/2014 | Zipory et al. |
| 8,734,467 B2 | 5/2014 | Miller et al. |
| 8,784,483 B2 | 7/2014 | Navia |
| 8,790,394 B2 | 7/2014 | Miller et al. |
| 8,795,352 B2 | 8/2014 | O'beirne et al. |
| 8,808,368 B2 | 8/2014 | Maisano et al. |
| 8,845,717 B2 | 9/2014 | Khairkhahan et al. |
| 8,858,623 B2 | 10/2014 | Miller et al. |
| 8,888,843 B2 | 11/2014 | Khairkhahan et al. |
| 8,888,844 B2 | 11/2014 | Eliasen et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,940,042 B2 | 1/2015 | Miller et al. |
| 8,940,044 B2 | 1/2015 | Hammer et al. |
| 9,005,279 B2 | 4/2015 | Gabbay |
| 9,011,520 B2 | 4/2015 | Miller et al. |
| 9,011,530 B2 | 4/2015 | Reich et al. |
| 9,056,006 B2 | 6/2015 | Edelman et al. |
| 9,119,719 B2 | 9/2015 | Zipory et al. |
| 9,180,007 B2 | 11/2015 | Reich et al. |
| 9,192,472 B2 | 11/2015 | Gross et al. |
| 9,204,964 B2 | 12/2015 | Dahlgren et al. |
| 9,232,999 B2 | 1/2016 | Maurer et al. |
| 9,265,608 B2 | 2/2016 | Miller et al. |
| 9,277,994 B2 | 3/2016 | Miller et al. |
| 9,351,830 B2 | 5/2016 | Gross et al. |
| 9,414,921 B2 | 8/2016 | Miller et al. |
| 9,452,048 B2 | 9/2016 | O'beirne et al. |
| 9,474,606 B2 | 10/2016 | Zipory et al. |
| 9,526,613 B2 | 12/2016 | Gross et al. |
| 9,549,817 B2 | 1/2017 | Rafiee |
| 9,554,906 B2 | 1/2017 | Aklog et al. |
| 9,561,104 B2 | 2/2017 | Miller et al. |
| 9,592,118 B2 | 3/2017 | Khairkhahan et al. |
| 9,592,121 B1 | 3/2017 | Khairkhahan |
| 9,592,122 B2 | 3/2017 | Zipory et al. |
| 9,610,162 B2 | 4/2017 | Zipory et al. |
| 9,610,163 B2 | 4/2017 | Khairkhahan et al. |
| 9,622,861 B2 | 4/2017 | Miller et al. |
| 9,636,224 B2 | 5/2017 | Zipory et al. |
| 9,662,209 B2 | 5/2017 | Gross et al. |
| 9,713,530 B2 | 7/2017 | Cabiri et al. |
| 9,724,192 B2 | 8/2017 | Sheps et al. |
| 9,730,793 B2 | 8/2017 | Reich et al. |
| 9,775,709 B2 | 10/2017 | Miller et al. |
| 9,814,572 B2 | 11/2017 | Edelman et al. |
| 9,872,769 B2 | 1/2018 | Gross et al. |
| 9,883,943 B2 | 2/2018 | Gross et al. |
| 9,918,840 B2 | 3/2018 | Reich et al. |
| 9,937,042 B2 | 4/2018 | Cabiri et al. |
| 9,949,828 B2 | 4/2018 | Sheps et al. |
| 9,968,452 B2 | 5/2018 | Sheps et al. |
| 9,968,454 B2 | 5/2018 | Reich et al. |
| 9,974,653 B2 | 5/2018 | Gross et al. |
| 10,028,832 B2 | 7/2018 | Quill et al. |
| 10,098,737 B2 | 10/2018 | Miller et al. |
| 10,123,874 B2 | 11/2018 | Khairkhahan et al. |
| 10,130,472 B2 | 11/2018 | O'beirne et al. |
| 10,166,098 B2 | 1/2019 | Khairkhahan et al. |
| 10,195,030 B2 | 2/2019 | Gross et al. |
| 10,226,342 B2 | 3/2019 | Kutzik et al. |
| 10,251,635 B2 | 4/2019 | Khairkhahan et al. |
| 10,265,170 B2 | 4/2019 | Zipory et al. |
| 10,299,793 B2 | 5/2019 | Zipory et al. |
| 10,350,068 B2 | 7/2019 | Miller et al. |
| 10,357,366 B2 | 7/2019 | Gross et al. |
| 10,363,136 B2 | 7/2019 | Miller et al. |
| 10,363,137 B2 | 7/2019 | Gross et al. |
| 10,368,982 B2 | 8/2019 | Weber et al. |
| 10,376,266 B2 | 8/2019 | Herman et al. |
| 10,376,365 B2 | 8/2019 | Khairkhahan et al. |
| 10,383,726 B2 | 8/2019 | Kramer |
| 10,433,955 B2 | 10/2019 | Edelman et al. |
| 10,449,046 B2 | 10/2019 | Rafiee |
| 10,449,333 B2 | 10/2019 | Hammer et al. |
| 10,470,882 B2 | 11/2019 | Gross et al. |
| 10,470,883 B2 | 11/2019 | Khairkhahan et al. |
| 10,478,303 B2 | 11/2019 | Khairkhahan et al. |
| 10,492,909 B2 | 12/2019 | Miller et al. |
| 10,500,048 B2 | 12/2019 | Khairkhahan et al. |
| 10,512,542 B2 | 12/2019 | Khairkhahan et al. |
| 10,517,719 B2 | 12/2019 | Miller et al. |
| 10,543,088 B2 | 1/2020 | Lashinski |
| 10,548,729 B2 | 2/2020 | Zipory et al. |
| 10,548,731 B2 | 2/2020 | Lashinski et al. |
| 10,561,498 B2 | 2/2020 | Gross et al. |
| 10,568,738 B2 | 2/2020 | Sheps et al. |
| 10,610,360 B2 | 4/2020 | Reich et al. |
| 10,653,524 B2 | 5/2020 | Khairkhahan et al. |
| 10,751,180 B2 | 8/2020 | Schewel |
| 11,000,372 B2 | 5/2021 | Khairkhahan et al. |
| 2001/0007956 A1 | 7/2001 | Letac et al. |
| 2001/0021872 A1 | 9/2001 | Bailey et al. |
| 2002/0029080 A1 | 3/2002 | Mortier et al. |
| 2002/0058995 A1 | 5/2002 | Stevens |
| 2002/0116024 A1 | 8/2002 | Goldberg et al. |
| 2002/0138135 A1 | 9/2002 | Duerig |
| 2002/0188301 A1 | 12/2002 | Dallara et al. |
| 2003/0023248 A1 | 1/2003 | Parodi |
| 2003/0100943 A1 | 5/2003 | Bolduc |
| 2003/0105474 A1 | 6/2003 | Bonutti |
| 2003/0135263 A1 | 7/2003 | Rourke et al. |
| 2003/0191497 A1 | 10/2003 | Cope |
| 2003/0199975 A1 | 10/2003 | Gabbay |
| 2004/0082956 A1 | 4/2004 | Baldwin et al. |
| 2004/0088047 A1 | 5/2004 | Spence et al. |
| 2004/0143323 A1 | 7/2004 | Chawla |
| 2004/0172046 A1 | 9/2004 | Hlavka et al. |
| 2004/0193217 A1 | 9/2004 | Lubbers et al. |
| 2004/0210307 A1 | 10/2004 | Khairkhahan |
| 2005/0004665 A1 | 1/2005 | Aklog |
| 2005/0004668 A1 | 1/2005 | Aklog et al. |
| 2005/0010287 A1 | 1/2005 | Macoviak et al. |
| 2005/0075727 A1 | 4/2005 | Wheatley et al. |
| 2005/0096740 A1 | 5/2005 | Langberg et al. |
| 2005/0107871 A1 | 5/2005 | Realyvasquez |
| 2005/0159810 A1 | 7/2005 | Filsoufi |
| 2005/0177180 A1 | 8/2005 | Kaganov et al. |
| 2005/0228495 A1 | 10/2005 | Macoviak |
| 2005/0261708 A1 | 11/2005 | Pasricha et al. |
| 2005/0283232 A1 | 12/2005 | Gabbay |
| 2006/0058871 A1 | 3/2006 | Zakay et al. |
| 2006/0122608 A1 | 6/2006 | Fallin et al. |
| 2006/0149368 A1 | 7/2006 | Spence |
| 2006/0190030 A1 | 8/2006 | To et al. |
| 2006/0252984 A1 | 11/2006 | Rahdert et al. |
| 2007/0005069 A1 | 1/2007 | Contiliano et al. |
| 2007/0049970 A1 | 3/2007 | Belef et al. |
| 2007/0093890 A1 | 4/2007 | Eliasen et al. |
| 2007/0112352 A1 | 5/2007 | Sorensen et al. |
| 2007/0112425 A1 | 5/2007 | Schaller et al. |
| 2007/0118151 A1 | 5/2007 | Davidson |
| 2007/0129758 A1 | 6/2007 | Saadat |
| 2007/0185571 A1 | 8/2007 | Kapadia et al. |
| 2007/0233239 A1 | 10/2007 | Navia et al. |
| 2007/0239272 A1 | 10/2007 | Navia et al. |

(56) References Cited

U.S. PATENT DOCUMENTS

| | | |
|---|---|---|
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250160 A1 | 10/2007 | Rafiee |
| 2007/0255399 A1 | 11/2007 | Eliasen et al. |
| 2007/0265658 A1 | 11/2007 | Nelson et al. |
| 2007/0265700 A1 | 11/2007 | Eliasen et al. |
| 2007/0265702 A1 | 11/2007 | Lattouf |
| 2007/0293943 A1 | 12/2007 | Quinn |
| 2008/0065204 A1 | 3/2008 | Macoviak et al. |
| 2008/0109075 A1 | 5/2008 | Keranen |
| 2008/0125860 A1 | 5/2008 | Webler et al. |
| 2008/0195205 A1 | 8/2008 | Schwartz |
| 2008/0262609 A1 | 10/2008 | Gross et al. |
| 2008/0319541 A1 | 12/2008 | Filsoufi |
| 2009/0012354 A1 | 1/2009 | Wood |
| 2009/0088836 A1 | 4/2009 | Bishop et al. |
| 2009/0177277 A1 | 7/2009 | Milo |
| 2009/0234404 A1 | 9/2009 | Fitzgerald et al. |
| 2009/0259304 A1 | 10/2009 | O'Beirne et al. |
| 2009/0259307 A1 | 10/2009 | Gross et al. |
| 2009/0287304 A1 | 11/2009 | Dahlgren et al. |
| 2009/0326648 A1 | 12/2009 | Machold et al. |
| 2010/0069954 A1 | 3/2010 | Blaeser et al. |
| 2010/0121435 A1 | 5/2010 | Subramanian et al. |
| 2010/0131057 A1 | 5/2010 | Subramanian et al. |
| 2010/0161043 A1 | 6/2010 | Maisano et al. |
| 2010/0161047 A1 | 6/2010 | Cabiri et al. |
| 2010/0249947 A1 | 9/2010 | Lesh et al. |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0280606 A1 | 11/2010 | Naor |
| 2010/0286767 A1 | 11/2010 | Zipory et al. |
| 2010/0298929 A1 | 11/2010 | Thornton et al. |
| 2010/0312333 A1 | 12/2010 | Navia et al. |
| 2011/0004299 A1 | 1/2011 | Navia et al. |
| 2011/0082538 A1 | 4/2011 | Dahlgren et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0224785 A1 | 9/2011 | Hacohen |
| 2011/0288635 A1 | 11/2011 | Miller et al. |
| 2011/0301698 A1 | 12/2011 | Miller et al. |
| 2012/0022557 A1 | 1/2012 | Cabiri et al. |
| 2012/0022644 A1 | 1/2012 | Reich et al. |
| 2012/0078360 A1 | 3/2012 | Rafiee |
| 2012/0136436 A1 | 5/2012 | Cabiri et al. |
| 2012/0165930 A1 | 6/2012 | Gifford et al. |
| 2012/0197388 A1 | 8/2012 | Khairkhahan et al. |
| 2012/0203336 A1 | 8/2012 | Annest |
| 2012/0283757 A1 | 11/2012 | Miller et al. |
| 2012/0323316 A1 | 12/2012 | Chau et al. |
| 2012/0330410 A1 | 12/2012 | Hammer et al. |
| 2012/0330411 A1 | 12/2012 | Gross et al. |
| 2013/0023985 A1 | 1/2013 | Khairkhahan et al. |
| 2013/0096672 A1 | 4/2013 | Reich et al. |
| 2013/0116776 A1 | 5/2013 | Gross et al. |
| 2013/0116780 A1 | 5/2013 | Miller et al. |
| 2013/0131792 A1 | 5/2013 | Miller et al. |
| 2013/0190861 A1 | 7/2013 | Chau et al. |
| 2013/0190866 A1 | 7/2013 | Zipory et al. |
| 2013/0238024 A1 | 9/2013 | Taylor et al. |
| 2013/0282028 A1 | 10/2013 | Conklin et al. |
| 2013/0338763 A1 | 12/2013 | Rowe et al. |
| 2014/0018906 A1 | 1/2014 | Rafiee |
| 2014/0039615 A1 | 2/2014 | Padala et al. |
| 2014/0067048 A1 | 3/2014 | Chau |
| 2014/0094903 A1 | 4/2014 | Miller et al. |
| 2014/0128965 A1 | 5/2014 | Rafiee |
| 2014/0142695 A1 | 5/2014 | Gross et al. |
| 2014/0148898 A1 | 5/2014 | Gross et al. |
| 2014/0222137 A1 | 8/2014 | Miller et al. |
| 2014/0243963 A1 | 8/2014 | Sheps et al. |
| 2014/0276648 A1 | 9/2014 | Hammer et al. |
| 2014/0277088 A1 | 9/2014 | Friedman |
| 2014/0309661 A1 | 10/2014 | Sheps et al. |
| 2014/0343668 A1 | 11/2014 | Zipory et al. |
| 2014/0358223 A1 | 12/2014 | Rafiee et al. |
| 2014/0379075 A1 | 12/2014 | Maurer et al. |
| 2015/0012087 A1 | 1/2015 | Miller et al. |
| 2015/0039083 A1 | 2/2015 | Rafiee et al. |
| 2015/0081014 A1 | 3/2015 | Gross et al. |
| 2015/0100116 A1 | 4/2015 | Mohl et al. |
| 2015/0105855 A1 | 4/2015 | Cabiri et al. |
| 2015/0112429 A1 | 4/2015 | Khairkhahan et al. |
| 2015/0112432 A1 | 4/2015 | Reich et al. |
| 2015/0119981 A1 | 4/2015 | Khairkhahan et al. |
| 2015/0164637 A1 | 6/2015 | Khairkhahan et al. |
| 2015/0182336 A1 | 7/2015 | Zipory et al. |
| 2015/0202043 A1 | 7/2015 | Zakai et al. |
| 2015/0230924 A1 | 8/2015 | Miller et al. |
| 2015/0257877 A1 | 9/2015 | Hernandez |
| 2015/0272586 A1 | 10/2015 | Herman et al. |
| 2015/0272734 A1 | 10/2015 | Sheps et al. |
| 2015/0297212 A1 | 10/2015 | Reich et al. |
| 2015/0366556 A1 | 12/2015 | Khairkhahan et al. |
| 2015/0366666 A1 | 12/2015 | Khairkhahan et al. |
| 2016/0008132 A1 | 1/2016 | Cabiri et al. |
| 2016/0030176 A1 | 2/2016 | Mohl et al. |
| 2016/0058557 A1 | 3/2016 | Reich et al. |
| 2016/0074164 A1 | 3/2016 | Naor |
| 2016/0089233 A1 | 3/2016 | Lee et al. |
| 2016/0106437 A1 | 4/2016 | van der Burg et al. |
| 2016/0113767 A1 | 4/2016 | Miller et al. |
| 2016/0158008 A1 | 6/2016 | Miller et al. |
| 2016/0262755 A1 | 9/2016 | Zipory et al. |
| 2016/0324639 A1 | 11/2016 | Nguyen et al. |
| 2016/0331523 A1 | 11/2016 | Chau et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0100249 A1 | 4/2017 | Miller et al. |
| 2017/0105839 A1 | 4/2017 | Subramanian et al. |
| 2017/0135815 A1 | 5/2017 | Gross et al. |
| 2017/0135816 A1 | 5/2017 | Lashinski et al. |
| 2017/0189186 A1 | 7/2017 | Mohl |
| 2017/0196691 A1 | 7/2017 | Zipory et al. |
| 2017/0209270 A1 | 7/2017 | Miller et al. |
| 2017/0245993 A1 | 8/2017 | Gross et al. |
| 2017/0245994 A1 | 8/2017 | Khairkhahan et al. |
| 2017/0258588 A1 | 9/2017 | Zipory et al. |
| 2017/0258590 A1 | 9/2017 | Khairkhahan et al. |
| 2017/0265995 A1 | 9/2017 | Khairkhahan et al. |
| 2017/0296340 A1 | 10/2017 | Gross et al. |
| 2017/0325958 A1 | 11/2017 | Reich et al. |
| 2017/0325959 A1 | 11/2017 | Sheps et al. |
| 2017/0354500 A1 | 12/2017 | Martinez et al. |
| 2017/0367825 A1 | 12/2017 | Cabiri et al. |
| 2018/0008409 A1 | 1/2018 | Kutzik et al. |
| 2018/0014933 A1 | 1/2018 | Miller et al. |
| 2018/0014934 A1 | 1/2018 | Miller et al. |
| 2018/0049875 A1 | 2/2018 | Iflah et al. |
| 2018/0116797 A9 | 5/2018 | Miller et al. |
| 2018/0125657 A1 | 5/2018 | Dahlgren et al. |
| 2018/0228608 A1 | 8/2018 | Sheps et al. |
| 2018/0250133 A1 | 9/2018 | Reich et al. |
| 2018/0256318 A1 | 9/2018 | Khairkhahan |
| 2018/0256333 A1 | 9/2018 | Cabiri et al. |
| 2018/0256334 A1 | 9/2018 | Sheps et al. |
| 2018/0263776 A1 | 9/2018 | Gross et al. |
| 2018/0263777 A1 | 9/2018 | Gross et al. |
| 2018/0318080 A1 | 11/2018 | Quill et al. |
| 2019/0008641 A1 | 1/2019 | Dahlgren et al. |
| 2019/0046318 A1 | 2/2019 | Miller et al. |
| 2019/0070004 A1 | 3/2019 | Iflah et al. |
| 2019/0076249 A1 | 3/2019 | Khairkhahan |
| 2019/0125325 A1 | 5/2019 | Sheps et al. |
| 2019/0133586 A1 | 5/2019 | Zipory et al. |
| 2019/0151090 A1 | 5/2019 | Gross et al. |
| 2019/0151093 A1 | 5/2019 | Keidar et al. |
| 2019/0159898 A1 | 5/2019 | Kutzik et al. |

(56) References Cited

U.S. PATENT DOCUMENTS

| | | |
|---|---|---|
| 2019/0167425 A1 | 6/2019 | Reich et al. |
| 2019/0175344 A1 | 6/2019 | Khairkhahan |
| 2019/0201191 A1 | 7/2019 | McLean et al. |
| 2019/0216600 A1 | 7/2019 | Zipory et al. |
| 2019/0254821 A1 | 8/2019 | Rafiee et al. |
| 2019/0269512 A9 | 9/2019 | Lashinski |
| 2019/0269513 A9 | 9/2019 | Cabiri et al. |
| 2019/0274830 A1 | 9/2019 | Miller et al. |
| 2019/0282358 A1 | 9/2019 | Khairkhahan et al. |
| 2019/0282364 A1 | 9/2019 | Khairkhahan et al. |
| 2019/0298332 A1 | 10/2019 | Khairkhahan et al. |
| 2019/0321049 A1 | 10/2019 | Herman et al. |
| 2019/0336288 A1 | 11/2019 | Gross et al. |
| 2019/0336289 A1 | 11/2019 | Miller et al. |
| 2019/0350703 A1 | 11/2019 | Weber et al. |
| 2019/0350705 A1 | 11/2019 | Schewel et al. |
| 2019/0374343 A1 | 12/2019 | Lashinski et al. |
| 2019/0374750 A1 | 12/2019 | Hammer et al. |
| 2019/0380834 A1 | 12/2019 | Rafiee |
| 2020/0015971 A1 | 1/2020 | Brauon et al. |
| 2020/0030097 A1 | 1/2020 | Khairkhahan et al. |
| 2020/0038186 A1 | 2/2020 | Gross et al. |
| 2020/0100899 A1 | 4/2020 | Miller et al. |
| 2020/0113685 A1 | 4/2020 | Miller et al. |
| 2020/0214841 A1 | 7/2020 | Khairkhahan et al. |
| 2020/0222185 A1 | 7/2020 | Kappetein et al. |
| 2020/0275974 A1 | 9/2020 | Gifford et al. |
| 2020/0289265 A1 | 9/2020 | Gifford et al. |
| 2020/0337843 A1 | 10/2020 | Khairkhahan et al. |
| 2020/0383776 A1 | 12/2020 | Schewel |
| 2020/0397567 A1 | 12/2020 | Khairkhahan et al. |
| 2021/0085462 A1 | 3/2021 | Gifford et al. |

FOREIGN PATENT DOCUMENTS

| | | |
|---|---|---|
| CN | 101056596 | 10/2007 |
| CN | 101068508 | 11/2007 |
| CN | 101947146 | 1/2011 |
| CN | 102065777 | 5/2011 |
| CN | 102458309 | 5/2012 |
| CN | 202821715 | 3/2013 |
| CN | 10338726 | 10/2013 |
| CN | 102905648 | 1/2015 |
| CN | 104394803 | 3/2015 |
| CN | 104582637 | 4/2015 |
| CN | 105451688 | 3/2016 |
| EP | 1 294 310 | 3/2003 |
| EP | 1 959 865 | 8/2008 |
| EP | 2 410 948 | 2/2012 |
| EP | 1 796 597 | 1/2013 |
| EP | 2 661 239 | 11/2013 |
| EP | 2 667 824 | 12/2013 |
| EP | 2 995 279 | 3/2016 |
| JP | S54-088693 | 7/1979 |
| JP | 2005-535384 | 11/2005 |
| JP | 2007-518492 | 7/2007 |
| JP | 2008-517672 | 5/2008 |
| JP | 2010-511469 | 4/2010 |
| JP | 2012-511402 | 5/2012 |
| JP | 2012-520716 | 9/2012 |
| JP | 2014-510563 | 5/2014 |
| JP | 2014-231015 | 12/2014 |
| JP | 2015-523898 | 8/2016 |
| JP | 2016-533798 | 11/2016 |
| WO | WO 97/007744 | 3/1997 |
| WO | WO 99/53869 | 10/1998 |
| WO | WO 2004/014258 | 2/2004 |
| WO | WO 2005/069875 | 8/2005 |
| WO | WO 2006/032051 | 3/2006 |
| WO | WO 2006/041877 | 4/2006 |
| WO | WO 2006/086434 | 8/2006 |
| WO | WO 2007/062054 | 5/2007 |
| WO | WO 2007/135101 | 11/2007 |
| WO | WO 2007/140470 | 12/2007 |
| WO | WO 2008/068756 | 6/2008 |
| WO | WO 2008/141322 | 11/2008 |
| WO | WO 2010/106438 | 9/2010 |
| WO | WO 2011/037891 | 3/2011 |
| WO | WO 2011/047168 | 4/2011 |
| WO | WO 2012/061809 | 5/2012 |
| WO | WO 2012/092437 | 7/2012 |
| WO | WO 2012/102928 | 8/2012 |
| WO | WO 2013/131069 | 9/2013 |
| WO | WO 2013/173587 | 11/2013 |
| WO | WO 2013/178335 | 12/2013 |
| WO | WO 2013/192107 | 12/2013 |
| WO | WO 2014/181336 | 11/2014 |
| WO | WO 2014/207575 | 12/2014 |
| WO | WO 2015/020971 | 2/2015 |
| WO | WO 2015/052570 | 4/2015 |
| WO | WO 2015/061533 | 4/2015 |
| WO | WO 2015/195823 | 12/2015 |
| WO | WO 2015/200497 | 12/2015 |
| WO | WO 2016/178136 | 11/2016 |
| WO | WO 2016/183485 | 11/2016 |
| WO | WO 2017/079279 | 5/2017 |
| WO | WO 2017/136596 | 8/2017 |
| WO | WO 2019/116322 | 6/2019 |
| WO | WO 2019/222694 | 11/2019 |
| WO | WO 2019/241777 | 12/2019 |

OTHER PUBLICATIONS

Office Action for JP 2016-525999 dated Mar. 16, 2020.
Office Action for CN 201580044329.0 dated Mar. 3, 2020.
Office Action for 2016-573983 dated May 11, 2020.
Office Action for CN 201580044329.0 dated Aug. 26, 2020.
Office Action for EP 15812032.9, dated Jul. 6, 2020.
Office Action for JP 2016-574967 dated Jun. 29, 2020.
Office Action for JP 2018-543021 dated Oct. 27, 2020.
Office Action for CA 2,877,344 dated Dec. 23, 2020.
Office Action for CA 2,934,182 dated Dec. 9, 2020.
Office Action for JP 2020-082001 dated Mar. 29, 2021.
Extended European Search Report, EP 18768736.3, dated Oct. 9, 2020.
International Search Report for Application No. PCT/US2020/065261 dated Apr. 13, 2021 in 13 pages.
Office Action for CN 201880031519.2 dated May 19, 2021.
Office Action for EP 13806272.4, dated Mar. 23, 2021.
Office Action for EP 14856738.1, dated Apr. 23, 2021.
Office Action for JP 2020-085273 dated May 31, 2021.
Office Action for CA 2,934,182 dated Jun. 30, 2021.
Office Action for CA 2,958,065 dated Jul. 9, 2021.
U.S. Appl. No. 16/675,565, filed Nov. 6, 2019, Khairkhahan et al.
U.S. Appl. No. 16/685,338, filed Nov. 15, 2019, Khairkhahan.
U.S. Appl. No. 16/705,605, filed Dec. 6, 2019, Khairkhahan et al.
Biocina et al., Mitral Valve Repair With The New Mitrofast® Repair System, Dubrava University Hospital, Zagreb, Crotia, Mitrofast Abstract European Soc CVS 55th Congress—May 11-14, 2006 Suppl 1 to vol. 5.
Biocina, The arteficial coaptation surface concept in mitral valve repair, University of Zagreb School of Medicine, Department of Cardiac Surgery, Savudrija Mitrofast 2010.
Chiam et al., Percutaneous Transcatheter Mitral Valve Repair, The American College of Cardiology Foundation, JACC: Cardiovascular Interventions, vol. 4 No. 1, Jan. 2011:1-13.
Jassar et al., Posterior Leaflet Augmentation in Ischemic Mitral Regurgitation Increases Leaflet Coaptation and Mobility, The Society of Thoracic Surgeons, Ann Thorac Surg 2012; 94:1438-45.
Langer et al., Posterior mitral leaflet extension: An adjunctive repair option for ischemic mitral regurgitation?, Surgery for Acquired Cardiovascular Disease, The Journal of Thoracic and Cardiovascular Surgery, Apr. 2006, downloaded Jun. 18, 2011.
Mohl et al., The Angel Valve Concept, Vienna University of Technology, Medical University of Vienna, Technology Offer, 1 page.
Mohl et al., An Innovative Concept for Transcatheter Treatment of Annular Dilatation and Restrictive Leaflet Motion in Mitral Insufficiency, Medical University of Vienna, 1 page.

(56) References Cited

OTHER PUBLICATIONS

Piemonte et al., Cardiovascular™: The Mitral Valve Spacer, Presented at Transcatheter Cardiovascular Therapeutics Conference—TCT Conference, Oct. 2008.
Rumel et al, The Correction of Mitral Insufficiency with a Trans-Valvular Polyvinyl Formalinized Plastic (Ivalon) Sponge Prosthesis: A Preliminary Report, American College of Chest Physicians, 1958;33;401-413, Dec. 2, 2010.
International Preliminary Report on Patentability for PCT/US2012/021744 dated Aug. 8, 2013 in 15 pages.
International Search Report for Application No. PCT/US2013/046173 dated Oct. 4, 2013 in 15 pages.
International Search Report for Application No. PCT/US2014/061901 dated Jan. 26, 2015 in 14 pages.
International Search Report for Application No. PCT/US2015/036260 dated Oct. 1, 2015 in 20 pages.
International Search Report for Application No. PCT/US2015/037451 dated Oct. 6, 2015 in 12 pages.
International Search Report for Application No. PCT/US2016/060094 dated Feb. 9, 2017 in 8 pages.
International Search Report for Application No. PCT/US2018/022043 dated Jun. 25, 2018 in 13 pages.
Extended European Search Report, EP 12738989.8, dated May 24, 2016.
Office Action for EP 12738989.8 dated Mar. 3, 2017.
Office Action for EP 12738989.8 dated Sep. 19, 2017.
Extended European Search Report, EP 13806272.4, dated Nov. 11, 2015.
Extended European Search Report, EP 14856738.1, dated Jun. 7, 2017.
Extended European Search Report, EP 15809346.8, dated Feb. 13, 2018.
Extended European Search Report, EP 15812032.9, dated Oct. 18, 2017.
Extended European Search Report, EP 16862864.2, dated May 10, 2019.
Office Action for CA 2,825,520 dated Nov. 27, 2017.
Office Action for CA 2,825,520 dated Aug. 21, 2018.
Office Action for CA 2,877,344 dated Mar. 12, 2019.
Office Action for CA 2,877,344 dated Oct. 9, 2019.
Office Action for CN 201280006673.7 dated Dec. 10, 2014.
Office Action for CN 201280006673.7 dated Sep. 22, 2015.
Office Action for CN 201280006673.7 dated Feb. 1, 2016.
Office Action for CN 201380044122.4 dated Nov. 4, 2015.
Office Action for CN 201380044122.4 dated Aug. 24, 2016.
Office Action for CN 201480070933.6 dated May 10, 2017.
Office Action for CN 201480070933.6 dated Dec. 25, 2017.
Office Action for CN 201480070933.6 dated Aug. 10, 2018.
Office Action for CN 201480070933.6 dated Apr. 17, 2019.
Office Action for CN 201580044329.0 dated Jan. 17, 2018.
Office Action for CN 201580044329.0 dated Jul. 29, 2019.
Office Action for CN 201580045375.2 dated Mar. 29, 2018.
Office Action for CN 201580045375.2 dated Nov. 12, 2018.
Office Action for CN 201680077877.8 dated Aug. 15, 2019.
Office Action for EP 15812032.9, dated Oct. 10, 2019.
Office Action for JP 2013-552015 dated Dec. 7, 2015.
Office Action for JP 2013-552015 dated Oct. 7, 2016.
Office Action for JP 2013-552015 dated Jun. 5, 2017.
Office Action for JP 2015-518499 dated Feb. 27, 2017.
Office Action for JP 2015-518499 dated Aug. 31, 2017.
Office Action for JP 2015-518499 dated Aug. 20, 2018.
Office Action for JP 2016-525999 dated Jul. 9, 2018.
Office Action for JP 2016-525999 dated Jun. 27, 2019.
Office Action for 2016-573983 dated Apr. 1, 2019.
Office Action for 2016-573983 dated Nov. 11, 2019.
Office Action for JP 2016-574967 dated May 7, 2019.
Office Action for JP 2016-574967 dated Dec. 29, 2019.
International Search Report for Application No. PCT/US2019/050331 dated Sep. 10, 2019 in 9 pages.

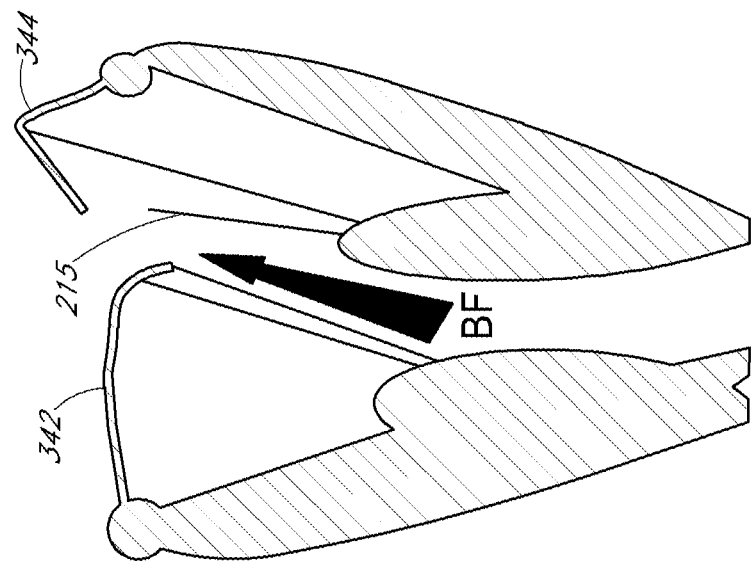
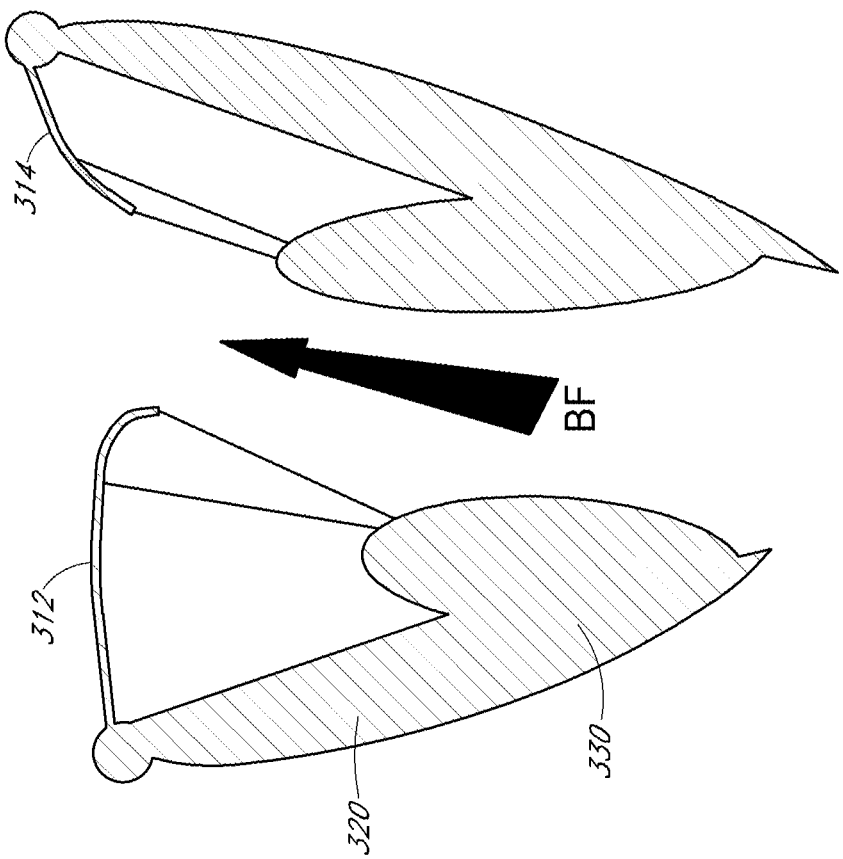
FIG. 4B
FIG. 4A

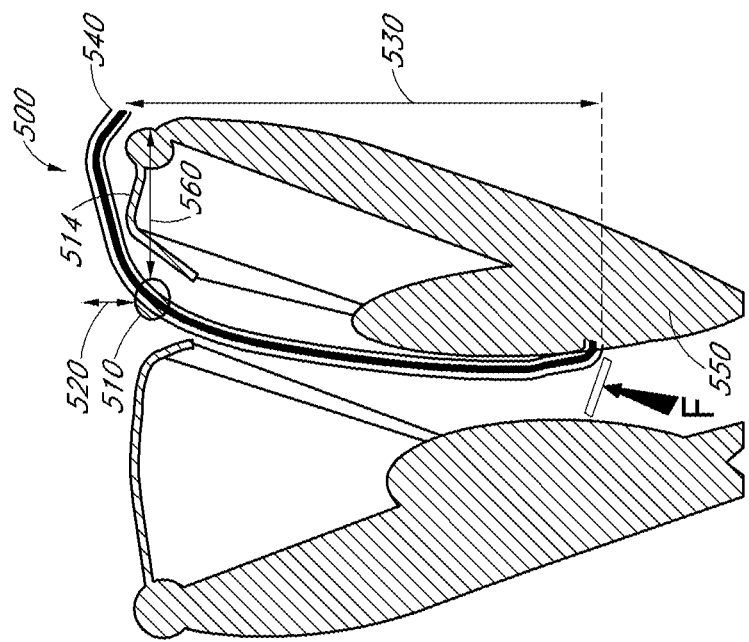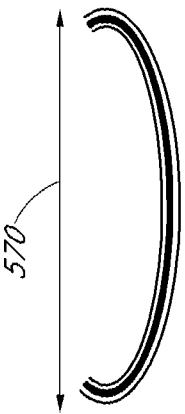
FIG. 5D
FIG. 5F
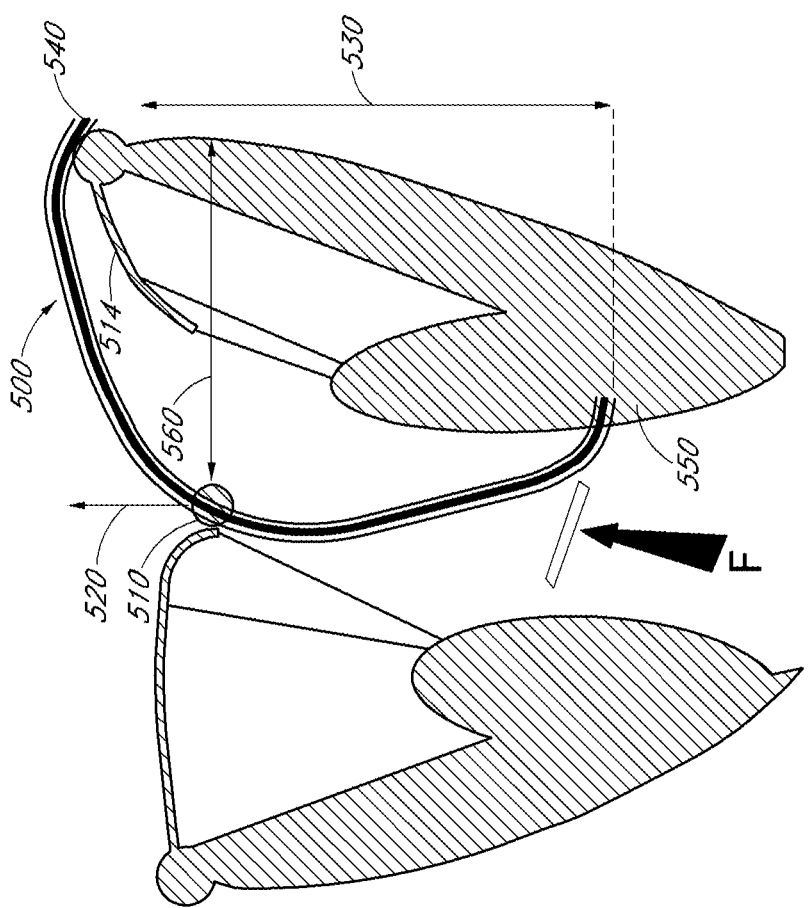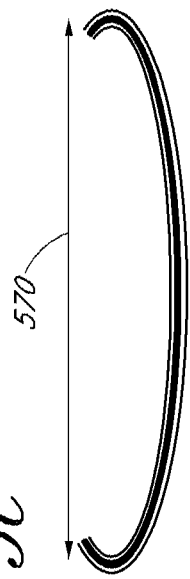
FIG. 5C
FIG. 5E

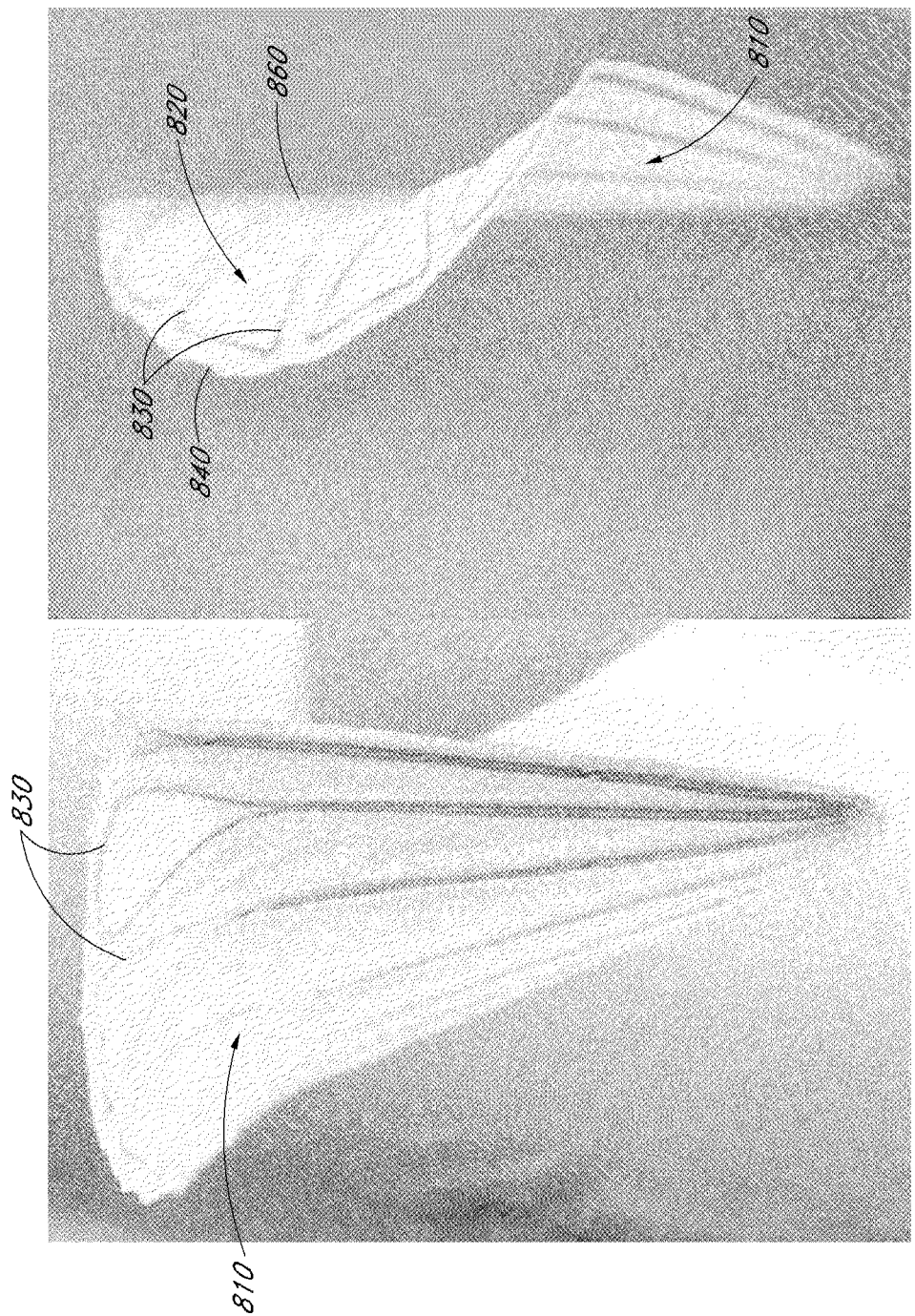

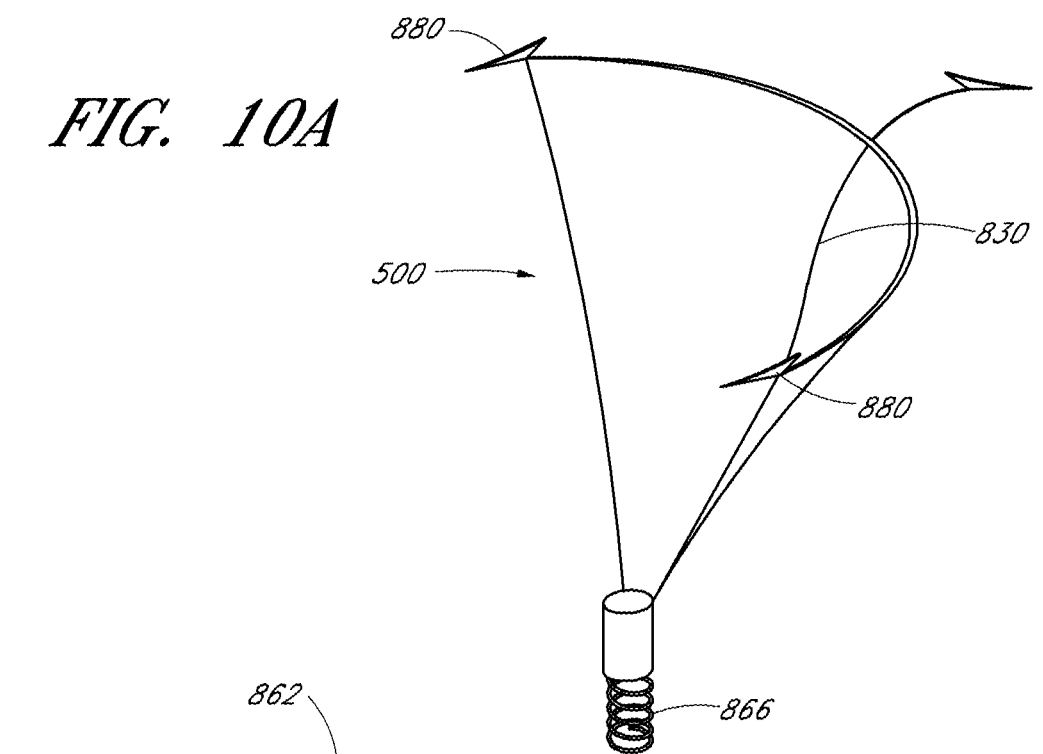
FIG. 10A
FIG. 10B
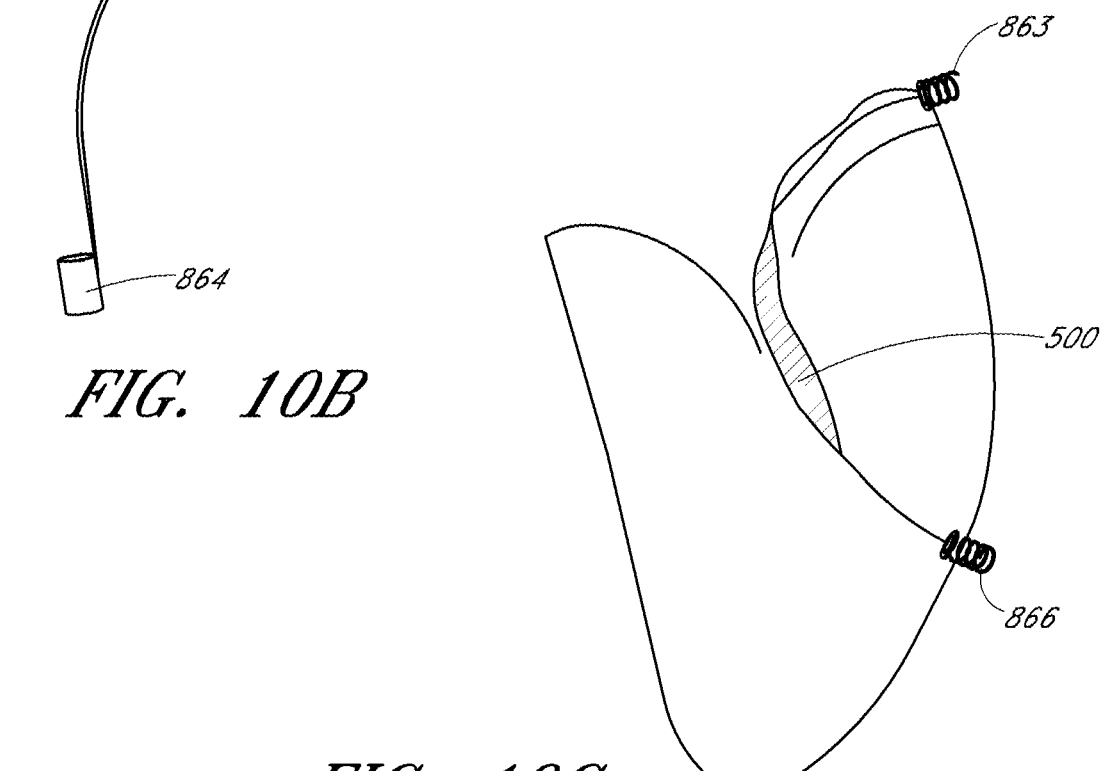
FIG. 10C

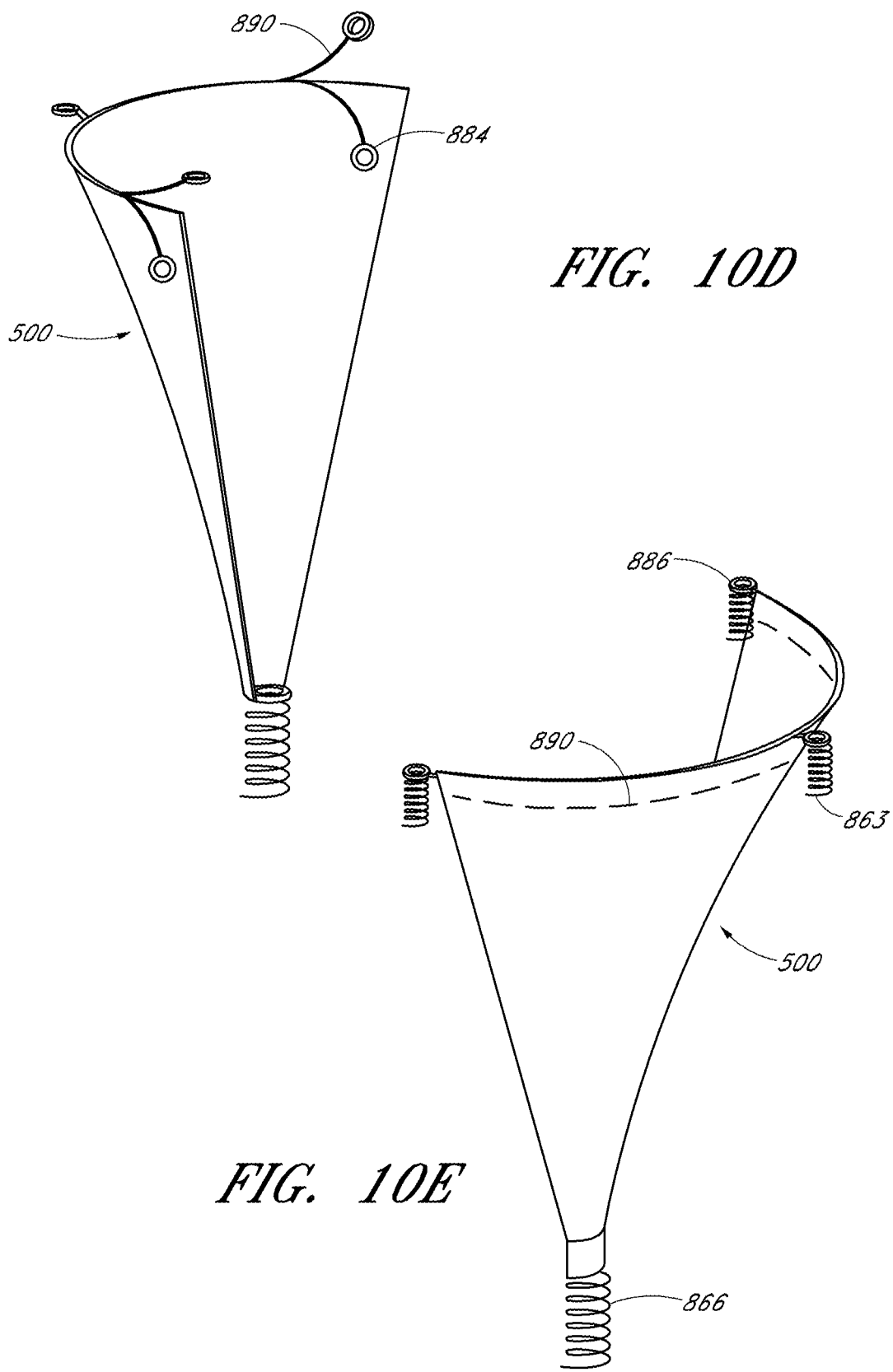

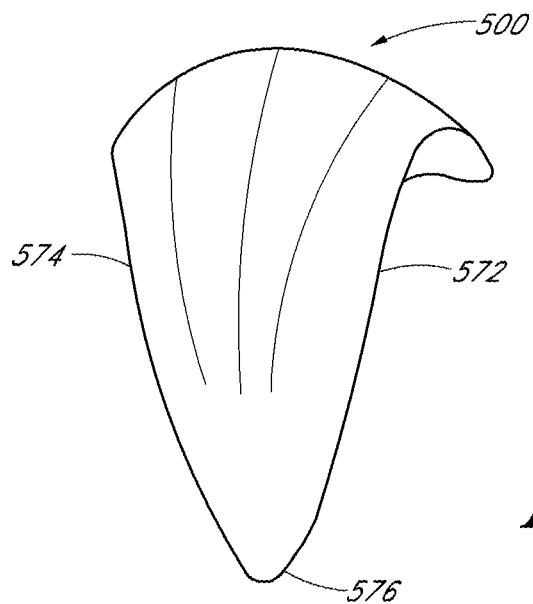
FIG. 13C
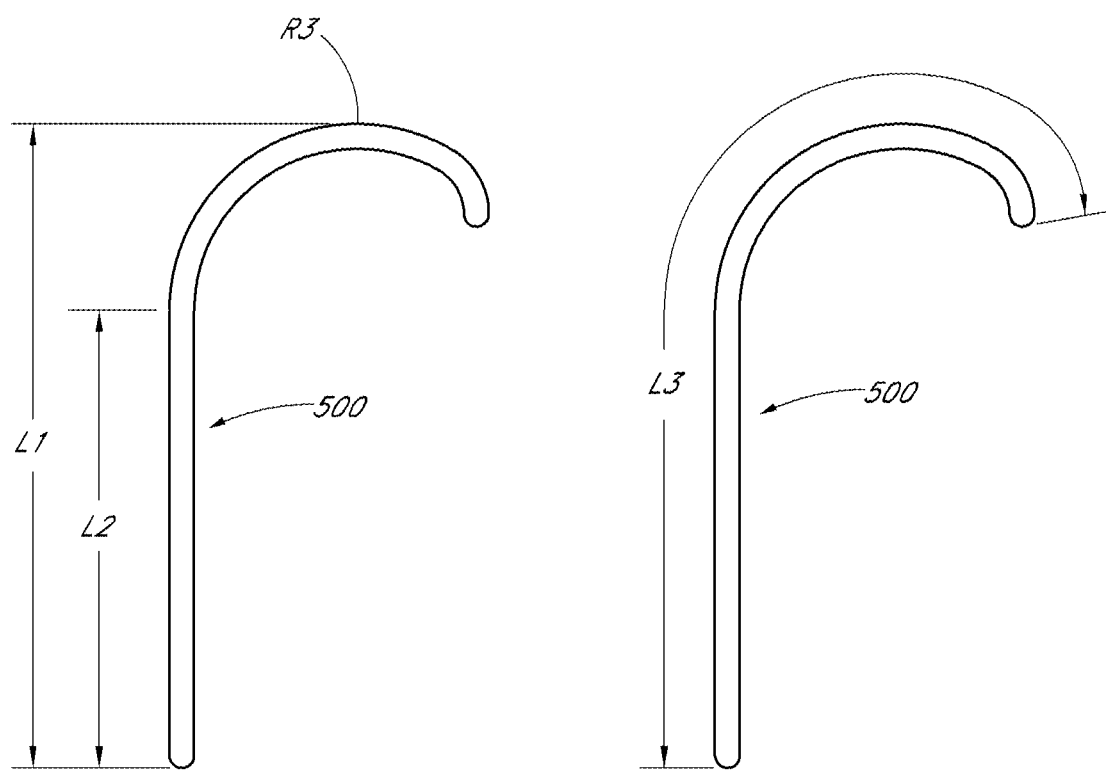
FIG. 13D
FIG. 13E

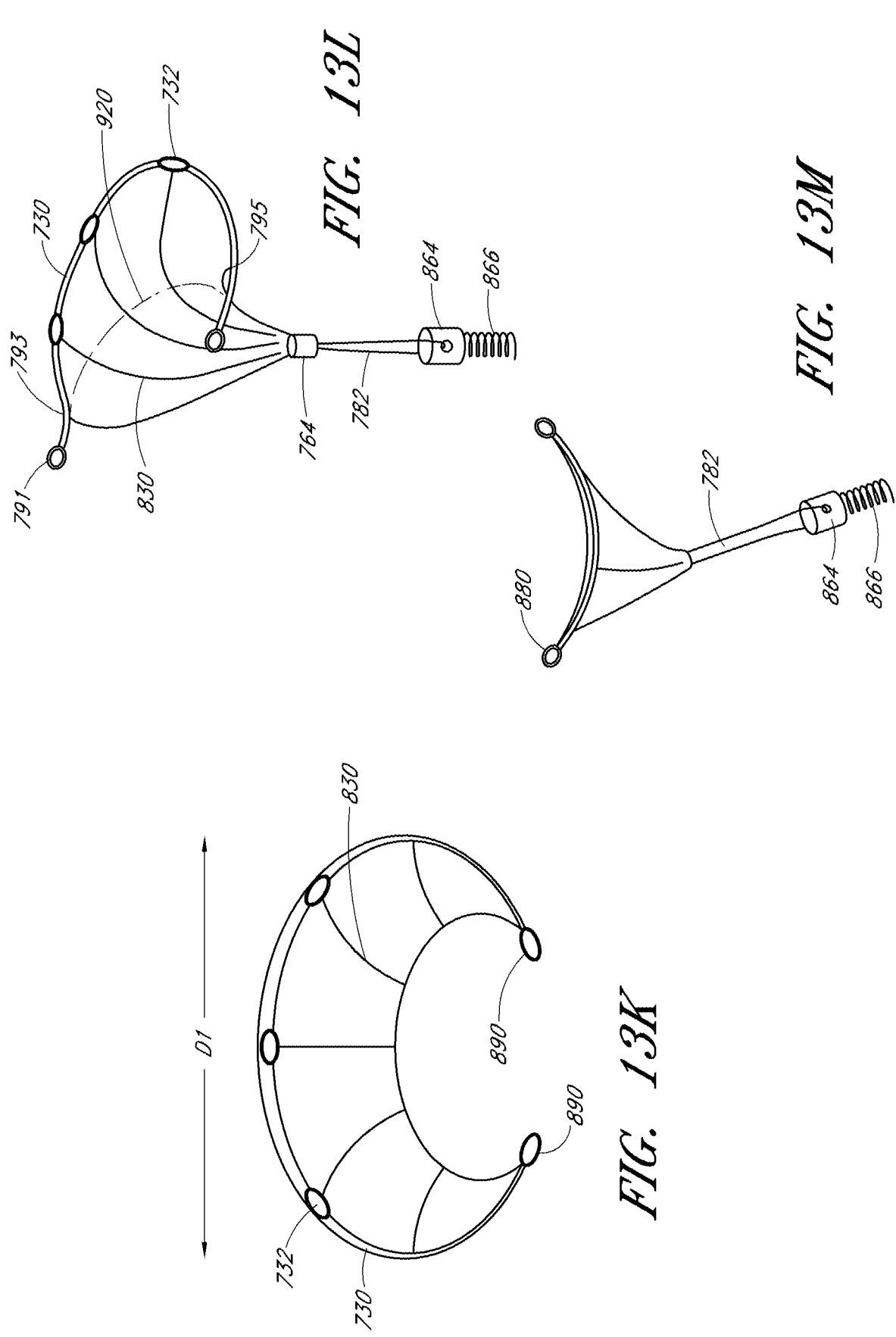

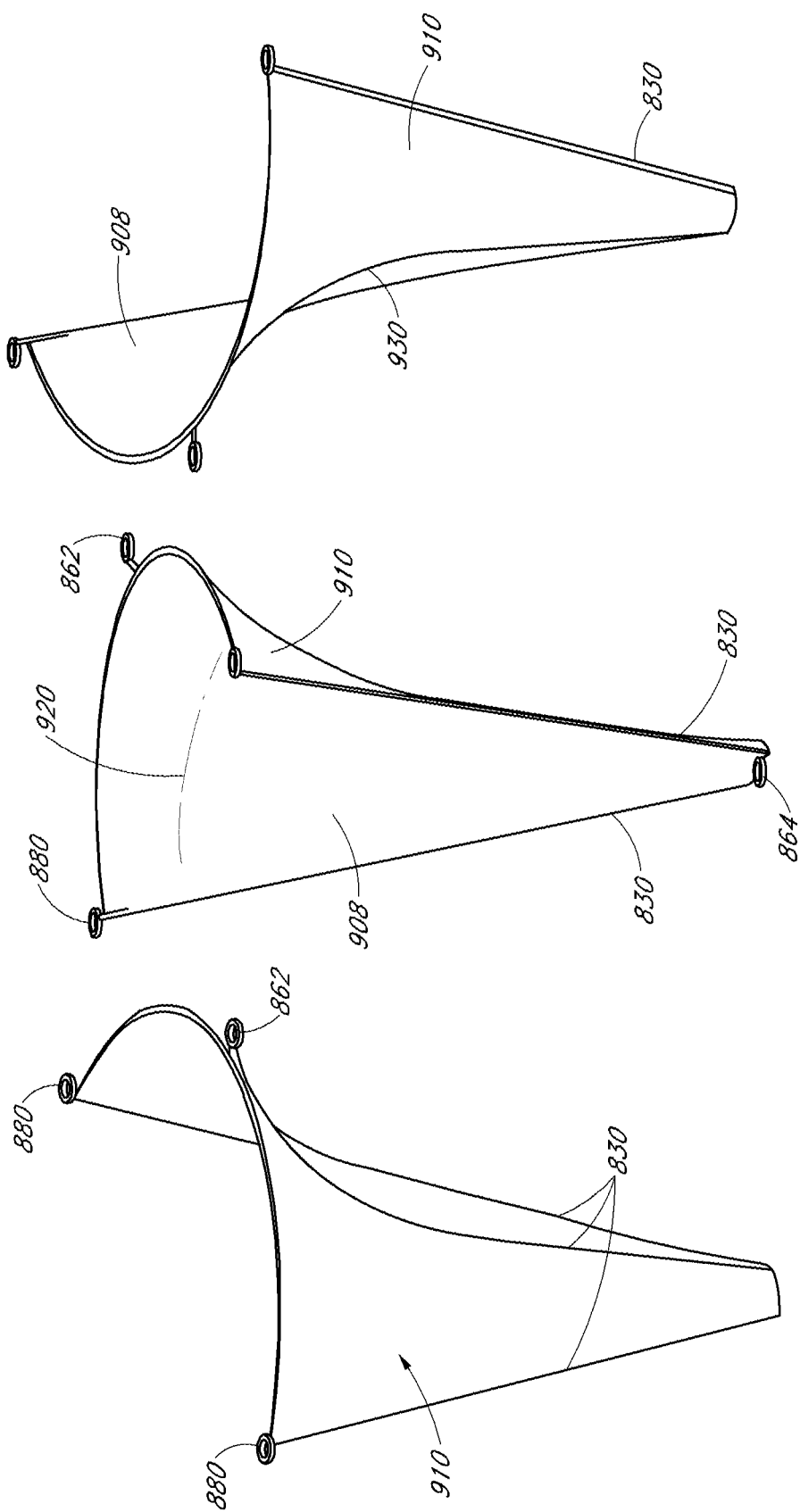

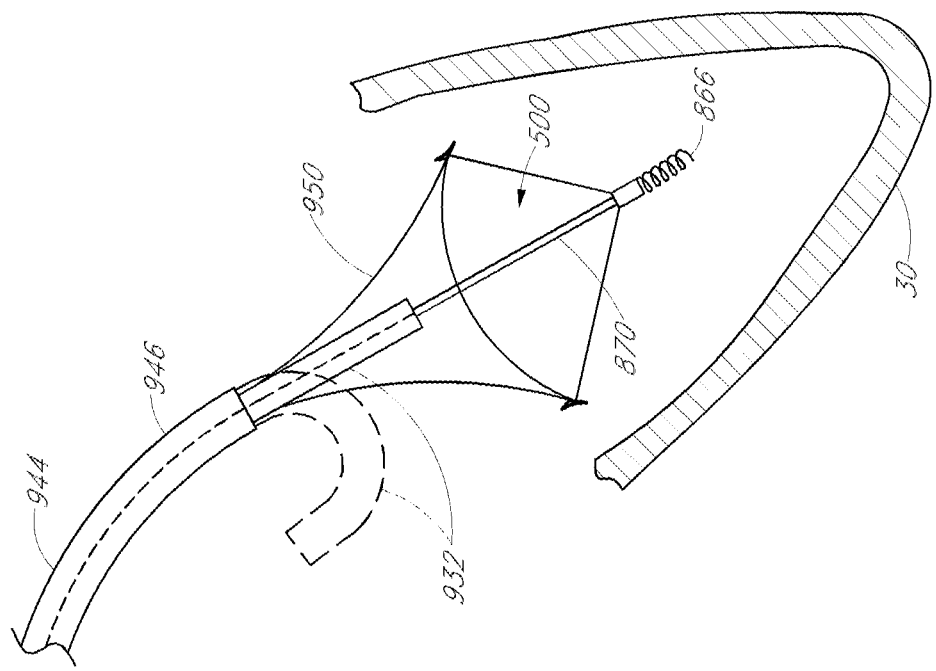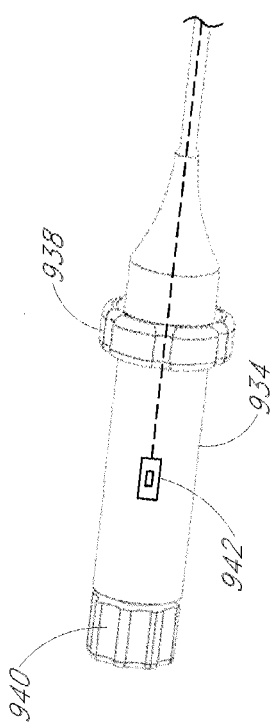
FIG. 16C

DEVICE, SYSTEM, AND METHOD FOR TRANSCATHETER TREATMENT OF VALVE REGURGITATION

CROSS-REFERENCE TO RELATED APPLICATIONS

The present application is a continuation of U.S. patent application Ser. No. 15/455,567 filed on Mar. 10, 2017, now U.S. Pat. No. 10,512,542, which is a continuation of U.S. patent application Ser. No. 14/542,091 filed on Nov. 14, 2014, now U.S. Pat. No. 9,592,118, which is a continuation of U.S. patent application Ser. No. 13/531,407 filed on Jun. 22, 2012, now U.S. Pat. No. 8,888,843, which is a continuation-in-part of U.S. patent application Ser. No. 13/099,532 filed on May 3, 2011, now U.S. Pat. No. 8,845,717, which claims priority under 35 U.S.C. § 119(e) to U.S. Provisional Application No. 61/437,397, filed on Jan. 28, 2011, the disclosures of which are incorporated by reference herein in their entirety and made a part of the present specification.

BACKGROUND OF THE INVENTION

Field of the Invention

The present invention generally provides improved medical devices, systems, and methods, typically for treatment of heart valve disease and/or for altering characteristics of one or more valves of the body. Embodiments of the invention include implants for treatment of mitral valve regurgitation.

The human heart receives blood from the organs and tissues via the veins, pumps that blood through the lungs where the blood becomes enriched with oxygen, and propels the oxygenated blood out of the heart to the arteries so that the organ systems of the body can extract the oxygen for proper function. Deoxygenated blood flows back to the heart where it is once again pumped to the lungs.

The heart includes four chambers: the right atrium (RA), the right ventricle (RV), the left atrium (LA) and the left ventricle (LV). The pumping action of the left and right sides of the heart occurs generally in synchrony during the overall cardiac cycle.

The heart has four valves generally configured to selectively transmit blood flow in the correct direction during the cardiac cycle. The valves that separate the atria from the ventricles are referred to as the atrioventricular (or AV) valves. The AV valve between the left atrium and the left ventricle is the mitral valve. The AV valve between the right atrium and the right ventricle is the tricuspid valve. The pulmonary valve directs blood flow to the pulmonary artery and thence to the lungs; blood returns to the left atrium via the pulmonary veins. The aortic valve directs flow through the aorta and thence to the periphery. There are normally no direct connections between the ventricles or between the atria.

The mechanical heartbeat is triggered by an electrical impulse which spreads throughout the cardiac tissue. Opening and closing of heart valves may occur primarily as a result of pressure differences between chambers, those pressures resulting from either passive filling or chamber contraction. For example, the opening and closing of the mitral valve may occur as a result of the pressure differences between the left atrium and the left ventricle.

At the beginning of ventricular filling (diastole) the aortic and pulmonary valves are closed to prevent back flow from the arteries into the ventricles. Shortly thereafter, the AV valves open to allow unimpeded flow from the atria into the corresponding ventricles. Shortly after ventricular systole (i.e., ventricular emptying) begins, the tricuspid and mitral valves normally shut, forming a seal which prevents flow from the ventricles back into the corresponding atria.

Unfortunately, the AV valves may become damaged or may otherwise fail to function properly, resulting in improper closing. The AV valves are complex structures that generally include an annulus, leaflets, chordae and a support structure. Each atrium interfaces with its valve via an atrial vestibule. The mitral valve has two leaflets; the analogous structure of the tricuspid valve has three leaflets, and apposition or engagement of corresponding surfaces of leaflets against each other helps provide closure or sealing of the valve to prevent blood flowing in the wrong direction. Failure of the leaflets to seal during ventricular systole is known as malcoaptation, and may allow blood to flow backward through the valve (regurgitation). Heart valve regurgitation can have serious consequences to a patient, often resulting in cardiac failure, decreased blood flow, lower blood pressure, and/or a diminished flow of oxygen to the tissues of the body. Mitral regurgitation can also cause blood to flow back from the left atrium to the pulmonary veins, causing congestion. Severe valvular regurgitation, if untreated, can result in permanent disability or death.

Description of the Related Art

A variety of therapies have been applied for treatment of mitral valve regurgitation, and still other therapies may have been proposed but not yet actually used to treat patients. While several of the known therapies have been found to provide benefits for at least some patients, still further options would be desirable. For example, pharmacologic agents (such as diuretics and vasodilators) can be used with patients having mild mitral valve regurgitation to help reduce the amount of blood flowing back into the left atrium. However, medications can suffer from lack of patient compliance. A significant number of patients may occasionally (or even regularly) fail to take medications, despite the potential seriousness of chronic and/or progressively deteriorating mitral valve regurgitation. Pharmacological therapies of mitral valve regurgitation may also be inconvenient, are often ineffective (especially as the condition worsens), and can be associated with significant side effects (such as low blood pressure).

A variety of surgical options have also been proposed and/or employed for treatment of mitral valve regurgitation. For example, open-heart surgery can replace or repair a dysfunctional mitral valve. In annuloplasty ring repair, the posterior mitral annulus can be reduced in size along its circumference, optionally using sutures passed through a mechanical surgical annuloplasty sewing ring to provide coaptation. Open surgery might also seek to reshape the leaflets and/or otherwise modify the support structure. Regardless, open mitral valve surgery is generally a very invasive treatment carried out with the patient under general anesthesia while on a heart-lung machine and with the chest cut open. Complications can be common, and in light of the morbidity (and potentially mortality) of open-heart surgery, the timing becomes a challenge—sicker patients may be in greater need of the surgery, but less able to withstand the surgery. Successful open mitral valve surgical outcomes can also be quite dependent on surgical skill and experience.

Given the morbidity and mortality of open-heart surgery, innovators have sought less invasive surgical therapies. Procedures that are done with robots or through endoscopes are often still quite invasive, and can also be time consuming, expensive, and in at least some cases, quite dependent on the surgeon's skill. Imposing even less trauma on these sometimes frail patients would be desirable, as would be providing therapies that could be successfully implemented by a significant number of physicians using widely distributed skills. Toward that end, a number of purportedly less invasive technologies and approaches have been proposed. These include devices which seek to re-shape the mitral annulus from within the coronary sinus; devices that attempt to reshape the annulus by cinching either above to below the native annulus; devices to fuse the leaflets (imitating the Alfieri stitch); devices to re-shape the left ventricle, and the like.

Perhaps most widely known, a variety of mitral valve replacement implants have been developed, with these implants generally replacing (or displacing) the native leaflets and relying on surgically implanted structures to control the blood flow paths between the chambers of the heart. While these various approaches and tools have met with differing levels of acceptance, none has yet gained widespread recognition as an ideal therapy for most or all patients suffering from mitral valve regurgitation.

Because of the challenges and disadvantages of known minimally invasive mitral valve regurgitation therapies and implants, still further alternative treatments have been proposed. Some of the alternative proposals have called for an implanted structure to remain within the valve annulus throughout the heart beat cycle. One group of these proposals includes a cylindrical balloon or the like to remain implanted on a tether or rigid rod extending between the atrium and the ventricle through the valve opening. Another group relies on an arcuate ring structure or the like, often in combination with a buttress or structural cross-member extending across the valve so as to anchor the implant. Unfortunately, sealing between the native leaflets and the full perimeter of a balloon or other coaxial body may prove challenging, while the significant contraction around the native valve annulus during each heart beat may result in significant fatigue failure issues during long-term implantation if a buttress or anchor interconnecting cross member is allowed to flex. Moreover, the significant movement of the tissues of the valve may make accurate positioning of the implant challenging regardless of whether the implant is rigid or flexible.

In light of the above, it would be desirable to provide improved medical devices, systems, and methods. It would be particularly desirable to provide new techniques for treatment of mitral valve regurgitation and other heart valve diseases, and/or for altering characteristics of one or more of the other valves of the body. The need remains for a device which can directly enhance leaflet coaptation (rather than indirectly via annular or ventricular re-shaping) and which does not disrupt leaflet anatomy via fusion or otherwise, but which can be deployed simply and reliably, and without excessive cost or surgical time. It would be particularly beneficial if these new techniques could be implemented using a less-invasive approach, without stopping the heart or relying on a heart-lung machine for deployment, and without relying on exceptional skills of the surgeon to provide improved valve and/or heart function.

SUMMARY OF THE INVENTION

The invention generally provides improved medical devices, systems, and methods. In some embodiments, the invention provides new implants, implant systems, and methods for treatment of mitral valve regurgitation and other valve diseases. The implants will generally include a coaptation assist body which remains within the blood flow path as the valve moves back and forth between an open-valve configuration and a closed valve configuration. The coaptation assist bodies or valve bodies may be relatively thin, elongate (along the blood flow path), and/or conformable structures which extend laterally across some, most, or all of the width of the valve opening, allowing coaptation between at least one of the native leaflets and the implant body.

In some embodiments, an implant for treating mal-coaptation of a heart valve, the heart valve having an annulus and first and second leaflets with an open configuration and a closed configuration, is provided, the implant comprising a coaptation assist body having an first coaptation surface, an opposed second surface, each surface bounded by a first lateral edge, a second lateral edge, an inferior edge, wherein the inferior edge has a length less than 10 mm, and a superior edge, the superior edge further comprising an annular curve radius, wherein the annular curve radius is concave toward the first coaptation surface and has a length in the range of 25-35 mm, and wherein the element arc length along the coaptation surface of the coaptation assist body between the superior edge and the inferior edge is in the range of 50-60 mm, a first anchor selectively deployable at a first target location of the heart near the midpoint position of the second leaflet on the annulus and couplable to the coaptation assist body near the midpoint of the superior edge curve, and a second anchor selectively deployable, independently of the deployment of the first anchor, at a second location of the heart in the ventricle such that the coaptation assist body, when coupled to both the first anchor and the second anchor, extends from the first target location across the valve to the second target location.

In some embodiments, the first coaptation surface of the implant coapts with the first leaflet of the valve in its closed configuration. In some embodiments, coaptation between the first coaptation surface and the first leaflet of the valve occurs around the level of the valve.

In some embodiments, the first anchor of the implant is deployable superior to the annulus. In some embodiments, the first anchor is deployable into a wall of an atrium. In other embodiments, the first anchor is deployable into a wall of an auricle.

In some embodiments, a coaptation assist body for treating mal-coaptation of a heart valve, the heart valve having an annulus which defines a valve plane, and at least a first and a second leaflet, is provided, the coaptation assist body comprising a first coaptation surface and an opposed second surface, a first lateral edge, a second lateral edge, an inferior edge, and a superior edge, a coaptation zone on the first coaptation surface extending transversely between the inferior edge and the superior edge configured such that a leaflet of the valve may coapt against the coaptation zone, wherein the first coaptation surface has an overall element arc length from the superior edge to the inferior edge in the range of 50-60 mm, and wherein the first coaptation surface generally conforms to a portion of a surface of a cone between the inferior edge and the coaptation zone, and wherein the first coaptation surface comprises a radially outward flare beginning at an inflection point within a range of 30-40 mm from the inferior edge of the coaptation assist body along a longitudinal axis of the cone, wherein the radially outward flare has a radius in the range of 5-12 mm.

Some embodiments provide a coaptation assist body for treating mal-coaptation of a heart valve, the heart valve having an annulus and first and second leaflets with a first commissure at a first junction of the first and second leaflets and a second commissure at a second junction of the first and second leaflets, the coaptation assist body comprising a first coaptation surface and an opposed second surface, a first lateral edge, a second lateral edge, an inferior edge, and a superior edge, wherein the superior edge comprises a curve with a length in the range of 25-35 mm, such that the distance between the lateral margins of the superior curve is equivalent to the distance between the first commissure and the second commissure, a coaptation element length measured perpendicular to a valve plane defined by the annulus of the valve between a most proximal extent of the coaptation assist body and the inferior edge of the coaptation assist body, wherein the coaptation element length is in the range of 35-45 mm, a ventricular element length measured perpendicular to the valve plane between the level of the annulus and the inferior edge of the coaptation assist body, wherein the ventricular element length is in the range of 25-35 mm, and a coaptation zone between the superior edge and inferior edge, wherein the coaptation zone has a coaptation zone curve radius measured between the lateral edges of the coaptation assist body generally parallel to the valve plane at the general level of the heart valve, wherein the coaptation zone curve radius is in the range of 35-45 mm.

In some embodiments, the coaptation assist body further comprises a first connection element near the midpoint of the superior edge coupleable with a first anchor for deployment in a heart structure. Some embodiments further comprise a second connection element at the inferior edge coupleable with a second anchor for deployment in a heart structure of the ventricle.

In some embodiments, the anterior surface and posterior surface of the coaptation assist body further comprise a covering comprised of ePTFE, polyurethane foam, polycarbonate foam, biologic tissue such as porcine pericardium, or silicone.

In some embodiments, at least one strut is disposed within the covering material for maintenance of a shape of the coaptation assist body. In some embodiments, at least one strut is connected to the second connection element and extends toward the superior edge of the implant. In some embodiments, the strut is composed of Nitinol, polypropylene, stainless steel, or any other suitable material. In some embodiments, a first strut extends from the second connection near one lateral edge to the superior edge and a second strut extends from the second connection near the second lateral edge to the superior edge of the implant such that the struts assist in maintaining the distance between the lateral margins of the superior edge Methods are provided for treating mal-coaptation of a heart valve in a patient, the heart valve having an annulus and first and second leaflets, the first and second leaflets each comprising a proximal surface, a distal surface, a coaptation edge and an annular edge; the annulus further defining a valve plane, the valve plane separating an atrium proximally and a ventricle distally. Some methods comprise selectively deploying a first anchor into heart tissue distal to the annulus, selectively deploying a second anchor proximal to the annulus near a mid-point of the annular edge of the second leaflet, and coupling the first anchor and the second anchor to a coaptation assist body comprising a coaptation surface and a leaflet surface such that the coaptation assist body is suspended across the valve plane from the atrium proximally to the ventricle distally.

In some methods, the coaptation assist body is suspended such that the coaptation surface coapts with the first leaflet and the leaflet surface of the coaptation assist body overlays the second leaflet such that mal-coaptation is mitigated.

BRIEF DESCRIPTION OF THE DRAWINGS

FIG. 4A illustrates a stylized cross section of a heart, showing mitral valve mal-coaptation in the settings of functional mitral valve regurgitation. FIG. 4B illustrates a stylized cross section of a heart, showing mitral valve mal-coaptation in the settings of degenerative mitral valve regurgitation.

FIGS. 5A-5F illustrate embodiments of an implant deployed within the mitral valves of 4A and 4B so as to mitigate the mal-coaptation by establishing a new coaptation point.

FIGS. 8A-8B show an embodiment of the coaptation enhancement element.

FIG. 10A schematically illustrates an embodiment of a coaptation enhancement element; FIG. 10B schematically illustrates an embodiment of the support structure and anchor attachments of a coaptation enhancement element; FIG. 10C schematically illustrates a lateral view of an embodiment of the coaptation element implanted across a mitral valve.

FIG. 10D schematically illustrates an embodiment of a coaptation element with proximal support structure; FIG. 10E schematically illustrates another embodiment of a coaptation element with proximal support structure.

FIG. 13C illustrates a perspective view of an embodiment of the coaptation element.

FIGS. 13D-E illustrate side views of an embodiment of the coaptation element.

FIGS. 13K-M illustrate an end view and oblique views of embodiments of the coaptation element with annular reinforcement ring.

FIG. 14A-14C schematically illustrate features of an embodiment of the coaptation enhancement element.

FIG. 16C schematically illustrates an embodiment of a delivery system for a transcatheter technique.

FIG. 18A-18C schematically illustrates an embodiment of a helical anchor with protective boot.

DETAILED DESCRIPTION

Figure 1A:
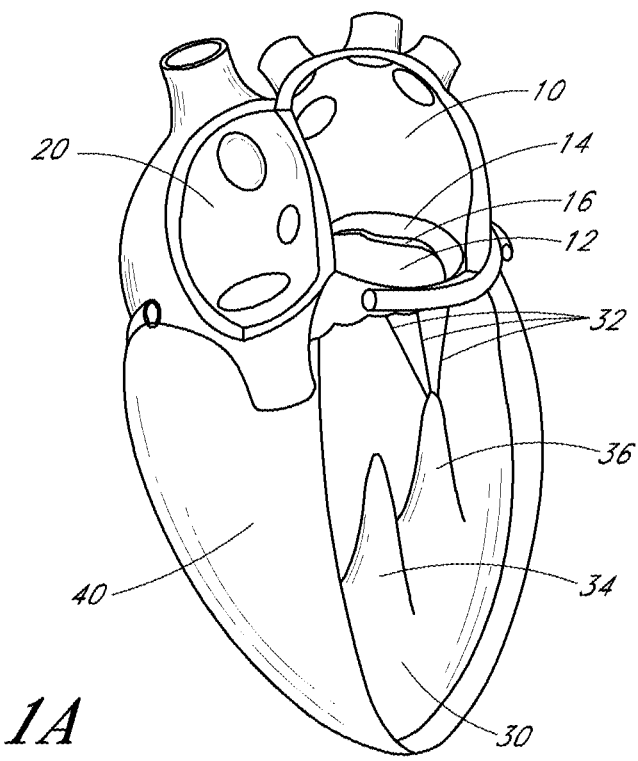
FIG. 1A-1F schematically illustrate some of the tissues of the heart and mitral valve, as described in the Background section and below, and which may interact with the implants and systems described herein.
Figure 1B:
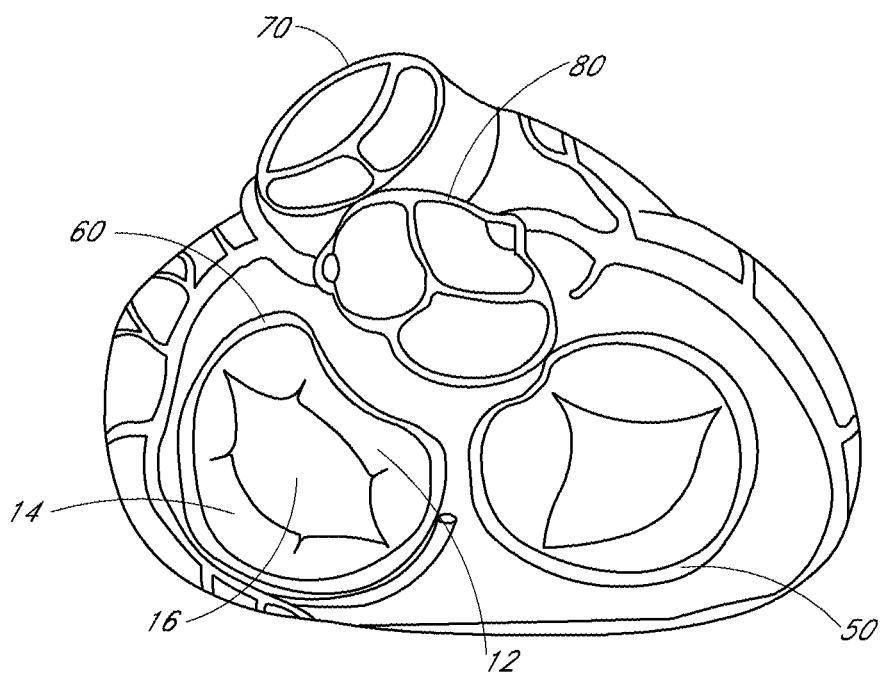
Figure 1C:
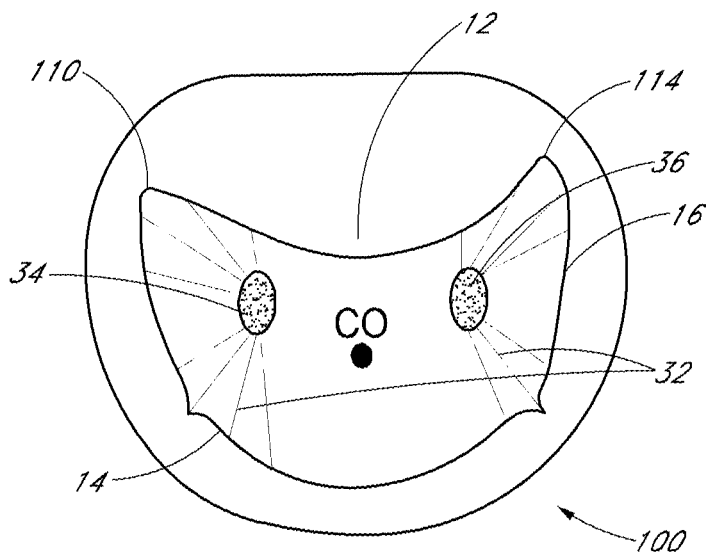
Figure 1D:
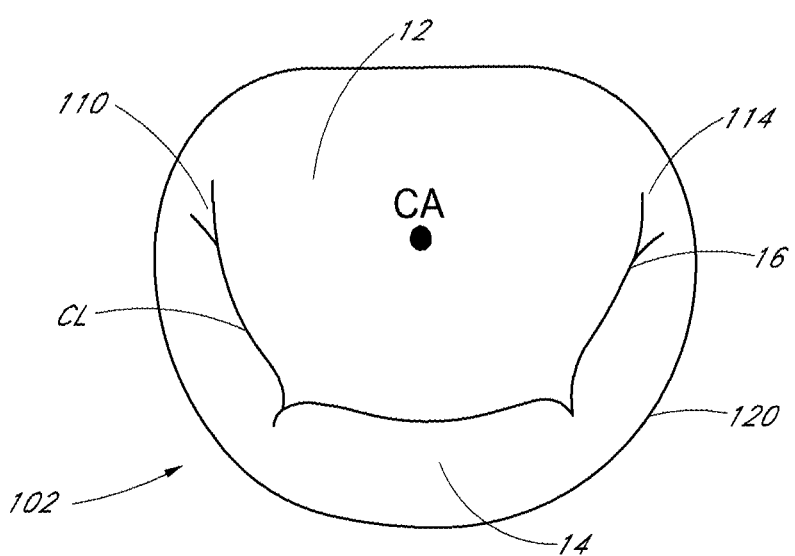

The present invention generally provides improved medical devices, systems, and methods, often for treatment of mitral valve regurgitation and other valve diseases including tricuspid regurgitation. While the description that follows includes reference to the anterior leaflet in a valve with two leaflets such as the mitral valve, it is understand that "anterior leaflet" could refer to one or more leaflets in valve with multiple leaflets. For example, the tricuspid valve has 3 leaflets so the "anterior" could refer to one or two of the medial, lateral, and posterior leaflets. The implants described herein will generally include a coaptation assist body (sometimes referred to herein as a valve body) which is generally along the blood flow path as the leaflets of the valve move back and forth between an open-valve configuration (with the anterior leaflet separated from valve body) and a closed-valve configuration (with the anterior leaflet engaging opposed surfaces of the valve body). The valve body will be disposed between the native leaflets to close the gap caused by mal-coaptation of the native leaflets by providing a surface for at least one of the native leaflets to coapt against, while effectively replacing a second native leaflet in the area of the valve which, were it functioning normally, it would occlude during systole. The gaps may be lateral (such as may be caused by a dilated left ventricle and/or mitral valve annulus) and/or axial (such as where one leaflet prolapses or is pushed by fluid pressure beyond the annulus when the valve should close).

Among other uses, the coaptation assistance devices, implants, and methods described herein may be configured for treating functional and/or degenerative mitral valve regurgitation (MR) by creating an artificial coaptation zone within which at least one of the native mitral valve leaflets can seal. The structures and methods herein will largely be tailored to this application, though alternative embodiments might be configured for use in other valves of the heart and/or body, including the tricuspid valve, valves of the peripheral vasculature, the inferior vena cava, or the like.

Referring to FIGS. 1A-1D, the four chambers of the heart are shown, the left atrium 10, right atrium 20, left ventricle 30, and right ventricle 40. The mitral valve 60 is disposed between the left atrium 10 and left ventricle 30. Also shown are the tricuspid valve 50 which separates the right atrium 20 and right ventricle 40, the aortic valve 80, and the pulmonary valve 70. The mitral valve 60 is composed of two leaflets, the anterior leaflet 12 and posterior leaflet 14. In a healthy heart, the edges of the two leaflets appose during systole at the coaptation zone 16.

Figure 1E:
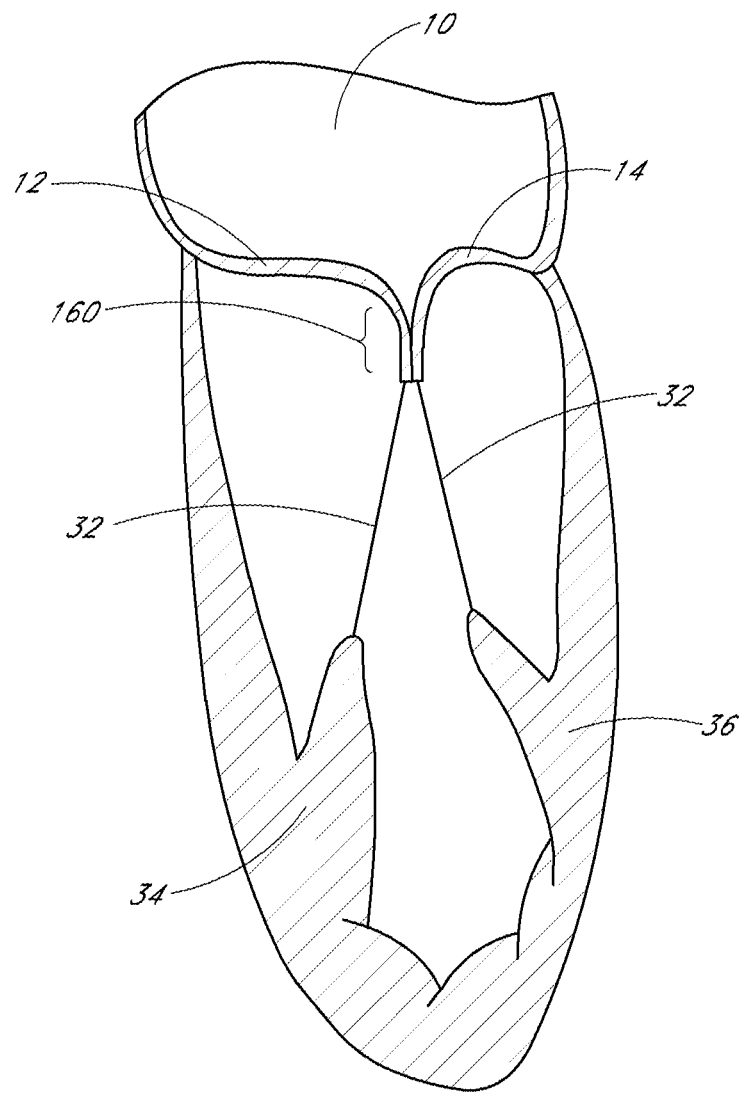

The fibrous annulus 120, part of the cardiac skeleton, provides attachment for the two leaflets of the mitral valve, referred to as the anterior leaflet 12 and the posterior leaflet 14. The leaflets are axially supported by attachment to the chordae tendineae 32. The chordae, in turn, attach to one or both of the papillary muscles 34, 36 of the left ventricle. In a healthy heart, the chordae support structures tether the mitral valve leaflets, allowing the leaflets to open easily during diastole but to resist the high pressure developed during ventricular systole. In addition to the tethering effect of the support structure, the shape and tissue consistency of the leaflets helps promote an effective seal or coaptation. The leading edges of the anterior and posterior leaflet come together along a funnel-shaped zone of coaptation 16, with a lateral cross-section 160 of the three-dimensional coaptation zone (CZ) being shown schematically in FIG. 1E.

Figure 1F:
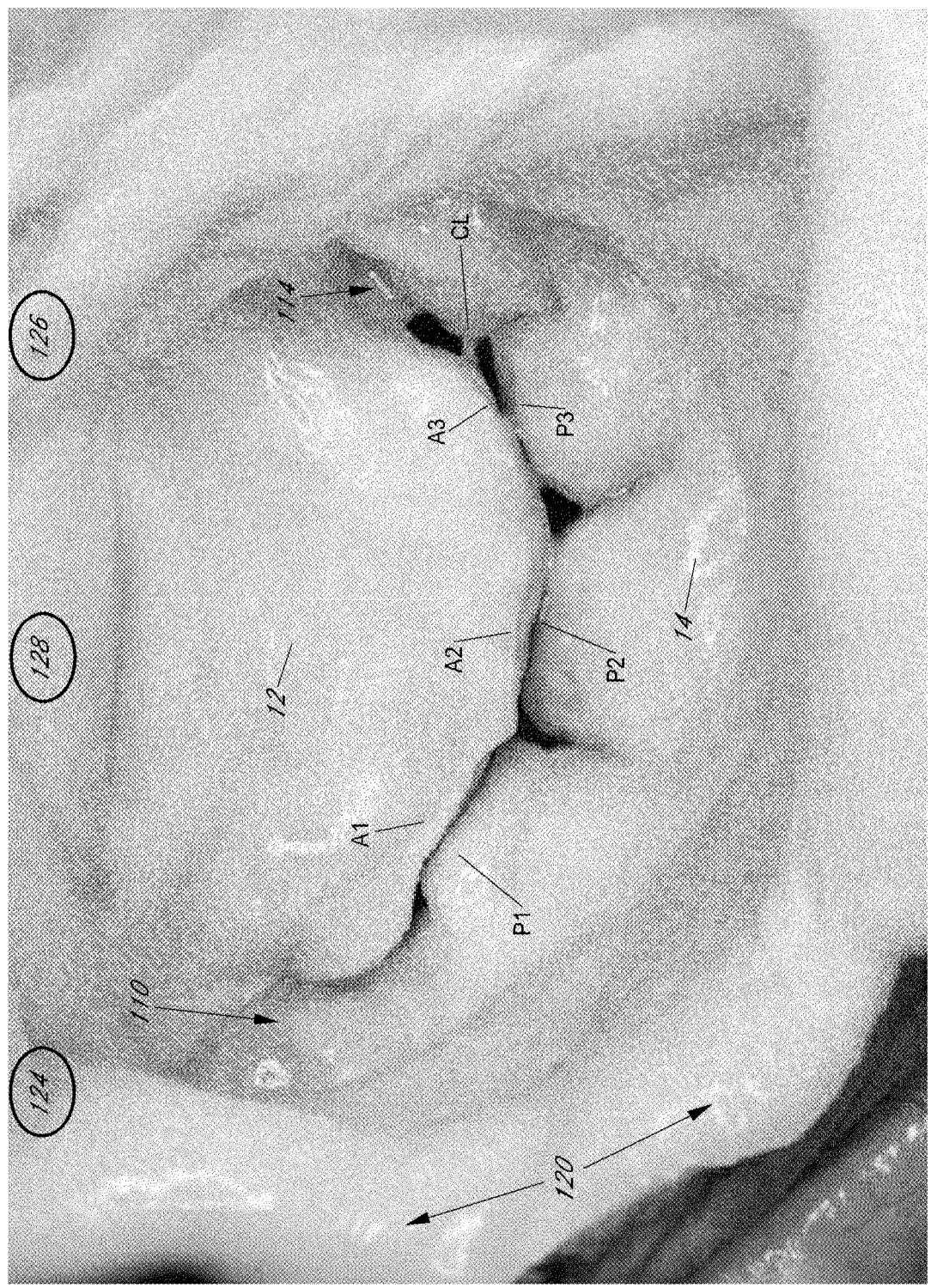

The anterior and posterior mitral leaflets are dissimilarly shaped. The anterior leaflet is more firmly attached to the annulus overlying the central fibrous body (cardiac skeleton), and is somewhat stiffer than the posterior leaflet, which is attached to the more mobile posterior mitral annulus. Approximately 80 percent of the closing area is the anterior leaflet. Adjacent to the commissures 110, 114, on or anterior to the annulus 120, lie the left (lateral) 124 and right (septal) 126 fibrous trigones which are formed where the mitral annulus is fused with the base of the non-coronary cusp of the aorta (FIG. 1F). The fibrous trigones 124, 126 form the septal and lateral extents of the central fibrous body 128. The fibrous trigones 124, 126 may have an advantage, in some embodiments, as providing a firm zone for stable engagement with one or more annular or atrial anchors. The coaptation zone CL between the leaflets 12, 14 is not a simple line, but rather a curved funnel-shaped surface interface. The first 110 (lateral or left) and second 114 (septal or right) commissures are where the anterior leaflet 12 meets the posterior leaflet 14 at the annulus 120. As seen most clearly in the axial views from the atrium of FIGS. 1C, 1D, and 1F, an axial cross-section of the coaptation zone generally shows the curved line CL that is separated from a centroid of the annulus CA as well as from the opening through the valve during diastole CO. In addition, the leaflet edges are scalloped, more so for the posterior versus the anterior leaflet. Mal-coaptation can occur between one or more of these A-P (anterior-posterior) segment pairs A1/P1, A2/P2, and A3/P3, so that mal-coaptation characteristics may vary along the curve of the coaptation zone CL.

Figure 2B:
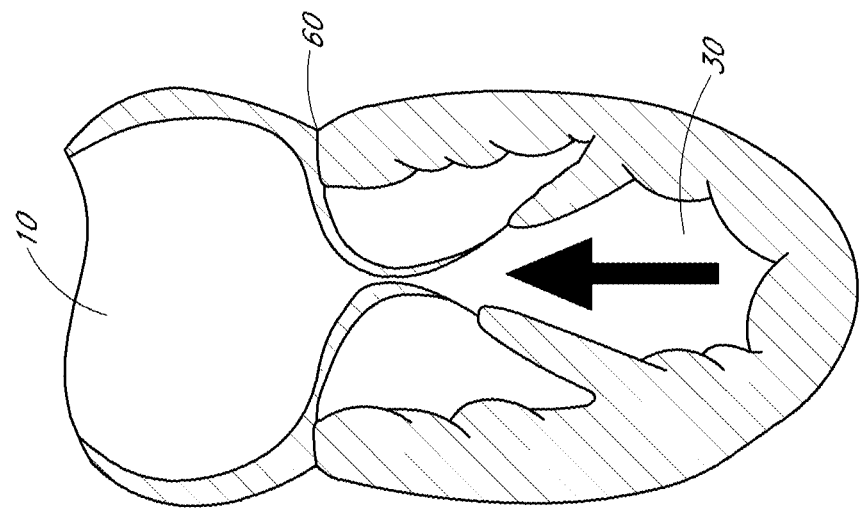
FIG. 2B illustrates a simplified cross-section of a heart, schematically showing mitral valve function during systole.
Figure 2A:
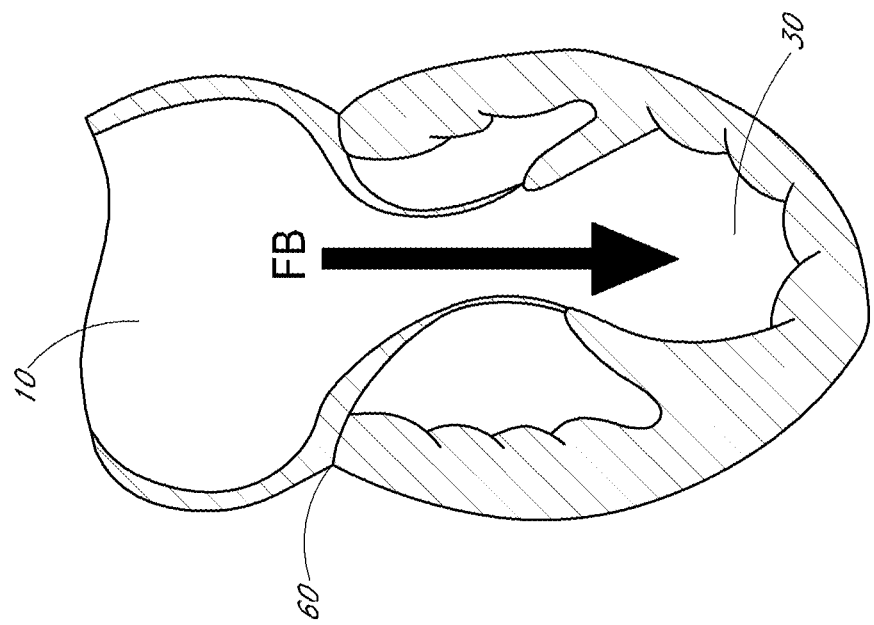
FIG. 2A illustrates a simplified cross-section of a heart, schematically showing mitral valve function during diastole.

Referring now to FIG. 2A, a properly functioning mitral valve 60 of a heart is open during diastole to allow blood to flow along a flow path FP from the left atrium toward the left ventricle 30 and thereby fill the left ventricle. As shown in FIG. 2B, the functioning mitral valve 60 closes and effectively seals the left ventricle 30 from the left atrium 10 during systole, first passively then actively by increase in ventricular pressure, thereby allowing contraction of the heart tissue surrounding the left ventricle to advance blood throughout the vasculature.

Referring to FIGS. 3A-3B and 4A-4B, there are several conditions or disease states in which the leaflet edges of the mitral valve fail to appose sufficiently and thereby allow blood to regurgitate in systole from the ventricle into the atrium. Regardless of the specific etiology of a particular patient, failure of the leaflets to seal during ventricular systole is known as mal-coaptation and gives rise to mitral regurgitation.

Figure 3A:
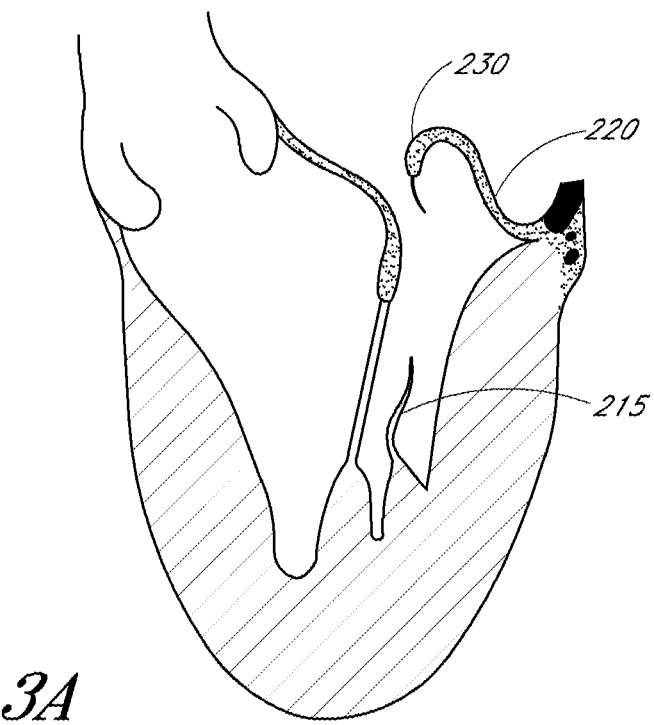
FIGS. 3A-3B illustrate a simplified cross-section of a heart, schematically showing mitral valve regurgitation during systole in the setting of mal-coaptation of the mitral valve leaflets.

Generally, mal-coaptation can result from either excessive tethering by the support structures of one or both leaflets, or from excessive stretching or tearing of the support structures. Other, less common causes include infection of the heart valve, congenital abnormalities, and trauma. Valve malfunction can result from the chordae tendineae becoming stretched, known as mitral valve prolapse, and in some cases tearing of the chordae 215 or papillary muscle, known as a flail leaflet 220, as shown in FIG. 3A. Or if the leaflet tissue itself is redundant, the valves may prolapse so that the level of coaptation occurs higher into the atrium, opening the valve higher in the atrium during ventricular systole 230. Either one of the leaflets can undergo prolapse or become flail. This condition is sometimes known as degenerative mitral valve regurgitation.

Figure 3B:
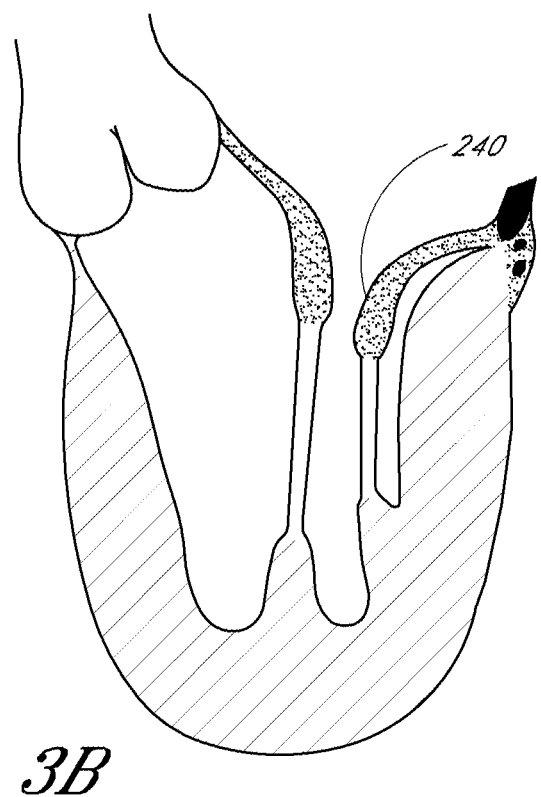

In excessive tethering, as shown in FIG. 3B, the leaflets of a normally structured valve may not function properly because of enlargement of or shape change in the valve annulus: so-called annular dilation 240. Such functional mitral regurgitation generally results from heart muscle failure and concomitant ventricular dilation. And the excessive volume load resulting from functional mitral regurgitation can itself exacerbate heart failure, ventricular and annular dilation, thus worsening mitral regurgitation.

FIG. 4A-4B illustrate the backflow BF of blood during systole in functional mitral valve regurgitation (FIG. 4A) and degenerative mitral valve regurgitation (FIG. 4B). The increased size of the annulus in FIG. 4A, coupled with increased tethering due to hypertrophy of the ventricle 320 and papillary muscle 330, prevents the anterior leaflet 312 and posterior leaflet 314 from apposing, thereby preventing coaptation. In FIG. 4B, the tearing of the chordae 215 causes prolapse of the posterior leaflet 344 upward into the left atrium, which prevents apposition against the anterior leaflet 342. In either situation, the result is backflow of blood into the atrium, which decreases the effectiveness of left ventricle compression.

Figure 5B:
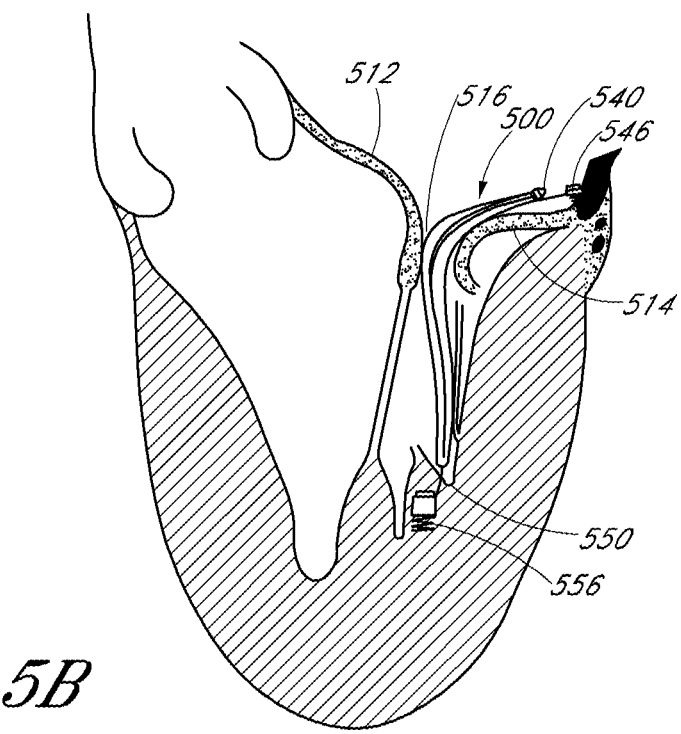
Figure 5A:
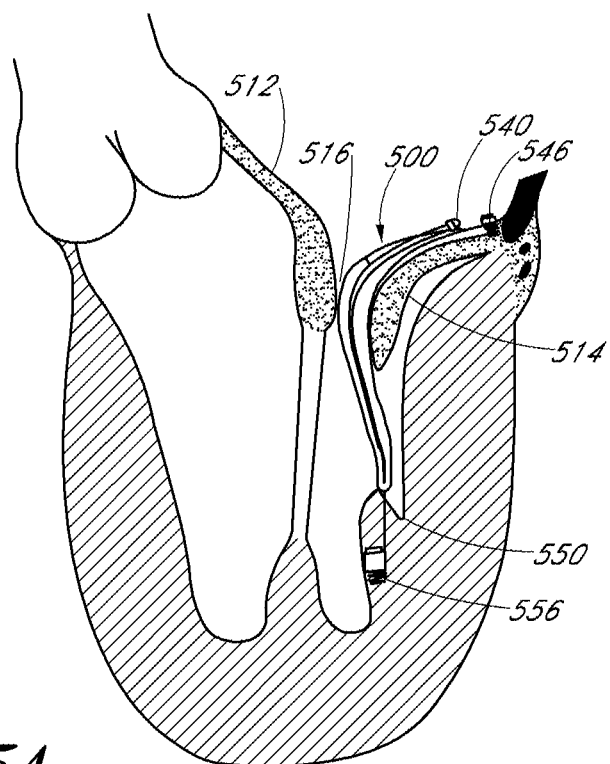
Figures 6A, 6B:
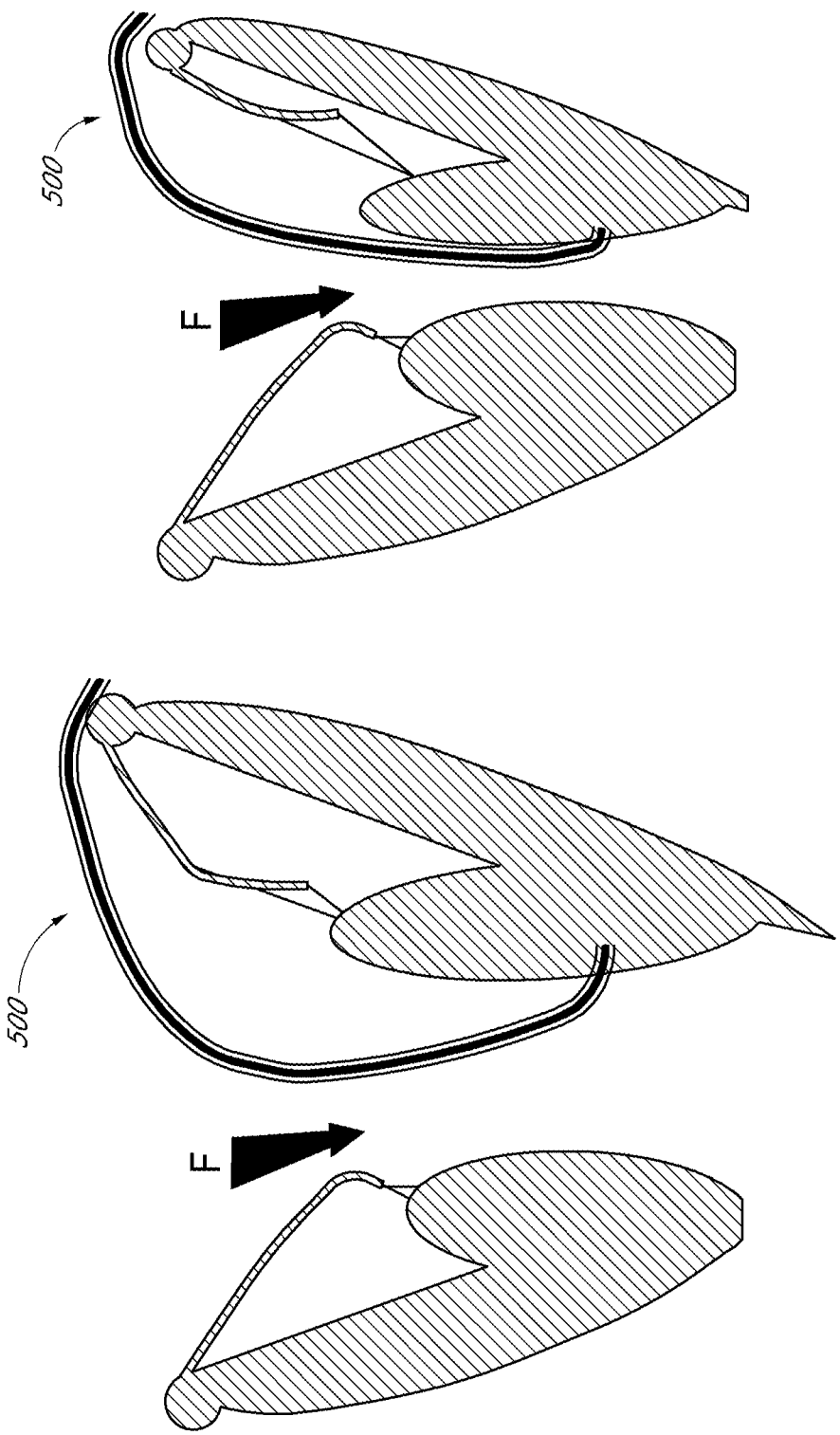
FIGS. 6A-6B illustrate the implants of 5A and 5B respectively during diastole, allowing free blood flow between the atrium and ventricle.

Referring now to FIG. 5A-5B, an embodiment of a coaptation enhancement element 500 can be seen in functional (FIG. 5A) and degenerative (FIG. 5B) mitral valve regurgitation. The element may be deployed in this embodiment so that it overlies the posterior leaflet 514, the chordae and papillary muscle. In this embodiment, the element attaches superiorly to the posterior aspect of the annulus 540 and inferiorly to the posterior aspect of the left ventricle 550 via annular anchor 546 and ventricular anchor 556. In other embodiments, more than one annular anchor and/or more than one ventricular anchor may be used to attach the coaptation enhancement element. In some elements, the one or more annular anchors may be replaced by or supplemented with one or more atrial or auricular anchors. The coaptation element may attach to the superior surface of the posterior annulus, the posterior atrial wall, or the annulus itself. A coaptation zone 516 has been established between the implant 500 and the native anterior leaflet 512. Similar implants can be used in both functional and degenerative mitral valve regurgitation because the failure of leaflet coaptation occurs in both, regardless of the mechanism behind the dysfunction. Therefore, as seen in FIGS. 5C-5D, different sized coaptation enhancement elements can be placed such that the native anterior leaflet 512 apposes the coaptation element at the appropriately established coaptation point 510, blocking flow F of blood during contraction of the ventricle. In order to accomplish this, a variety of sizes of implants are provided, with differing dimensions configured to fit varying anatomies. For example, there may be an implant height 530, which measures from the superior annular attachment site 540 to the inferior ventricular attachment site 550 in a plane basically perpendicular to the plane defined by the annulus of the valve, an implant depth 520 between the coaptation point 510 and the superior attachment site 540, and an implant projection 560 between the posterior wall at the level of the coaptation point and the coaptation point. As seen in the axial views of FIGS. 5E-5F, there is also a medial-lateral diameter 570 of the coaptation enhancement element, typically larger in functional MR. As seen in FIGS. 6A-B, during diastole, the implant 500 may stay in substantially the same position, while movement of the native anterior leaflet opens the valve, permitting flow F of blood from the left atrium to the left ventricle with minimal restriction. In some embodiments, the surface of the implant 500 may balloon or stretch upwards during ventricular systole, while the anchors remain unmoved. This may be advantageous as enhancing the seal between the anterior or coaptation surface of the element and the native leaflet at the coaptation zone during systole. During diastole, the surface may return to an initial position in which it lies more distally. This may provide an improved blood flow path between the atrium and ventricle during diastole, improving outflow from the atrium past the coaptation assist element.

Figure 7C:
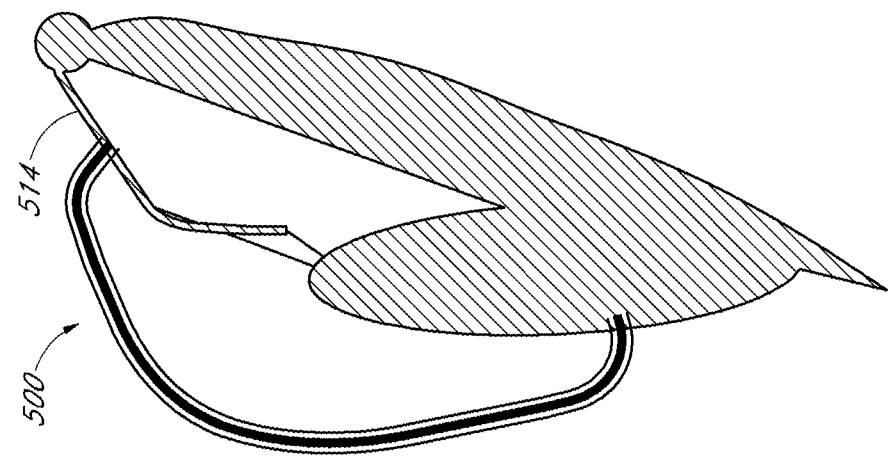
FIGS. 7A-7C illustrate alternative configurations of coaptation element attachment to cardiac structures.
Figure 7B:
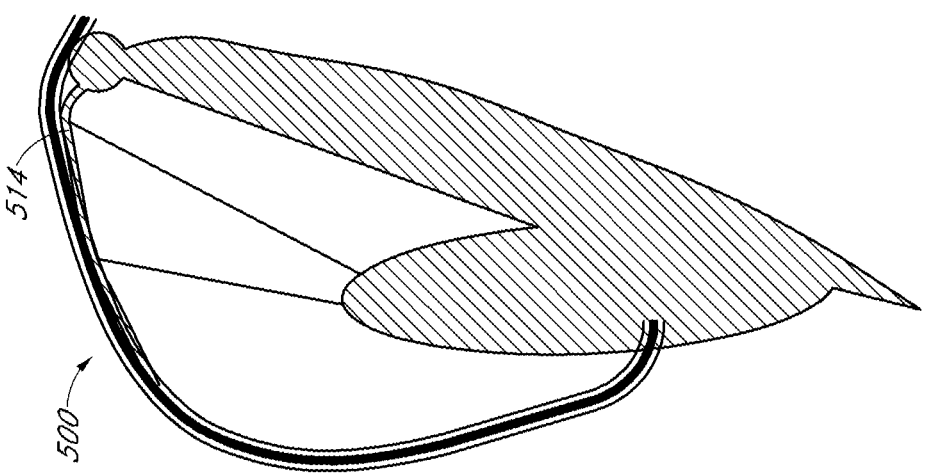
Figure 7A:
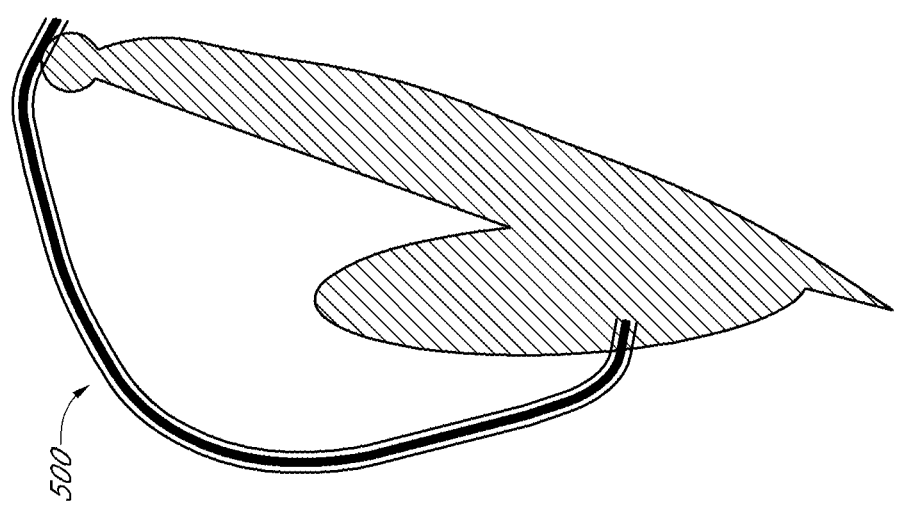

FIGS. 5 and 6 illustrate one embodiment of the coaptation enhancement element, in which the native posterior leaflet is left in position, and the implant is attached superiorly to the posterior annulus or adjacent atrial wall. Many possible alternate embodiments may have differing attachment mechanisms. For example, in FIG. 7A, the posterior leaflet is not present, having been removed surgically or the result of disease. In FIG. 7B, the native leaflet attaches to the posterior surface of the coaptation body. In FIG. 7C, the coaptation element may attach to the anterior surface of the posterior leaflet 514, rather than the annulus or atrial wall. These are some examples of variations, but still others are contemplated. For example, an anchoring structure (not shown) could pass from the coaptation element, through the atrial wall into the coronary sinus, wherein the anchoring structure attaches to a mating structure in the coronary sinus. Or the anchoring structure, which could be a mechanical structure or a simple suture, can pass through the atrial wall and be anchored by a knot or mechanical element, such as a clip, on the epicardial surface of the heart. Similarly, attachment inferiorly may be to the ventricular muscle, through the apex into the epicardium or pericardium and secured from outside, or at other attachment sites using alternative attachment means.

The deployed coaptation assist implant described herein may exhibit a number of desirable characteristics. Some embodiments need not rely on reshaping of the mitral annulus (such as by thermal shrinking of annular tissue, implantation of an annular ring prosthesis, and/or placement of a cinching mechanism either above or beneath the valve plane, or in the coronary sinus or related blood vessels). Advantageously, they also need not disrupt the leaflet structure or rely on locking together or fusing of the mitral leaflets. Many embodiments can avoid reliance on ventricular reshaping, and after implantation represent passive implanted devices with limited excursion which may result in very long fatigue life. Thus, the implant can be secured across a posterior leaflet while otherwise leaving native heart (e.g., ventricular, mitral annulus, etc) anatomy intact.

Mitigation of mitral valve mal-coaptation may be effective irrespective of which leaflet segment(s) exhibit mal-coaptation. The treatments described herein will make use of implants that are repositionable during the procedure, and even removable after complete deployment and/or tissue response begins or is completed, often without damaging the valve structure. Nonetheless, the implants described herein may be combined with one or more therapies that do rely on one or more of the attributes described above as being obviated. The implants themselves can exhibit benign tissue healing and rapid endothelialization which inhibits migration, thromboembolism, infection, and/or erosion. In some cases, the coaptation assist body will exhibit no endothelialization but its surface will remain inert, which can also inhibit migration, thromboembolism, infection and/or erosion.

FIG. 8A-8B show two views of an embodiment of a coaptation enhancement element comprising a first surface 810 disposed toward a mal-coapting native leaflet, in the instance of a mitral valve, the posterior leaflet and a second surface 820 which may be disposed toward the anterior leaflet. The superior edge 840 of the implant may be curved to match the general shape of the annulus or adjoining atrial wall.

The coaptation assistance element has a geometry which permits it to traverse the valve between attachment sites in the atrium and ventricle, to provide a coaptation surface for the anterior leaflet to coapt against, and attach to the atrium or annulus such that it effectively seals off the posterior leaflet, or in the instance that the leaflet is or has been removed, that it replaces the posterior leaflet. FIGS. 13A-H, 14A-C, and 15A-B illustrate that geometry.

Figure 13A:
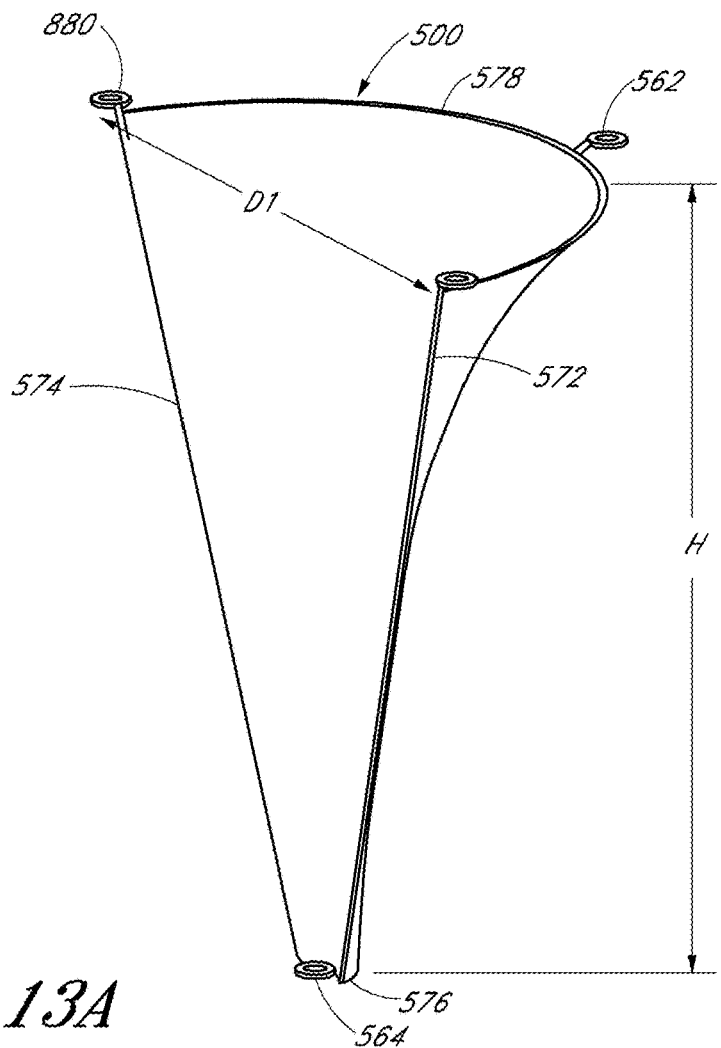
FIG. 13A schematically illustrates an axial view of an embodiment of the coaptation enhancement element.

FIG. 13A shows an oblique view of the coaptation assistance element 500, with annular anchor site 562 and ventricular anchor hub 564. While an annular anchor site is shown extending posteriorly from the body of coaptation assistance element, in an alternate embodiment the anchor site could be on the anterior surface. Passive or active commissural hubs 880 may define a diameter D1, which may in some embodiments correspond to the distance between the first and second lateral commissures of the native valve 110 or the intracommissural distance (ICD). D1 may range, in various sizes of implants, between 20-60 mm with, in some embodiments, a preferred length between 35-45 mm, as corresponding most closely to the widest range of human mitral ICD.

FIG. 13A further illustrates coaptation element height H, corresponding to the distance between the ventricular anchor site and the atrial anchor site as measured perpendicular to the plane defined by the annulus of the valve. Coaptation element height of some embodiments may be 30-80 mm, with some embodiments ranging between 40-55 mm.

Figure 13B:
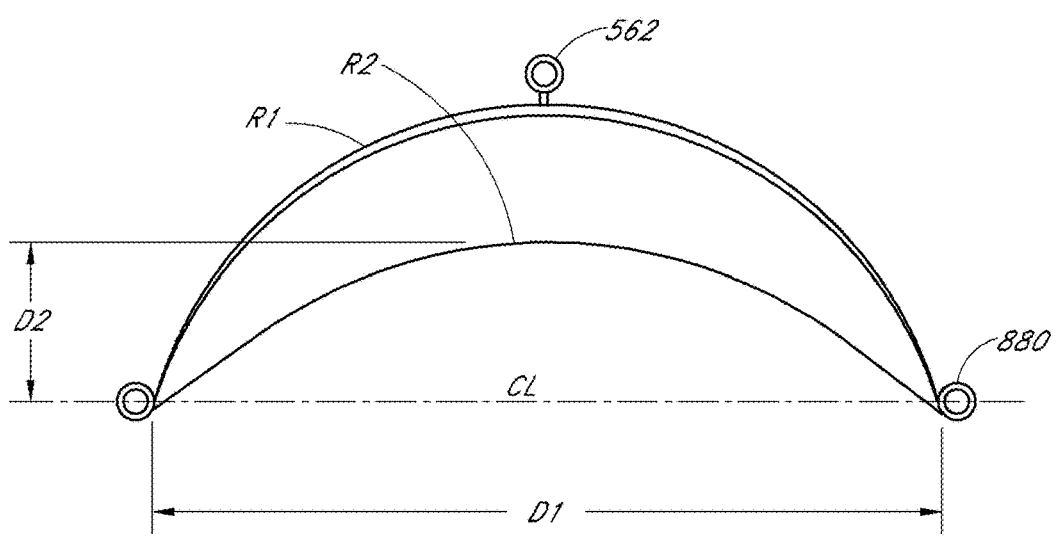
FIG. 13B schematically illustrates an end view of an embodiment of the coaptation enhancement element.

FIG. 13B illustrates the coaptation element in an end view, from proximal to the element. D1 is illustrated, and measures the distance between the medial edge and the lateral edge of the coaptation element at the level of the valve. In some embodiments, D1 may be the distance from the right to left fibrous trigones 124, 126 (FIG. 1F).

Further illustrated is measurement D2, which measures the distance from posterior to anterior between the most posterior point of R2 and center line CL connecting the medial and lateral edges of the coaptation element at the level of the valve. D2 may range between about 3 and about 10 mm. In one embodiment D2 may be about 6 mm. In another embodiment, D2 is about one-third of the distance between the midpoint of the posterior annulus and the midpoint of the anterior annulus. In some embodiments, D2 may be one-sixth to one half of the distance between the midpoint of the posterior annulus and the midpoint of the anterior annulus.

The coaptation zone curve radius (or short axis) R2 of the coaptation element is illustrated in FIG. 13B. The short axis is a transverse measurement of the coaptation element at the level of the heart valve. The anterior surface at the level of the coaptation zone is the portion of the implant which the anterior leaflet coapts against during systole. The coaptation zone radius in embodiments may be in the range of 20-60 mm, with preferred coaptation zone radius measurements in the 35-45 mm range, as corresponding favorably to a wide variety of patient measurements.

The annular curve radius R1 of the coaptation element is the measurement of the proximal or superior edge of the coaptation element. In some embodiments, the annular curve radius may be in the range of 15-50 mm. In other embodiments, R1 may be between 25-35 mm.

FIGS. 13A and 13C illustrate the generally triangular shape of embodiments of the implant, such that the coaptation implant has a superior edge 578, lateral edges 572 and 574, and inferior edge 576, wherein the superior edge 578 has a length greater than that of inferior edge 576, such that the transverse distance between lateral edges 572 and 574 generally decreases from superior to inferior on the implant. For example, the superior edge length may be in the range of 15-50 mm, or 25-35 mm, while the inferior edge length may be in the range of 1-15 mm, or 2-6 mm.

FIG. 13D illustrates a side view of one embodiment of the coaptation implant. Illustrated is a coaptation element length L1, corresponding to the distance between the most proximal measurement of the coaptation element and the ventricular anchor site as measured perpendicular to the plane defined by the annulus of the valve. The anticipated range in provided coaptation element lengths may be between 20-80 mm, with a preferred element length between about 35 and about 45 mm, as corresponding most closely to the majority of patients.

Also illustrated in FIG. 13D is a ventricular element length L2. This corresponds to the distance between the level of the valve and the ventricular anchor site as measured perpendicular to the plane defined by the annulus of the valve. The anticipated range in ventricular element length may be 10 to 70 mm, with a preferred ventricular element length range of 25-35 mm.

The coaptation element length L1 and the ventricular element length L2 can be further described by a element length ratio L2:L1. In embodiments, the element length ratio may be about, at least about, or no more than about 0.6, 0.65, 0.7, 0.75, 0.8, 0.85, or 0.9.

The overall element arc length L3 is the measurement from the superior edge to the inferior edge of the coaptation element measured along the implant. The overall element length may range between 25-100 mm. In some embodiments, L3 will range between about 50-60 mm.

Table 1, below, illustrates dimensional measurements for some embodiments in column 2, and specific dimensions for one contemplated embodiment in column 3.

TABLE 1

| Dimension | Column 2<br>Range of some embodiments | Column 3<br>One embodiment |
| --- | --- | --- |
| R1 | 25-35 mm | 28 mm |
| R2 | 35-45 mm | 39 mm |
| R3 | 5-12 mm | 8 mm |
| D1 | 20-60 mm | 40 mm |
| L1 | 20-80 mm | 40 mm |
| L2 | 10-70 mm | 30 mm |
| L2/L1 | 0.6-0.9 | 0.75 |
| L3 | 25-100 mm | 55 mm |
| D2 | 3-10 mm | 6 mm |

Figure 13F:
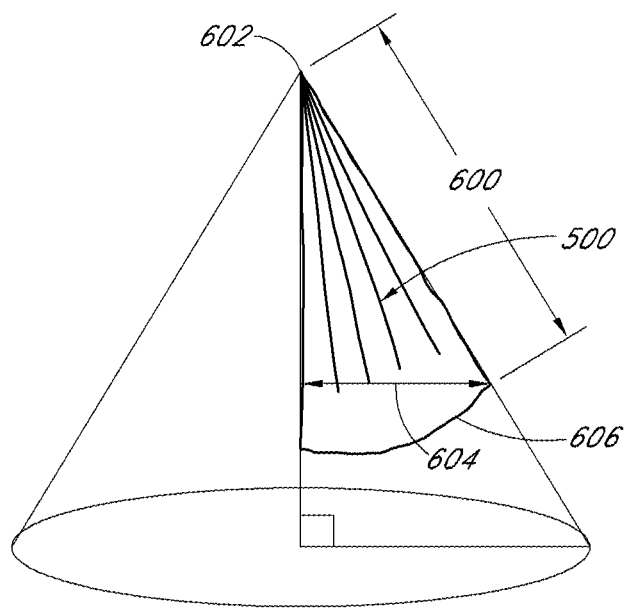
FIGS. 13F, 13G, and 13H illustrate the geometry of an embodiment of the coaptation element juxtaposed on a cone.

In some embodiments, as shown in FIG. 13F, the geometry of the coaptation element 500 conforms substantially to a portion of the surface of a cone. Embodiments describe a length 600 within a range of about 20 to about 80 mm along the primary axis of rotation between the apex 602 and the base arc 606, and a radius 604 of the base arc within the range of from about 25 to about 35 mm. Also, the linear distance between the two ends of the base arc has a length within the range of from about 20 to about 60 mm. The two endpoints of the base arc lie on the surface of the cone.

Figure 13H:
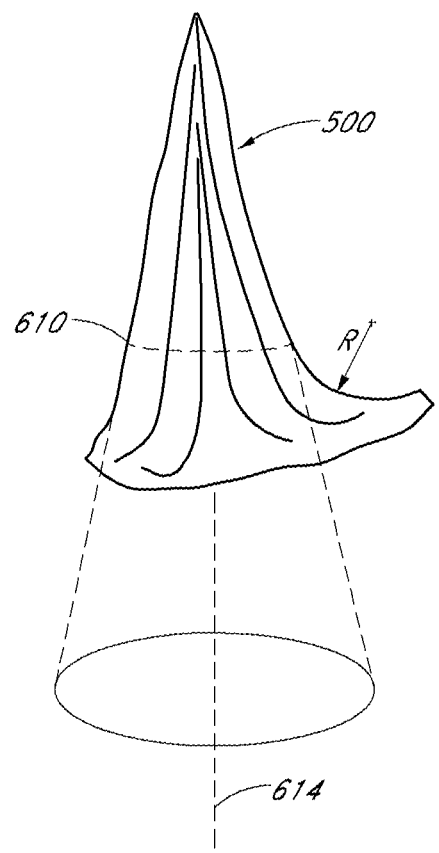
Figure 13G:
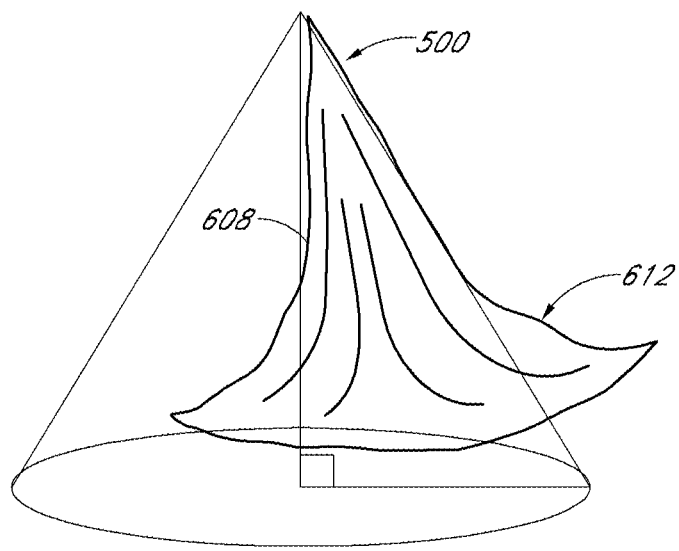

In other embodiments, as shown in FIGS. 13G and 13H, the implant conforms substantially to a portion of the surface of a cone for about 50 to about 70% of the total height 608 measured along the longitudinal axis 614 of the cone, then the implant flares radially outwardly from the cone. That radially outward flare 612 can be considered to have a radius within a range of from about 5 to about 12 mm. The inflection point 610 where the flare departs from the wall of the cylinder can be located within a range of distance from about 10 to about 70 mm along the longitudinal axis. The inflection point may be at about 45 to about 75% of the total length along the longitudinal axis. The implant can also have a total length along the axis within the range of from about 25 to about 100 mm, and the base arc can have a radius (measured perpendicular to the axis) within the range of from about 35 to about 45 mm.

Figure 13I:
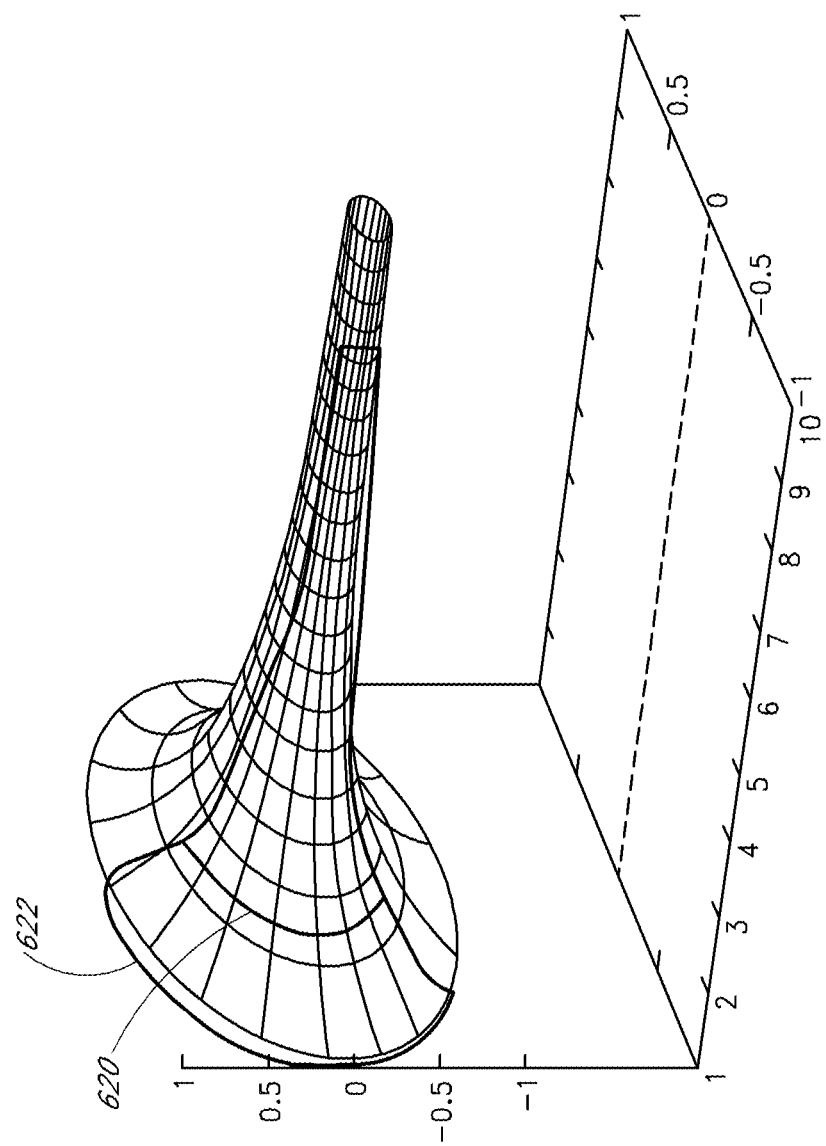
FIG. 13I illustrates the geometry of an embodiment of the coaptation element juxtaposed on a depiction of Gabriel's horn.

In a Gabriel's horn type embodiment, as shown in FIG. 13I, the line 622, 620 connecting the endpoints of the base arc can be described as perpendicular to the longitudinal axis of the Gabriel's horn, and laterally offset from the long axis by a distance of at least about 6 mm.

These embodiments, as illustrated by FIGS. 13F-M, are intended to generally describe the geometry of the implant. As would be appreciated by one of skill in the art, the coaptation element geometry may be roughly described with reference to this kind of system, yet vary somewhat from the precise geometry disclosed.

In another type of embodiment, the implant may have the configuration shown in FIGS. 13J-13M. In this configuration the implant has overall height H between the superior edge and the ventricular anchor measured in a plane perpendicular to the plane of the valve which measures between about 20 and 70 mm, in some embodiments in a range between about 25 and 35 mm. The overall element comprises a coaptation enhancement element which is coupled to a tethered ventricular anchor 866.

In this embodiment the coaptation element takes an approximately hexagonal shape with a tether connection 864 running from the inferior surface 764 of the coaptation element to the ventricular anchor 866 and ventricular anchor hub 864. The lateral edges 572, 574 travel from the superior edge 578 essentially perpendicular to superior edge 578 through the coaptation zone 920. This provides a broad surface for a native leaflet to coapt against. At around the level of or inferior to the level of the coaptation zone, lateral edges 572, 574 converge toward inferior edge 576 such that the distance between lateral edges 572, 574 diminishes from proximal to distal toward the inferior edge 576. Therefore, the implant presents a relatively small profile distal to the coaptation zone such that the element has a low profile in the ventricle. In this configuration, the coaptation element is configured to avoid interference with the ventricular papillary muscles which could cause the implant to be undesirably distorted in systole. Furthermore, the element is less likely to cause distortion of blood flow in the ventricle. The ventricular anchor 866 is designed to be placed on the posterior wall, between the papillary muscles.

In some embodiments, the tether 782 has length L5 between the inferior edge of the coaptation element 576 in the range of 2-30 mm, in some embodiments with a tether length L5 between about 10 and 20 mm. The proximal attachment at 764 may be to a hub, an eyelet, or any other tether site. In some embodiments, the tether 782 may comprise extensions of one or more of the longitudinal struts 830. Distal attachment of the tether 782 to the ventricular anchor hub 764 may be, as shown, through an aperture. The tether 782 may be attached to the ventricular anchor hub 864 or through any suitable means. The tether length L5 may be adjustable either before or after implantation, such that the tension across the element is customizable either based on patient anatomy, ventricular anchor placement, or both. Alternatively, the tether may be directly attached to a ventricular anchor or anchoring element. The tether may be comprised of any suitable material, such as suture, flexible material, Nitinol, metal, or plastic. The tether may be comprised of a material with sufficient elasticity to allow it to lengthen during ventricular systole, assisting the coaptation enhancement element in ballooning upward, which allows the coaptation zone 920 to more closely mimic a native leaflet and may enhance coaptation between the remaining native leaflet and the coaptation enhancement element.

The coaptation zone length L4, measured between the superior edge and the point where the lateral edges begin to converge, is configured to provide an adequate coaptation zone between the anterior leaflet and the leaflet facing surface of the implant, and has length L4 of between 5 and 30 mm, preferably about 15-25 mm. As discussed above, the lateral edges, 562, 564 may extend substantially perpendicularly with respect to the superior edge 568 for distance L4 to provide a broad surface for the native leaflet to coapt against. The proximal, coaptation portion of the coaptation enhancement element, as described by the superior edge, with a height corresponding to L4 and an inferior boundary basically parallel to the superior edge, may extend substantially downward in a direction basically perpendicular to the valve plane during at least its relaxed position in diastole or may describe a convex anterior (on the coaptation surface) curve. As described in relation to other embodiments, this proximal, coaptation portion of the element may also travel substantially parallel to the valve plane before curving distally or may actually curve superiorly and inward before curving distally.

The implant width D1 may in some embodiments correspond to the distance between the first and second lateral commissures of the native valve 110 or the intracommissural distance (ICD). D1 may range, in various sizes of implants, between 20-60 mm with a preferred length between 35-45 mm, as corresponding most closely to the widest range of human mitral ICD.

Figure 13J:
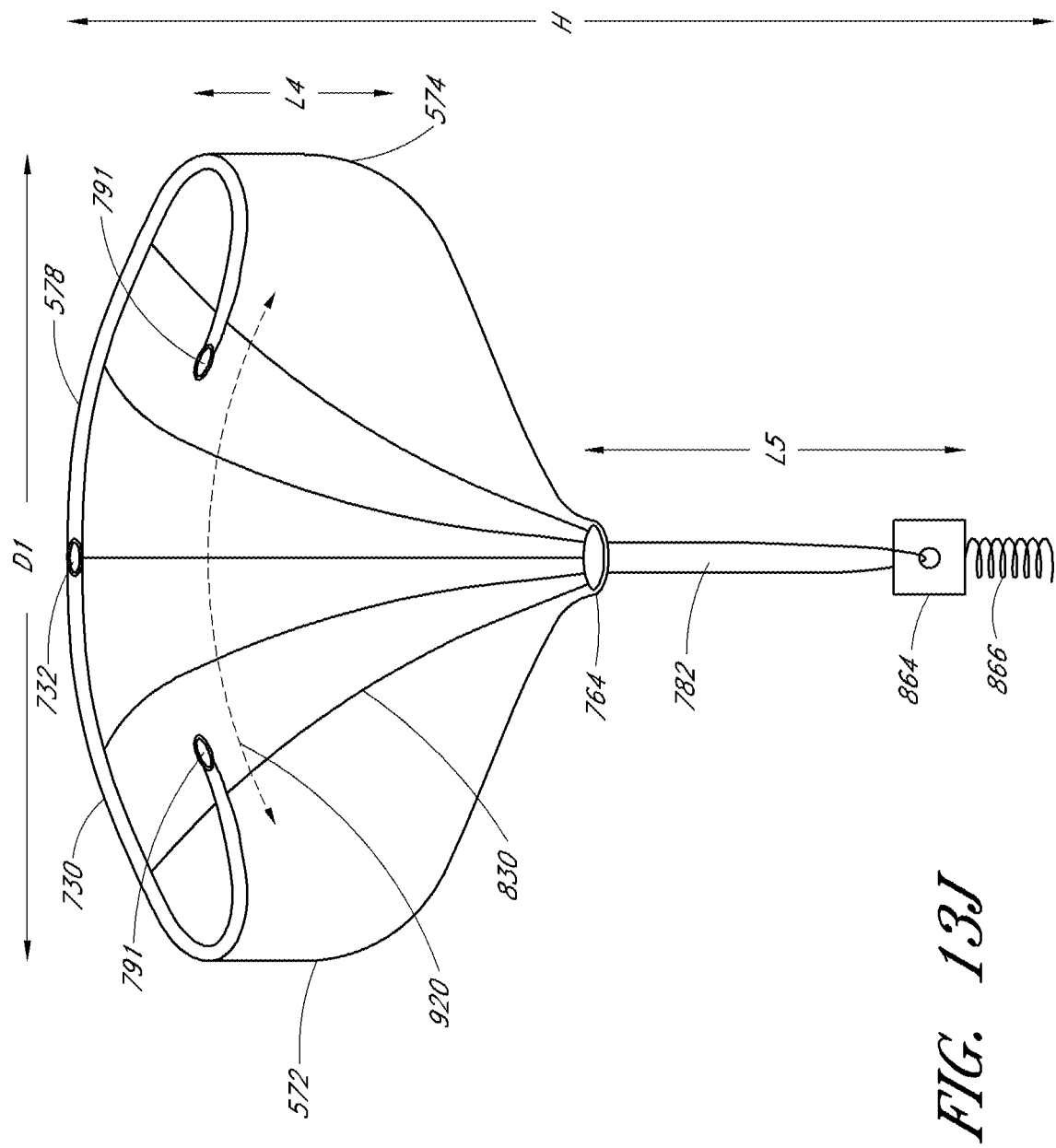
FIG. 13J illustrates the geometry of an embodiment of the coaptation element with a ventricular anchor extending from a tether and annular reinforcement ring.

In some embodiments, as shown in FIG. 13J, the annular reinforcement strut may extend beyond the lateral edges 562, 564. In these embodiments, trigonal anchor eyelets 791 correspond to the region of the implant that may be secured to the anterior and posterior fibrous trigones (See FIG. 1F). In general, the trigones are located approximately 1-10 mm lateral or medial to their respective commissures, and about 1-10 mm more anterior than the commissures. The embodiment in FIG. 14J illustrates an annular reinforcement strut 730 with integrated annular anchor eyelet 732 and trigonal anchor eyelets 791. In other embodiments, different trigonal anchor arrangements may connect the superior edge of the coaptation enhancement element to the anchor, including a hub or a tether connecting the anchor or an anchor hub to the element, with the medial end of the tether connected to an eyelet integrated into the surface of the element or any other suitable connection means.

Alternatively, as in FIG. 13K, commissural anchor eyelets 890 may be provided laterally at the lateral edges of the superior edge. As shown in FIG. 13L, the coaptation surface of the coaptation enhancement element may arise from the superior edge of the implant between points 793 and 795 laterally, and form a relatively flat crescent shape in the generally valvular plane with the crescent described between the superior edge and the coaptation zone 920, at which point it may proceed distally in a plane perpendicular to the valvular plane or even radially outward relative to a plane perpendicular to the valvular plane. In some embodiments, the coaptation surface of the coaptation enhancement element passes superiorly and radially inwardly from the superior edge, before passing distally, in a longitudinal direction perpendicular to the valve plane, or radially inwardly or outwardly with respect to the valve plane.

Figure 15B:
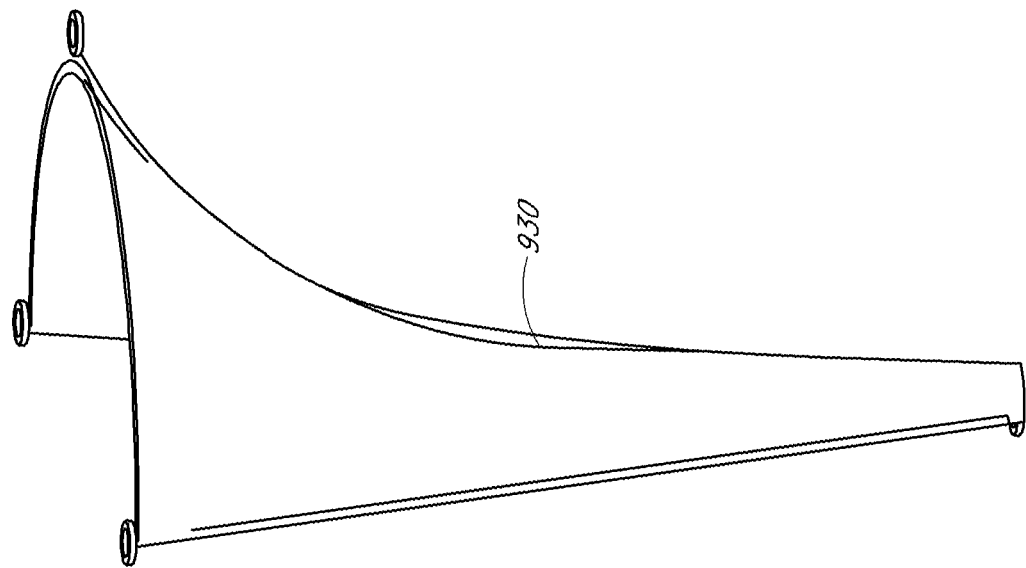
FIG. 15B schematically illustrates an oblique axial view of the coaptation enhancement element.
Figure 15A:
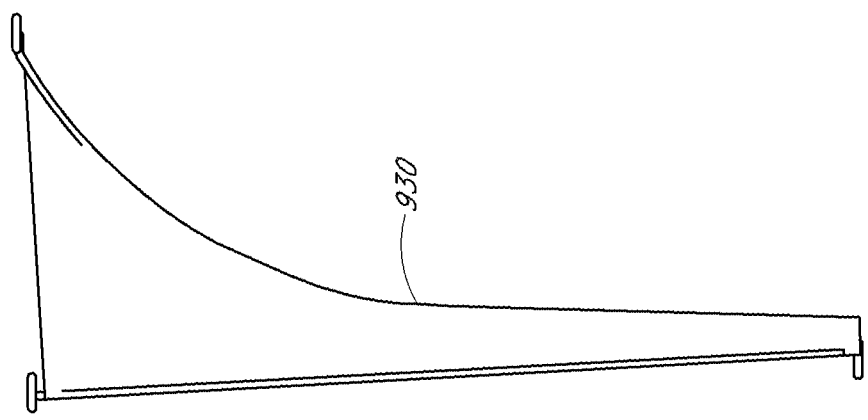
FIG. 15A schematically illustrates a lateral view of the coaptation enhancement element.

FIG. 14A-C show oblique views of the coaptation element with posterior surface 910, anterior surface 908, struts 830, and coaptation zone 920. Further illustrated in FIG. 14C and FIGS. 15A-15B is the long axis of the posterior leaflet curve L3, which corresponds to the measurement along the surface of the implant taken from the ventricular hub to the atrial/annular hub at the midpoint of the superior edge of the implant. The long axis of the posterior leaflet curve radius R3 range may be between 10-50 mm with a preferred radius between 20-30 mm as corresponding to most patients. The long axis of the posterior leaflet curve generally describes the path of the posterior leaflet complex from the ventricle through the papillary muscles, the chordae tendineae, the leaflet itself, and posteriorly toward the annulus/posterior wall of the atrium. It may be important that the curve of the implant generally correspond to the posterior leaflet curve at or near the end of ventricular systole, in order to correspond substantially to native anatomy when the coaptation element is placed over the posterior leaflet, and maintain relatively normal chamber size and geometry. In some embodiments, the curve of the implant changes over the course of the heart cycle, such that the coaptation zone of the implant behaves similarly to the lip of the posterior leaflet.

As may be seen in FIGS. 8A-B and 10A, struts 830 may be arranged generally parallel to the longitudinal axis of the implant to assist in maintaining the shape of the implant upon placement, while still allowing the implant to assume a reduced configuration for deployment through a catheter. The struts may be composed of a radio-opaque material. In some embodiments, the struts are composed of resiliently deformable materials such as a Nitinol alloy; in other embodiments, they may be composed of other materials to include stainless steel, polypropylene, high density polyethylene (PE), Dacron, acellular collagen matrix such as SIS, or other plastics, etc. In other embodiments the struts may be a combination such as a high density PE sheath around a core of ePTFE, Dacron, and/or polypropylene. The struts may have a circular cross section, an oval cross section, or be ribbon-like. In some embodiments, they are coiled springs or zig-zag shaped. They may have a constant stiffness, or they may be stiffer at the annular end than at the ventricular end of the valve body. The valve body covering 850 may be comprised of a material such as ePTFE. Other materials for the covering include polyurethane foam, polycarbonate foam, biologic tissue such as porcine pericardium, pleura, peritoneum, silicone, Dacron, acellular collagen matrix, etc. In some embodiments, the valve body covering can include a foam material surrounded by ePTFE. Use of sponge or foam material enhances the capability of having the implant fold to a small enough diameter to pass through a catheter. In some embodiments the valve body covering has no pores, or may have micropores to enhance endothelialization and cellular attachment. The valve body may also incorporate a radiopaque material or an echo-enhancement material for better visualization. Any support structures of the valve body or support interface having a frame may be coated with radio-opaque materials such as gold or platinum or impregnated with barium. The leaflet apposing valve body element 860 may be coated with an echo enhancement material. The valve body element 860 may be coated with a material to inhibit thrombosis, such as heparin bonding or quinoline and quinoxaline compounds, or with a material to accelerate endothelialization, or with antibiotic to inhibit infection. The coaptation assistance device may be composed of struts sandwiched between layers of covering material, which may or may not be composed of the same material on both surfaces. Alternatively, the struts may be attached to or embedded in the first or second surface of a single layer of covering material, or may be "stitched"

through the covering material 890 as in FIG. 10E. Additionally or alternatively, one or more support struts may be provided which run parallel to the superior edge of the coaptation element 890 and assist in maintaining the shape of the superior edge.

In some embodiments, the coaptation element support structure includes a flattened metal mesh such as found in stents, covered by a valve body covering such as ePTFE, Dacron, porcine pericardium, etc. The mesh collapses for introduction through a catheter.

Figure 9:
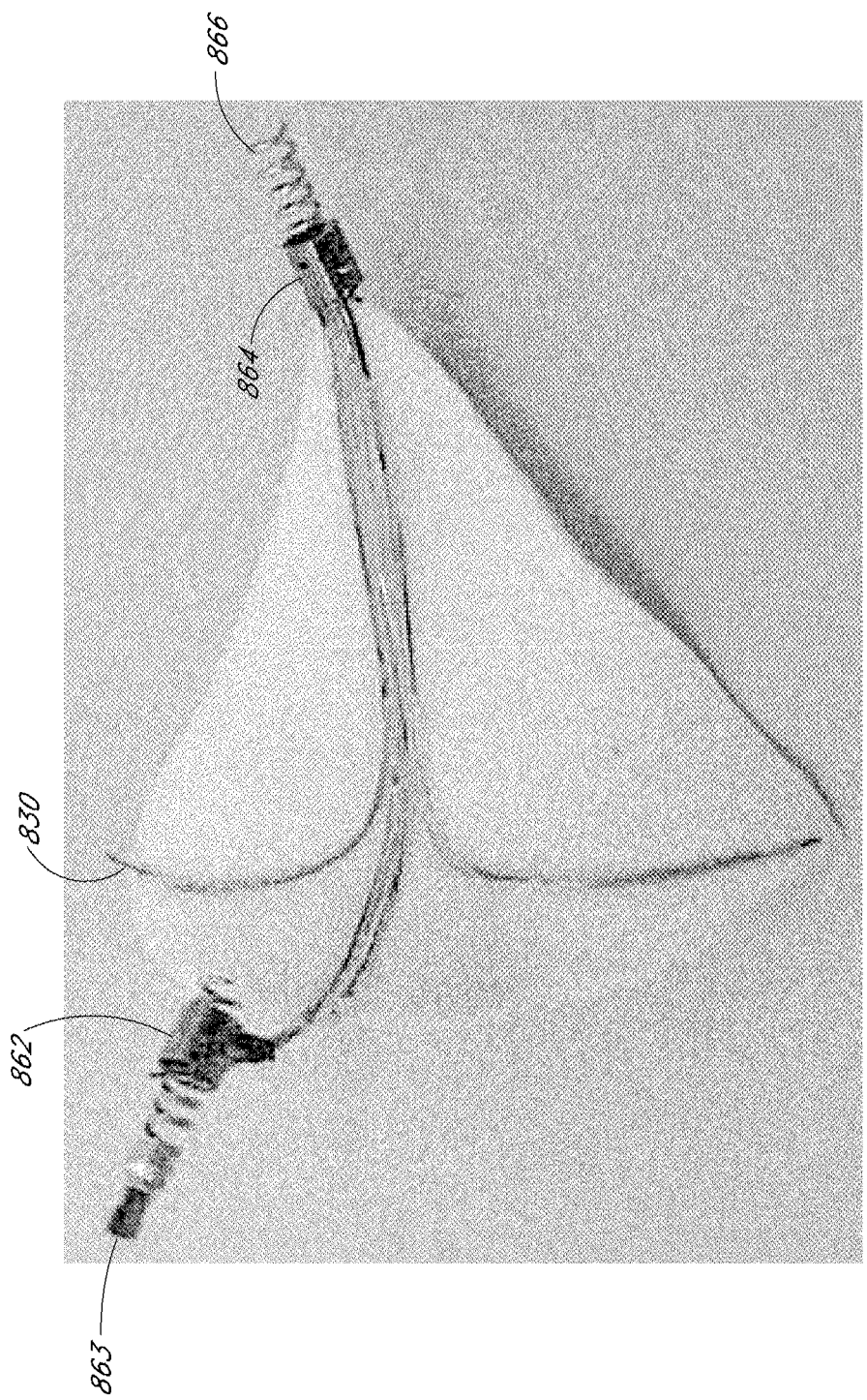
FIG. 9 shows another embodiment of a coaptation enhancement element with atrial and ventricular anchors.

An alternative embodiment of the coaptation assistance device is shown in FIG. 9. Struts 830 are shown in a different configuration, in which one or more curve laterally toward the superior edge to assist in maintaining the shape of the proximal portion upon deployment. Also shown on this configuration are an atrial hub 862 for connection to annular or atrial anchor 863 and a ventricular hub 864 for connection to ventricular anchor 866. Alternate engagement means are contemplated for connecting the device to each anchor, including the portrayed eyelets and hubs, but also including other connection means known to one skilled in the art, such as, for example, sutures, staples, adhesive or clips. In alternative embodiments, the anchors may form an integrated part of the device. In the embodiment of FIG. 9, both anchors shown are helical anchors. There are many possible configurations for anchoring means, compositions of anchors, and designs for anchoring means.

The coaptation assistance device or implant may include one or a plurality of atrial anchors to stabilize the device and/or a ventricular anchor, with the anchors optionally providing redundant fixation. The atrial anchor or anchors may attach to or adjacent the annulus. The annular anchor, if it is included, may be covered with biocompatible materials such as ePTFE or Dacron to promote endothelialization and, optionally, chronic tissue in-growth or encapsulation of the annular anchor for additional stability.

The annular anchor may include a plurality of barbs for acute fixation to the surrounding tissue. In other embodiments, the atrial anchors may comprise a plurality of helixes, clips, harpoon or barb-shaped anchors, or the like, appropriate for screwing or engaging into the annulus of the mitral valve, tissues of the ventricle, and/or other tissues of the atrium, or the atrial or ventricular anchors may attach to the tissue by welding using RF or other energy delivered via the elongate anchor coupling body.

The ventricular anchor may comprise a helix rotatable with respect to the leaflet apposing element and connected to the hub of the leaflet apposing element by a suture or ePTFE tube. In some embodiments, a ventricular anchor may be included in the form of a tether or other attachment means extending from the valve body thru the ventricle septum to the right ventricle, or thru the apex into the epicardium or pericardium, which may be secured from outside the heart in and combined endo/epi procedure. When helical anchors are used, they may comprise bio-inert materials such as Platinum/Ir, a Nitinol alloy, and/or stainless steel.

As noted above, in some embodiments, an atrial anchor in the form of an expandable structure for placement in the left atrial appendage may be included. In still further embodiments, an atrial anchor and support interface may be included in the form of a flexible line or tether attached to an atrial septal anchor. The atrial septal anchor may be configured like a transseptal closure device, optionally using structures that are well known. Any left atrial appendage anchor or atrial septal anchor may be covered with a biocompatible material such as ePTFE, silicone, Dacron, or biologic tissue, or fixed in place using RF welding. A left atrial appendage anchor or atrial septal anchor may be connected to the leaflet apposing valve body element with suture, or ePTFE tube, or may comprise a pre-shaped and rigid or resilient material such as a Nitinol alloy.

Referring now to FIGS. 10A-10E, further schematic drawings of the coaptation element are shown. In FIG. 10A, the device 100 is shown with alternate anchor embodiments, in which an active, helical atrial anchor 863 and active, helical ventricular anchor 866 are coupled to the device. However, passive, lateral commissural anchors 880 are also illustrated, and may help maintain the shape and position of the implant once deployed in the heart.

Alternatively, there may be a coupling mechanism on one or both commissural aspects of the atrial portion of the device which may be configured to engage active anchors 886 via eyelet 884 or hub, as shown in FIGS. 10D and 10E. Similarly, in some embodiments, a support may be placed along the annular margin of the element to assist in maintaining the curvature of the element.

In FIG. 10B, one possible framework structure is shown, with Nitinol strut 830 connecting the atrial eyelet 862 and ventricular hub 864. Other struts may be incorporated into the covering, as seen, for example, in FIGS. 8 and 9. These struts may be separate, be integrated to the ventricular hub, or form a framework incorporating each other. The struts may be shaped in any number of ways to assist in maintaining the desired shape and curvature of the implant. FIGS. 8 and 9 show two variations, though many others could be contemplated and should be obvious to one skilled in the art.

FIGS. 10D and 10E show another embodiment in which an annular ring 890, comprising of a material such as Nitinol cable or a deformable plastic, is placed at or near the superior edge of the coaptation element and in the same plane. In some embodiments, this annular ring may terminate laterally in a hub or eyelet for active commissural anchors 884, while in other embodiments it may terminate laterally in a passive anchor. The annular ring as thus contemplated provides assistance in maintaining the desired proximal geometry of the coaptation assist element. The annular ring may, for example, be planar, or it may be saddle shaped to correspond with the three dimensional shape of the native valvular annulus.

Figure 10F:
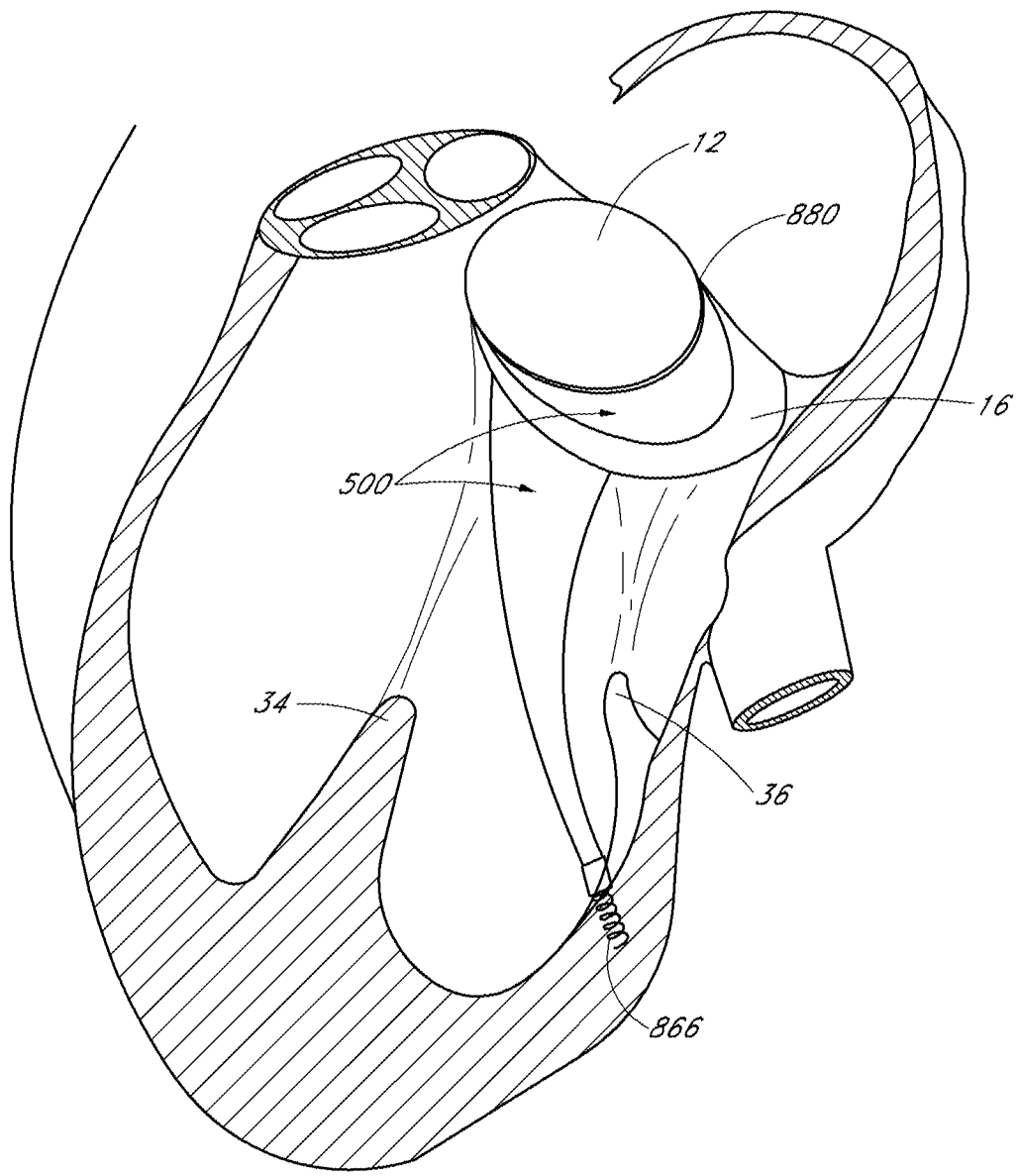
FIG. 10F schematically illustrates a heart with an embodiment of the coaptation element implanted across the mitral valve.

Turning now to FIG. 10F, the coaptation element 500 when deployed in the heart attaches via ventricular anchor 866 distal to the mitral valve along the path of blood flow, traverses the valve, and attaches proximally in the atrium such that it functionally replaces the posterior leaflet 16, which may be covered by the element or removed in part or totally, the element coapting to the anterior leaflet and providing coverage posteriorly from the coaptation zone to the periphery of the annular ring. It is contemplated that the coaptation element will experience some motion and deformation as the surrounding cardiac structures move in relation to one another during the cardiac cycle; however, repetitive stresses on the device are minimized by its relatively stationary position, lessening the possibility of fatigue over time and maximizing the life of the implant. Materials used in the covering and frame of the element may be chosen with this in mind.

It may be desirable to cover the posterior leaflet from the level of the valve and proximally so coaptation of the anterior leaflet against the element seals off communication between the atrium and ventricle and thus mitigates the mal-coaptation, reducing to a minimum or entirely eliminating mitral regurgitation, without involving the posterior leaflet in the seal. The coaptation element may be designed to permit relatively normal circulation of blood in the ventricular chamber, as it may be elongate and narrow between the anterior and posterior surfaces, taking up minimal space and allowing movement of blood from one side to another and past both lateral aspects of the element. As can be seen in FIG. 13A-13C, struts made of Nitinol, stainless steel, or other appropriate materials, can substantially assist in maintain the geometry of the implant, permitting choice of any of a wide variety of covering materials best suited for long term implantation in the heart and for coaptation against the anterior leaflet.

Figure 11B:
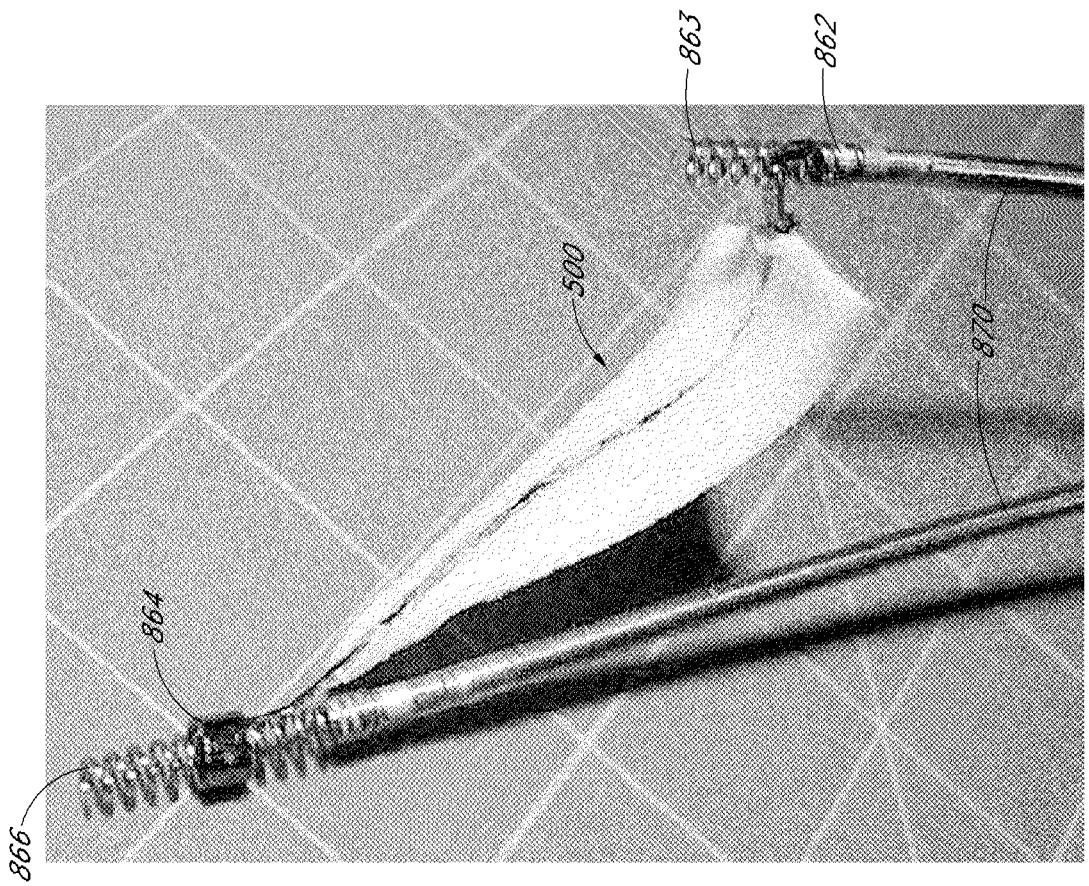
FIGS. 11A-B show a coaptation enhancement element with atrial and ventricular anchors attached and mounted to anchor drivers.
Figure 11A:
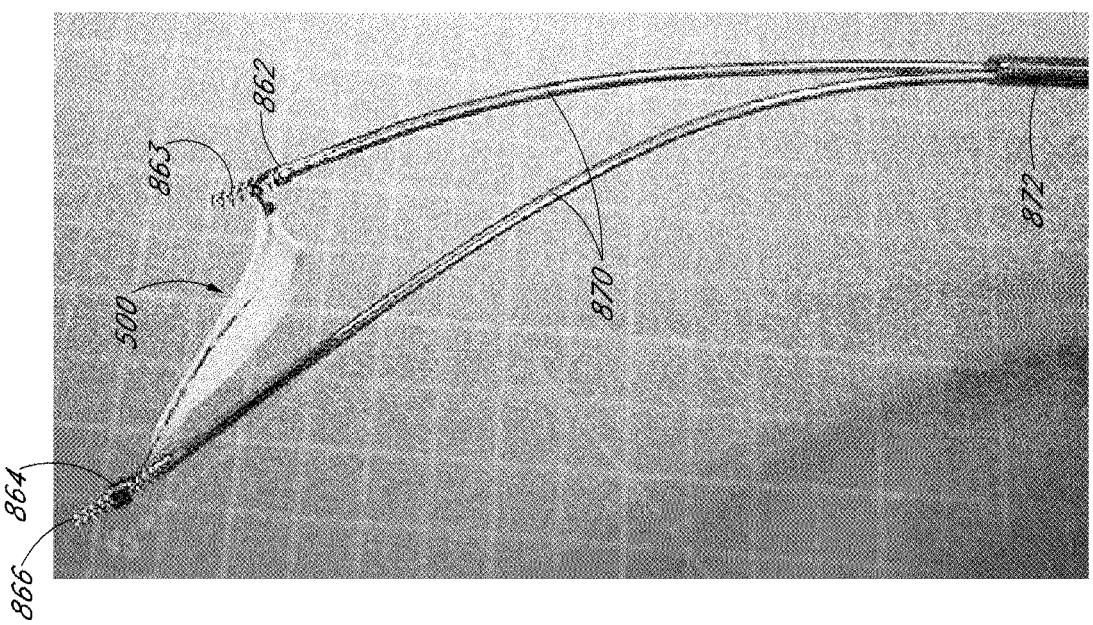
Figure 11C:
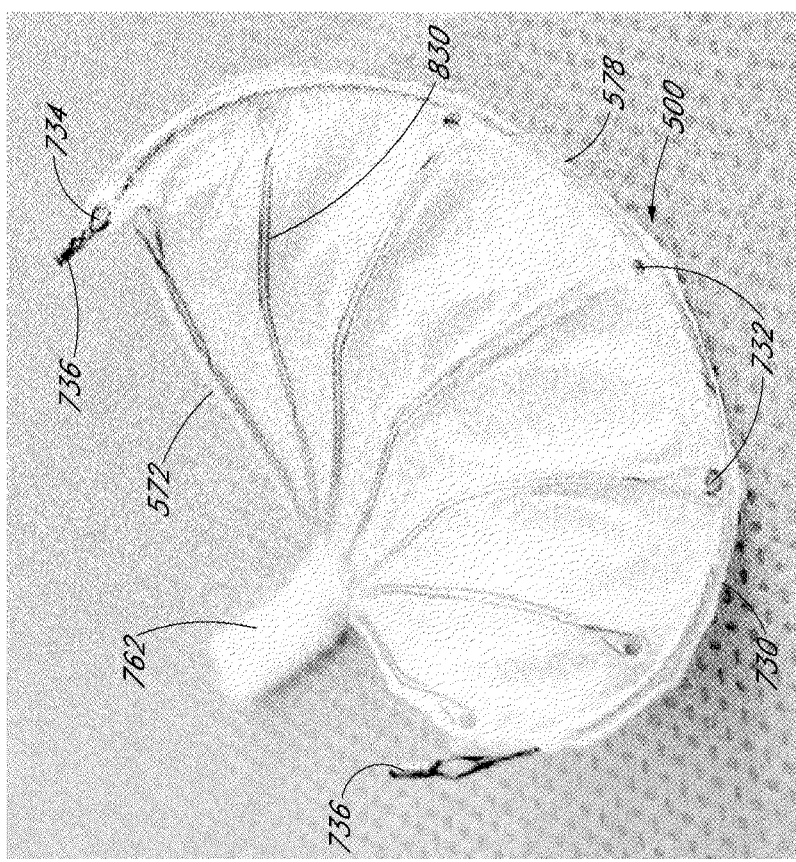
Figure 12A:
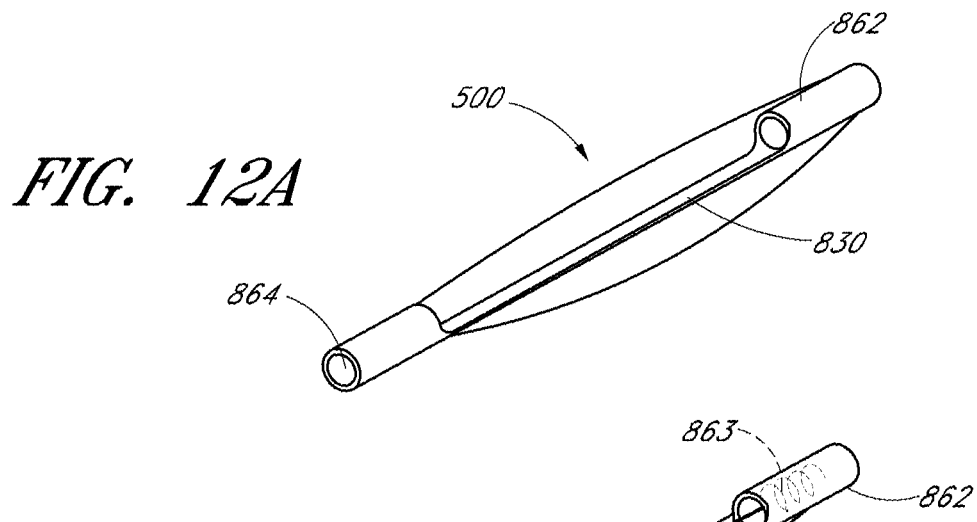
FIG. 12A schematically illustrates an embodiment of the coaptation element in its collapsed state, FIG. 12B schematically illustrates the coaptation element of 12A with anchors attached and mounted to anchor drivers.
Figure 12B:
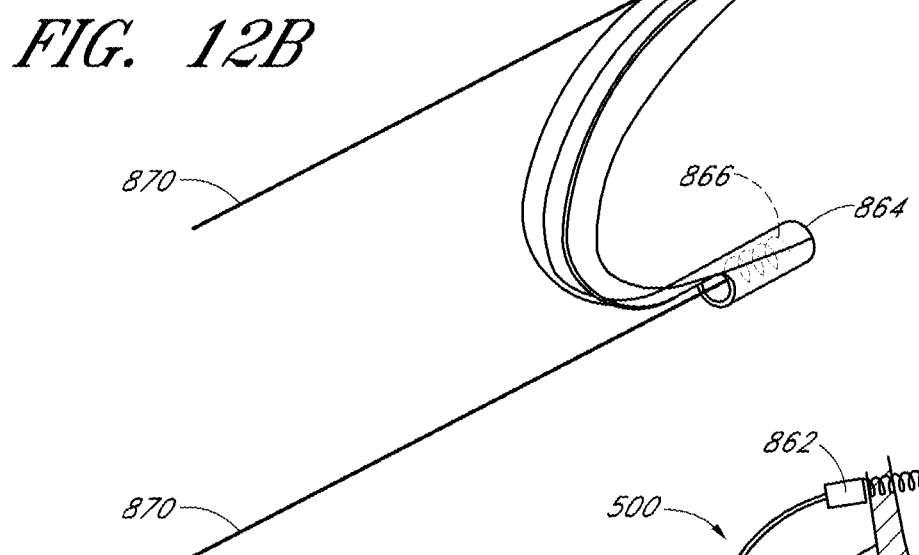
FIG. 12C schematically illustrates the coaptation element deployed across the mitral valve.
Figure 12C:
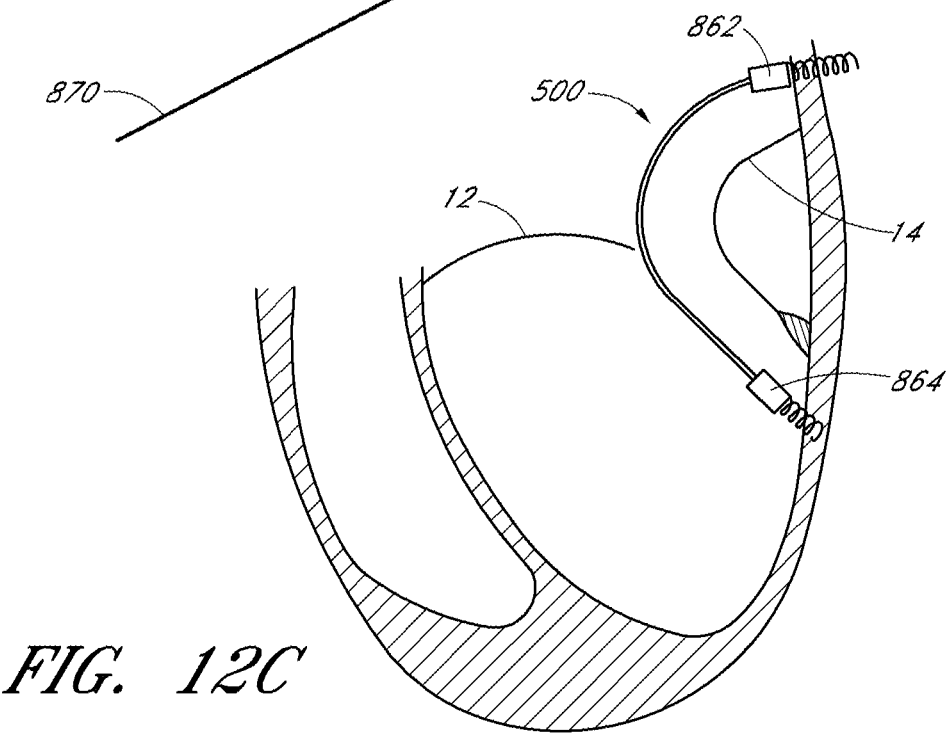

Turning now to FIGS. 11A-11B and 12A-12C, an embodiment of the coaptation assistance device 500 is shown with ventricular hub 864 engaging ventricular anchor 866 and annular eyelet 862 engaging annular anchor 863. Each anchor may be engaged at its proximal end by a driver 870. In FIGS. 11A, 11B, and 12B, the drivers are seen emerging from placement catheter 872. It can be seen that in some embodiments, the device can be assembled extracorporeally, engaging the anchors to the device and the drivers to the anchors. The drivers can then be withdrawn into the catheter, with the device in its collapsed position as shown in FIG. 12A 500. The drivers may be separately manipulated by the surgeon to place the anchors in the appropriate positions. Alternatively, the anchors may be engaged to the device and/or the driver sequentially, either before or after deployment through the catheter. FIG. 11C illustrates the coaptation element after placement, entirely covering the posterior leaflet 14 so that it coapts with the anterior leaflet 12 during systole and, with the native anterior leaflet, maintains the valve seal at the annular ring.

Figure 11D:
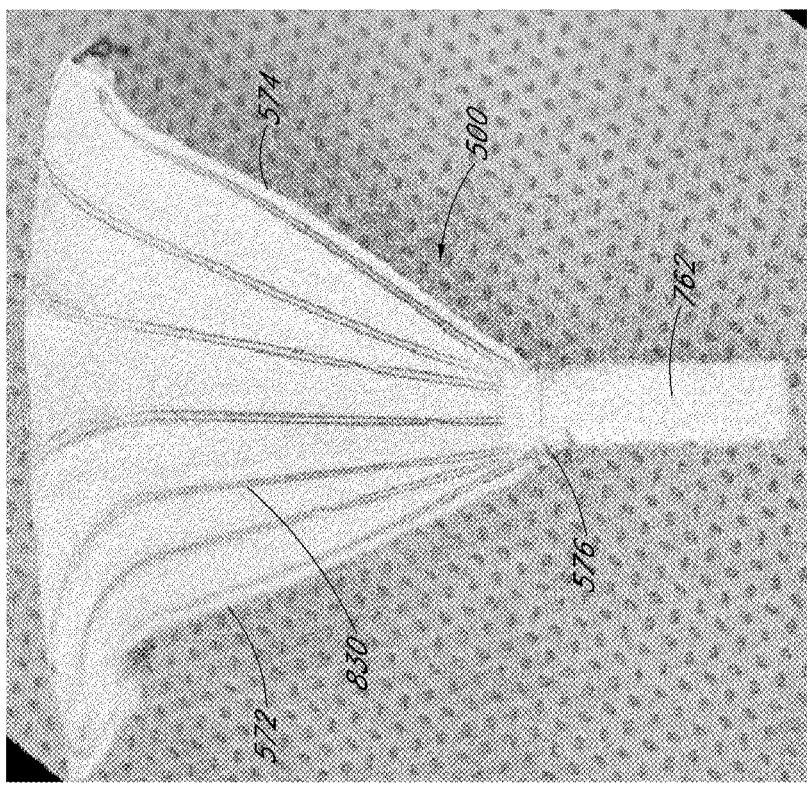
FIGS. 11C-D show two views of a coaptation enhancement element with multiple annular or atrial anchor eyelets and ventricular pledget.
Figure 11E:
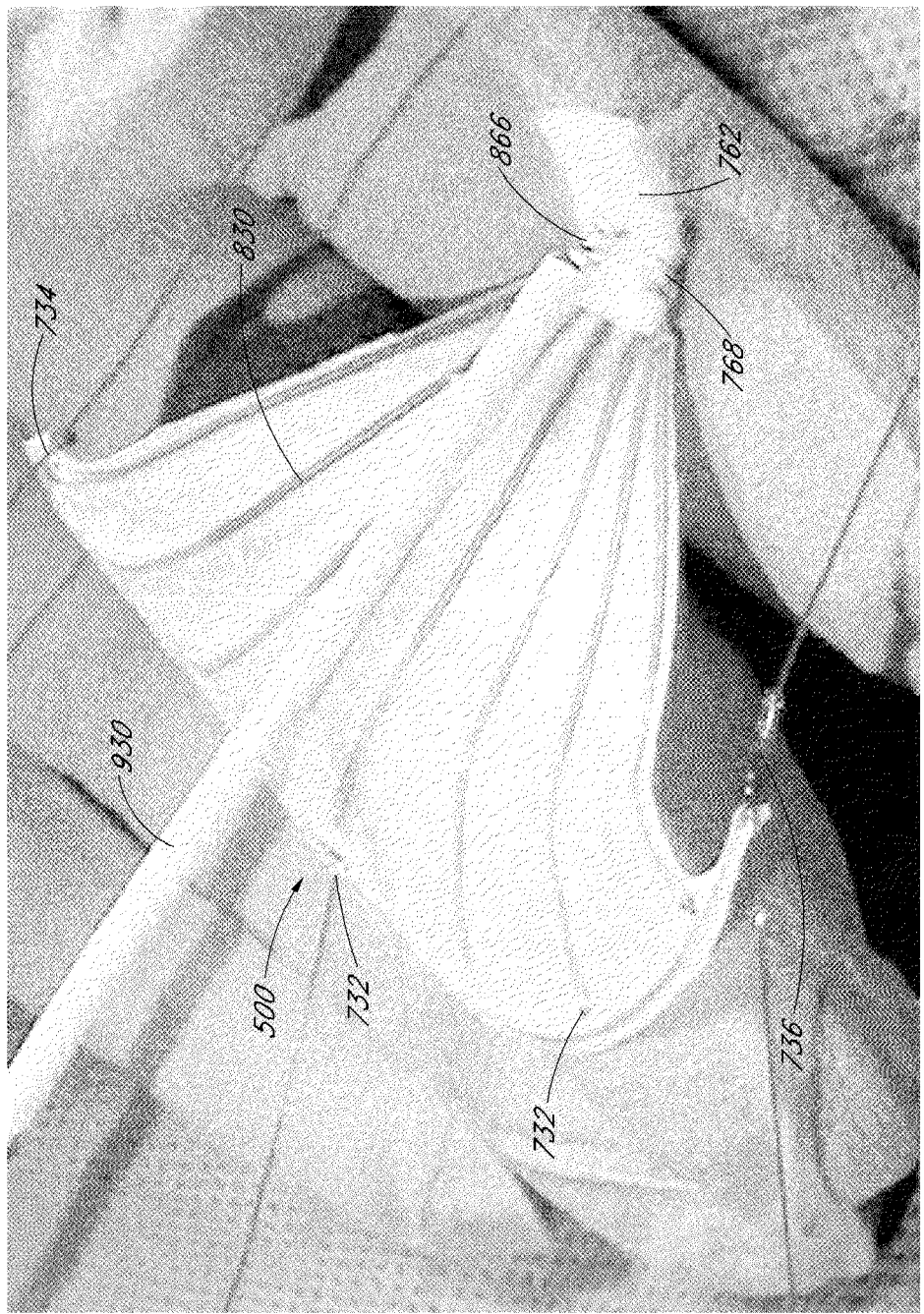
FIG. 11E shows the coaptation enhancement element of FIGS. 11C-D with delivery catheter and ventricular anchor.

Another embodiment of the coaptation assist element may be seen in FIGS. 11C-E. In this embodiment, a number of coaptation element struts 830 run from the inferior edge 576 of the implant along the longitudinal axis. The struts may connect inferiorly to each other or to a ventricular hub. Alternatively, they may connect to a ventricular anchor pledget 762, as seen in FIGS. 11C-E. Each strut may terminate inferiorly within the covering of the element. Each strut may comprise a single longitudinal element or be doubled over to comprise two or more strands. As shown in FIGS. 11C-E, a single strut may be comprised of a strand of Nitinol wire or other material which loops toward the superior aspect of the implant. This loop area may, as shown in the Figures, provide reinforcement around an interruption in the covering material, such as for an annular anchor eyelet 732, from which an anchor may be deployed, either directly or with one or more intervening connecting structures, such as a tether and attached hub. The struts 830 may be, as shown, placed such that they are relatively evenly spaced, or may be concentrated toward the center or lateral edges 572, 574. The annular anchor eyelet may be coupleable with an anchor or anchoring element which may be deployed into the mitral annulus, left atrium, left auricle, or one of the fibrous trigones.

In some embodiments, there may be transverse struts connecting two or more of the longitudinally oriented struts to provide additional reinforcement, for example, near the coaptation zone. An additional annular reinforcement strut 730 may be provided at or near the superior edge of the element 578. This may terminate at or near the lateral edges 572, 574, or may continue past as part of one or more commissural anchors.

The annular reinforcement strut 730 may connect with one or more longitudinal struts 830, or as shown, may be placed superiorly within the covering material, such that it is more easily compacted for delivery via catheter. This may also provide increased durability for the implant if the annular reinforcement strut 730 reinforces the tethering to the annulus or atrium, while the longitudinal struts, which provide support during upward ballooning or stretching of the body of the coaptation element during ventricular systole, may have increased ability to move slightly away from each other laterally during systole and towards each other during diastole. Maintaining a separation between the transverse annular reinforcement strut 730 and the longitudinal struts 830 may also improve function of the coaptation enhancement implant by allowing the upward rotation between the superior edge of the longitudinal struts and the annular reinforcement strut, such that the superior portion of the implant through the coaptation zone may more closely replicate the motion of a native leaflet during systole. With a relatively rigid construct wherein the superior rim connects directly to the longitudinal struts to form a frame, the implant longevity may be lessened as the supporting annular reinforcement strut must move each time the surface of the implant moves, and the coaptation between native leaflet and coaptation element may not be optimized by the element having some movement during the cardiac cycle. Furthermore, use of the annular anchor eyelet or eyelets 732 which originate near the superior edge of the longitudinal struts 830 may be accomplished in addition to or in lieu of one or more commissural anchors which may or may not be connected to the annular reinforcement strut.

The annular reinforcement strut is shown in FIGS. 11C-E as terminating near commissural eyelets 734. Each of the one or more eyelet openings 734 may be formed by a loop of the annular reinforcement strut, or may be separate from the annular reinforcement strut 730. The eyelet may be directly connected to an anchor, or an annular anchor hub 736 either directly, via a tether structure, or through other means. In some embodiments, localized loops in the annular reinforcement strut 730 may surround and define annular anchor eyelets 732.

The implant of FIGS. 11C-E may comprise a ventricular anchor pledget 762 as a means of connection between the ventricular anchor and the coaptation enhancement element. The ventricular anchor pledget may be of generally rectangular shape as shown, or may be square or rounded, elliptical, or any other convenient form. The pledget may be comprised of any one of a number of suitable materials known to those of skill in the art. In some instances it may be advantageous to use a material which promotes tissue ingrowth, enhancing the connection of the coaptation implant to the patient's tissue. In other embodiments, a material which inhibits or is inert with respect to tissue ingrowth may be preferred, such as ePTFE, VTFE, PTFE (poly tetrafluoroethylene), Teflon, polypropylene, polyester, polyethylene terephthalate, or any suitable material. In some embodiments, a coating may be placed on the pledget to inhibit or encourage tissue ingrowth. One or more anchors may penetrate the material of the pledget at a suitable position, securing the pledget to underlying cardiac tissue. Thus, in some embodiments, the pledget may comprise an easily punctured material, such as structural mesh, felt, or webbing.

FIG. 11E shows a coaptation element 500 with longitudinal struts 830 ending superiorly in loops with annular anchor eyelets 732, an annular reinforcement strut 732, commissural anchor eyelet 734 and commissural anchor hub 736. Inferiorly, ventricular pledget 762 is shown coupled to the implant distally 768. Any means of coupling may be used, including suture, wire, incorporation into the layers of covering, placement of a rivet, or other means. Ventricular anchor 866 is seen emerging from delivery catheter 930 and penetrating the pledget 768.

Figure 16A:
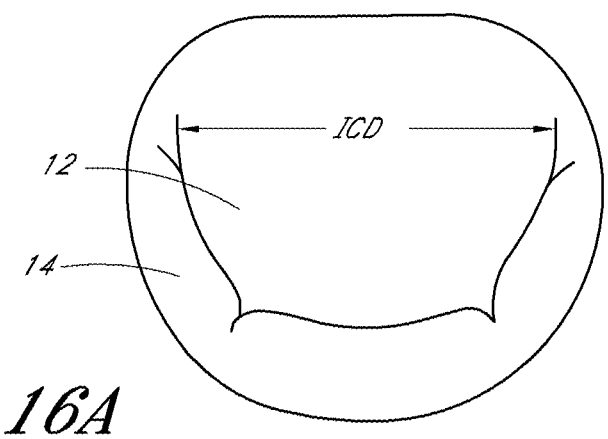
FIG. 16A schematically illustrates a superior view of the mitral valve for taking preoperative echocardiogram assisted measurements in order to select an appropriately sized implant.
Figure 16B:
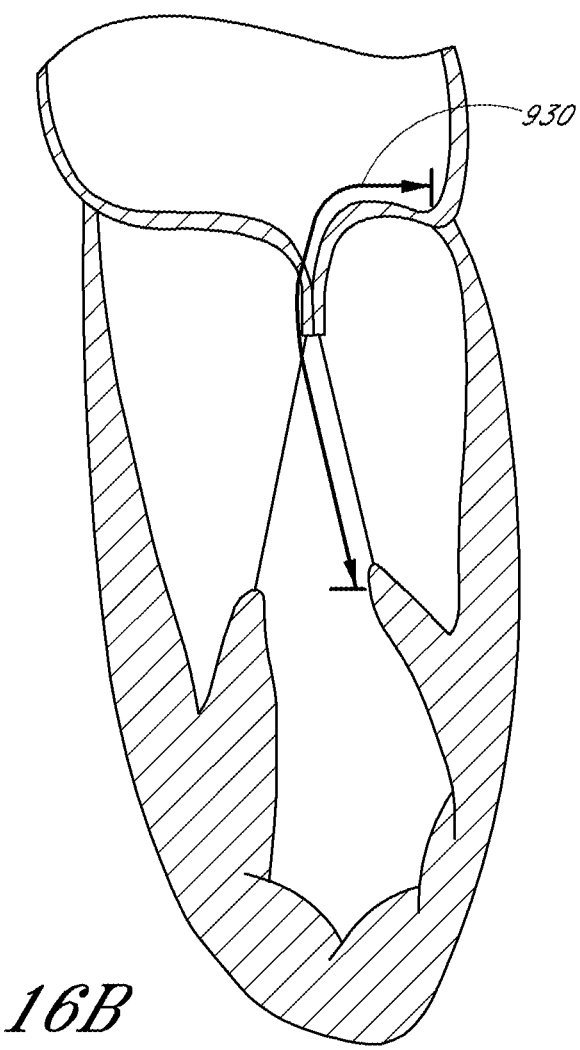
FIG. 16B schematically illustrates an axial view of the left side of the heart for taking preoperative echocardiogram assisted measurements in order to select an appropriately sized implant.

Geometry of the implant allows a limited number of implant sizes to cover a wide range of patient measurements. Furthermore, surgeon measurement can be done preoperatively or even intraoperatively with relative ease. Two measurements taken via echocardiogram can be used to determine the appropriate implant size. As shown in FIGS. 16A-B, end view of the valve permits measurement of the intracommissural distance ICD, and measurement of the long axis of the posterior leaflet 930 can be performed while obtaining an axial view on echocardiogram. Using these two measurements as a guide, appropriate selection from among the coaptation assist elements can be performed. Alternatively, other measurements can be used in combination to guide selection of the appropriately sized implant. In addition to echocardiogram, it may be possible to use x-ray, CT, cardioscopy, or MM to obtain measurements. Echocardiograms can be recorded via transthoracic route, trans-esophageal or intracardiac. It will be understood that to those skills in the art that the appropriate imaging modality and angle(s) of view will be used depending on the configuration of the implant and the method of its anchoring.

The coaptation assistance devices described herein are often configured for transvascular delivery and/or deployment via minimally invasive surgery (e.g. thoracotomy, transapically, via the left atrial appendage (LAA), via the right pulmonary vein, other left atriotomy or the like), with delivery and placement preferably being in between or adjacent to the cardiac valve's native leaflets. In particular, the valve can be one of the AV valves such as the tricuspid valve and/or the mitral valve. The drawings and some embodiments largely relate to the mitral valve, but analogous methods and devices can be applied to the tricuspid valve. The coaptation assistance body of the implant can often be delivered by a delivery catheter and may be capable of expanding from a smaller profile to a larger profile to dimensions appropriate for placement in between the valve's native leaflets. In some embodiments, the implants may also find applications for treatment of nonnative valve leaflets (for example, after valve replacement) or for treatment after the native leaflets have previously been surgically modified.

Turning now toward implantation, the coaptation assist element may be implanted through a minimally invasive or transcatheter technique utilizing a delivery system. As illustrated in FIG. 16C, the delivery system may include a delivery catheter 930, with delivery catheters comprising a variable stiffness shaft with at least one through lumen, the shaft configured for deflecting along at least a distal section 932. The delivery catheter deflection may be controlled by a catheter deflection or sleeve control knob 938, via an elongate pull wire extending through the catheter shaft to the deflection zone. The delivery catheter may further include a control handle 934 to manipulate the device anchors 866, 886 and to manipulate the docking and undocking of the device with the delivery catheter. The control handle may further include flush, irrigation and/or aspiration ports to remove the air from the system and allow injection of fluids such as saline or contrast media to the site of implantation, and electrical signal connections for monitoring and recording intracardiac electrograms from the distal aspect of the delivery catheter 930.

The delivery system may also include at least one torque shaft or other elongate anchor coupling body for manipulating the device anchors, initially deploying and recapturing of the anchors to and from the delivery catheter, and guiding the valve body distally to one or more of the initially deployed anchors. The coupling body may be a driver shaft 870, controlled by the active anchor control knob 940. Further, the anchor(s) and/or coaptation body may be connected to the delivery system via tethers 950, which allow the connection to be maintained after deployment of the anchor or device while testing the position and function of the implant. The tethers allow the implant to be re-secured to the delivery system in the event that placement may be initially sub-optimal, permitting readjustment. Tether control knob 942 may be provided on the control handle in order to maintain and manipulate a tether.

The delivery system may also include an outer sheath or introducer, typically to allow the introduction of the delivery catheter through a lumen of the outer sheath and into the left atrium, so that the outer sheath functions as a transseptal sheath 944. The transseptal sheath may include a variable stiffness outer shaft with at least one lumen, the lumen sized to allow insertion of the delivery catheter 930 and/or coaptation assistance body 500 through the sheath lumen. A deflectable distal section of the transseptal sheath 946 may facilitate alignment of the coaptation assistance device with the valve leaflets.

A transseptal method for treatment of MR will often include gaining access to the left atrium LA via a transseptal sheath. Access to the femoral vein may be obtained using the Seldinger technique. From the femoral vein, access can then be obtained via the right atrium 20 to the left atrium 10 by a transseptal procedure. A variety of conventional transseptal access techniques and structures may be employed, so that the various imaging, guidewire advancement, septal penetration, and contrast injection or other positioning verification steps need not be detailed herein. Steerable transseptal sheaths can have an elongate outer sheath body extending between a proximal handle to a distal end, with the handle having an actuator for steering a distal segment of the sheath body similar to that described above regarding deployment catheter. A distal electrode and/or marker near the distal end of sheath body can help position the sheath within the left atrium. In some embodiments, an appropriately sized deflectable transseptal sheath without steering capability may be guided into position in the left atrium by transseptal sheath or may be advanced into the left atrium without use of a steerable transseptal sheath. Alternatively, deployment may proceed through a lumen of the steerable sheath. Regardless, in some embodiments an outer access sheath will preferably be positioned so as to provide access to the left atrium LA via a sheath lumen.

Figure 16D:
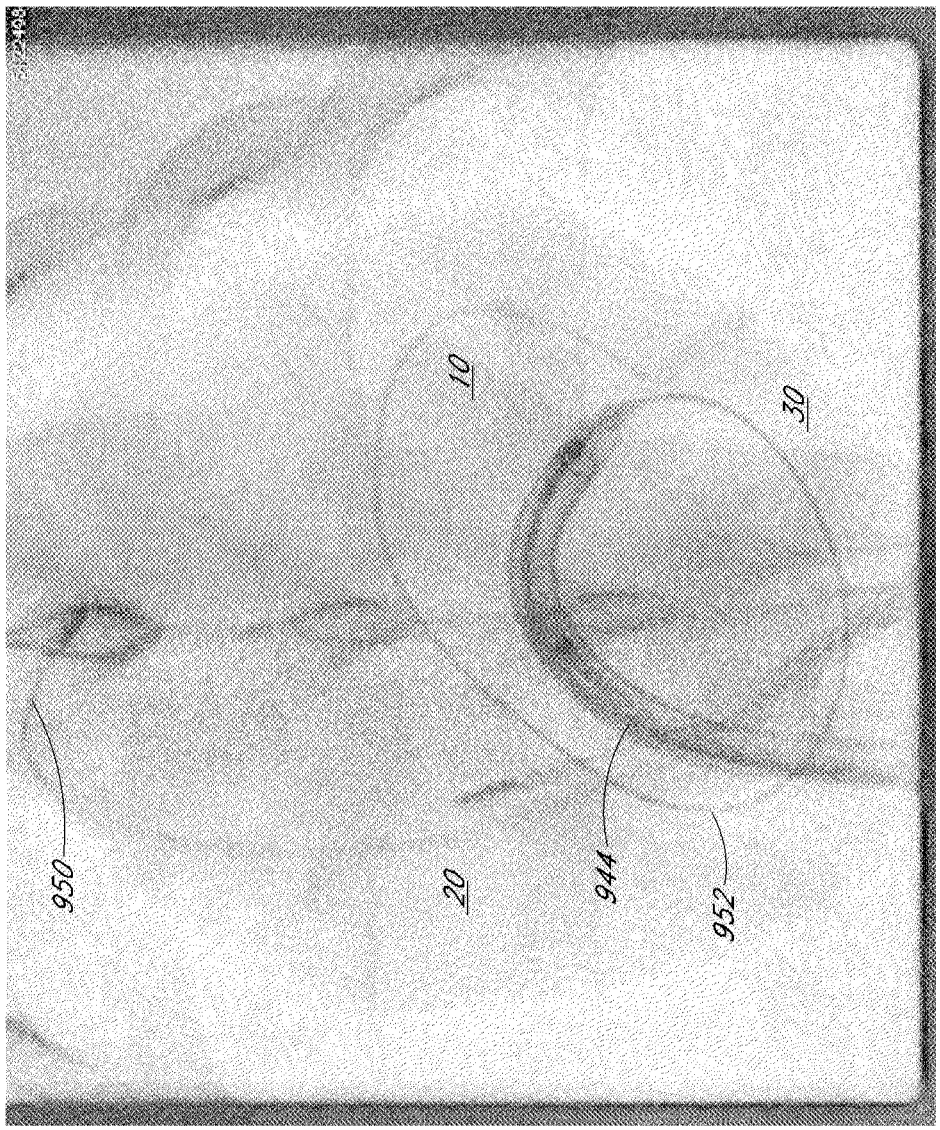
FIG. 16D schematically illustrates a transseptal sheath and delivery system deployed into the left atrium and ventricle of a heart.

Referring now to FIG. 16D, deployment catheter may be advanced through the outer transseptal sheath 944 and into the left atrium 10. The distal end of the deployment catheter 946 moves within the left atrium by manipulating the proximal handle and by articulating the actuator of the handle so as to selectively bend the distal end of the catheter body, bringing the distal end of the catheter into alignment and/or engagement with candidate locations for deployment of an anchor, optionally under guidance of 2D or 3D intracardiac, transthoracic, and/or transesophageal ultrasound imaging, Doppler flow characteristics, fluoroscopic or X-ray imaging, or another imaging modality.

Electrode at the distal end of deployment catheter optionally senses electrogram signals and transmits them to an electrogram system EG so as to help determine if the candidate site is suitable, such as by determining that the electrogram signals include a mix of atrial and ventricular components within a desired range (such as within an acceptable threshold of 1:2). Contrast agent or saline may be introduced through the deployment catheter.

Figure 16E:
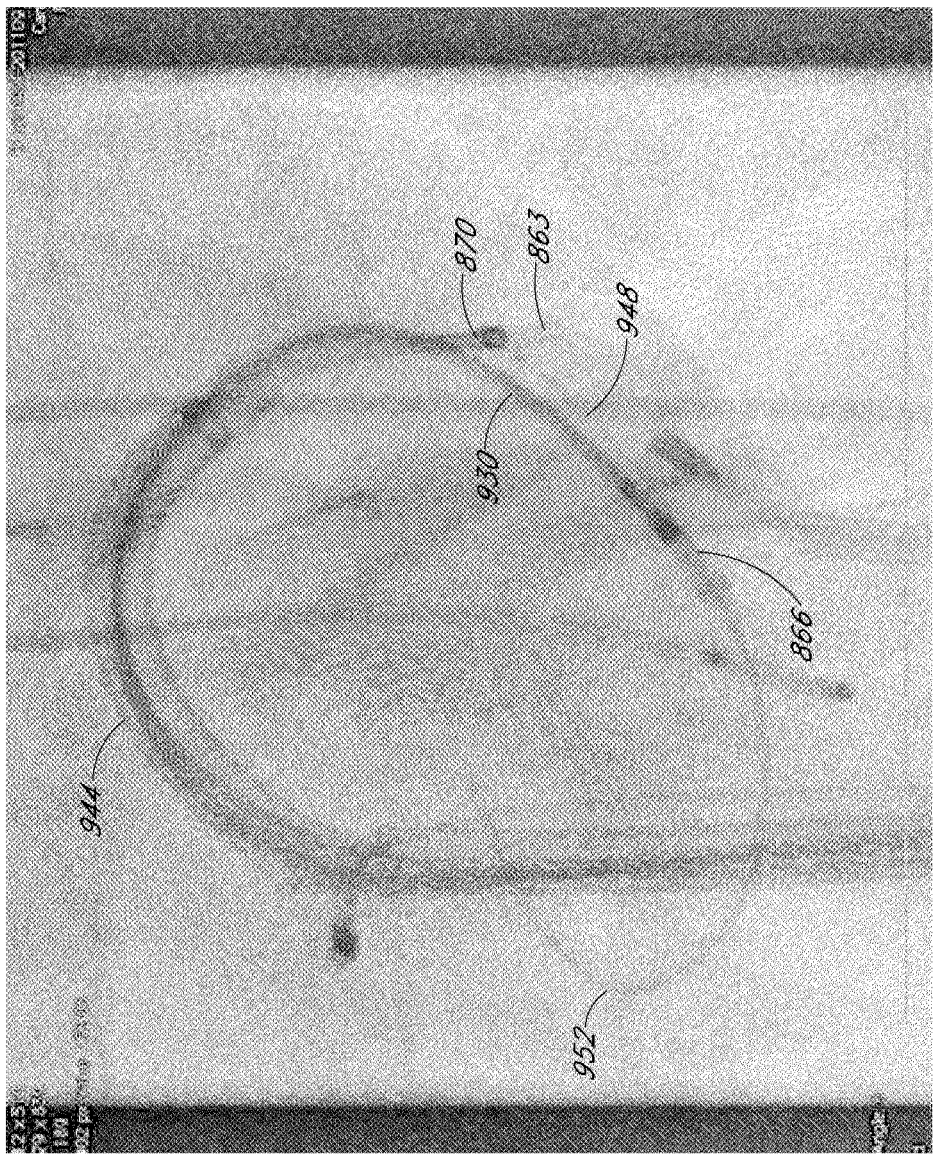
FIG. 16E illustrates the transseptal sheath and delivery system in use during placement of atrial and ventricular anchors of an embodiment of the coaptation element.
Figure 16F:
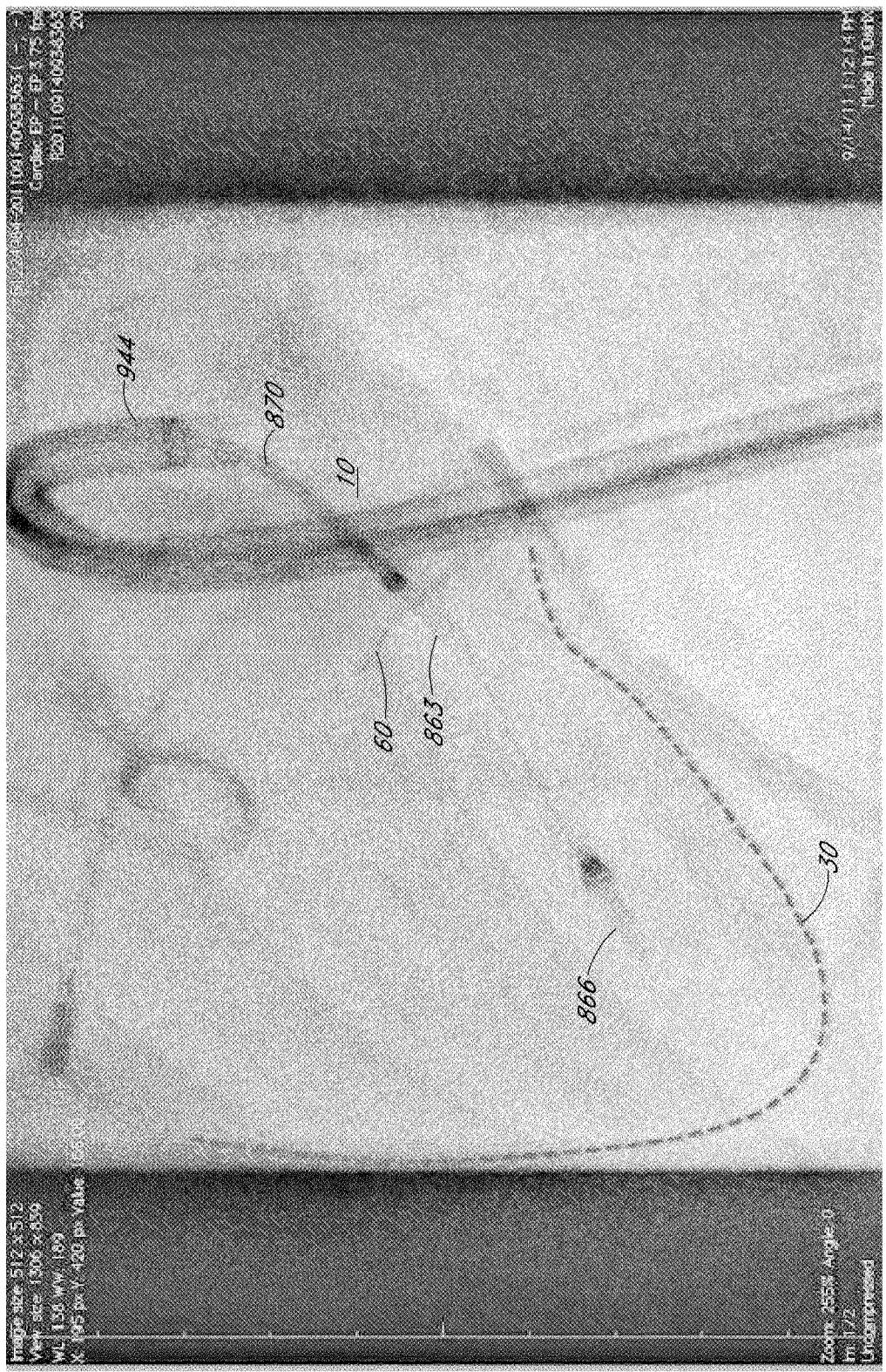
FIG. 16F illustrates an embodiment of the coaptation element in relation to cardiac structures during placement.

As demonstrated in FIG. 16E, a separate intracardiac imaging catheter 950 can be advanced into position in order to provide fluoroscopic dye to facilitate intraoperative imaging to check positioning of the implant. Advancement of the transseptal sheath 944 and/or the delivery catheter can be further controlled by preceding it with a radiopaque guide wire 952, whose position can be confirmed via imaging prior to advancement of the overlying sheath or catheter. Before, during, and/or after the deployment catheter is positioned, engaged with, and/or oriented toward an acceptable target location, an anchor may be advanced distally through a lumen of the deployment catheter, so that the advanced anchor extends from the positioned catheter and into engagement with tissue of the heart at the target location, with advancement of the anchor preferably being performed using an elongate anchor coupling body and an anchor catheter of anchor deployment assembly. An electrocardiogram may be recorded from the anchor via the elongate anchor coupling body to further assist in identifying an acceptable target location.

After the transseptal sheath is placed and delivery catheter advanced through the transseptal lumen, an atrial anchor may be preferably deployed into the mitral valve annulus by axially advancing the anchor and rotating the helical anchor body through the positioned deployment catheter, screwing the helical body penetratingly into the heart tissue using elongate anchor driver 870 and delivery catheter 930. Delivery catheter 930 can then be retracted proximally from deployed anchor 863, leaving the anchor affixed to the tissue and associated elongate anchor driver 870 extending proximally from the anchor and out of the body. Note that anchor 863 may remain only initially deployed at this stage, as it can be recaptured, removed, and/or repositioned by torquing the elongate anchor coupling body so as to unscrew the helical anchor body.

As can be understood with reference to FIG. 16E, delivery catheter can be removed from the outer transseptal sheath 944 leaving anchor driver in place 870 (with the delivery catheter also being withdrawn proximally from over the anchor driver so that the anchor driver may no longer be within the delivery catheter lumen, but remains within the outer transseptal sheath lumen). The delivery catheter 930 can then be re-inserted distally through the outer sheath lumen (alongside the elongate anchor coupling body of the deployed anchor) as needed, in FIG. 16E, the delivery catheter has been reinserted over a second anchor driver coupled to the ventricular anchor 866.

The delivery catheter 930 may be manipulated and/or articulated so as to advance valve body distally out of septal sheath 944 and within the left atrium as so that ventricular anchor 866 and distal portion of valve body cross the mitral valve. Catheter, guidewire, anchor deployment shaft or another torque-transmission shaft may rotationally engage ventricular anchor, and a hub between the ventricular anchor and valve body may allow relative rotation about the helical axis as described above. Tension applied by pulling the proximal ends of anchor drivers while advancing deployment catheter 930 brings the anchors into engagement with the remaining components of the structural interface between valve body and the tissues (such as loops or apertures and atrial member). The position of the annular anchor 863 helps orient valve body within the valve so that edges are each oriented toward an associated commissure, and so that the anterior leaflet coapts with the anterior surface of the coaptation assist element. A desired amount of axial tension can be applied to coaptation assist element by applying a distal load on deployment catheter, and the deployment catheter can be manipulated and/or articulated into engagement with a candidate location of the ventricle, optionally between the papillary muscles. The candidate location can be verified as generally described above, and catheter or another torque-transmitting anchor driving shaft can be rotated while maintaining the distal end of ventricle anchor 866 in contact with the target location so that the helical anchor body penetrates into tissue of the ventricle, thereby deploying the valve body.

In alternative embodiments, an atraumatic ventricular anchor can be deployed by advancing the anchor and/or withdrawing a surrounding sheath from over the anchor) so that the arms of anchor engage with the highly uneven surface of the ventricular trabeculae, and so that the arms of the anchor are entangled therein sufficiently to restrain the position of the anchor within the ventricle. Note that embodiments of such an anchor need not be configured to penetrate significantly into the ventricular wall (although alternative barbed anchor embodiments can).

Advantageously, hemodynamic performance of the valve with the valve body therein can be evaluated before decoupling one or more of the anchors from the delivery catheter system (and in some embodiments, even before the ventricle anchor is deployed in ventricle tissue). If results are less than optimal, one or more of the anchors can be detached from the tissue and retracted back into the transseptal sheath, allowing the physician to reposition the anchor and coaptation assistance body. The valve body can be withdrawn proximally via sheath and an alternative valve body selected, loaded into the sheath, and deployed if appropriate. The atrial and/or ventricular anchors can be redeployed and the surgical staff can again perform a hemodynamic evaluation.

In some embodiments, one or more of guidewire and/or elongate anchor deployment bodies may remain coupled to an associated anchor for hours or even days. Once the implant is in the desired deployed configuration, the device may be locked to the elongate anchor deployment bodies or tethers. Evaluation of placement can be facilitated by radiopaque strut or backbone 948 of the coaptation assist device, which allows evaluation of the position of the implant with relation to the cardiac structures (as seen in FIG. 10F, where the position of the annulus 60 and ventricle are outlined) and of the suspension between anchors. If the deployment is deemed acceptable, after deploying the ventricular anchor and after the implant is released from the catheter system, the surgical staff can remove the remaining catheter system components and anchor drivers.

Figure 16G:
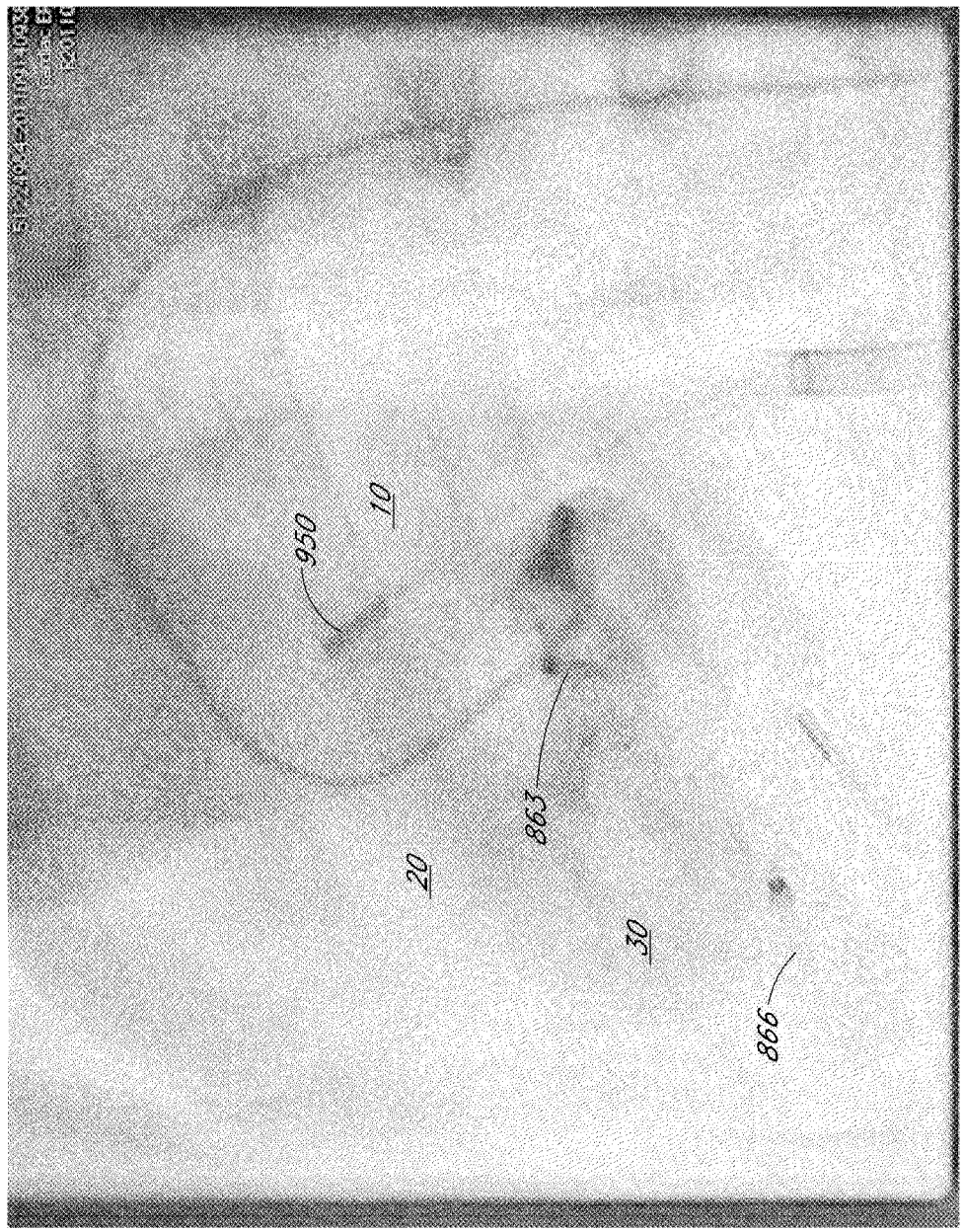
FIG. 16G illustrates evaluation of mitigation of mitral valve regurgitation after final placement of an embodiment of the coaptation element.

A full hemodynamic evaluation; e.g., intra cardiac echocardiogram (ICE), transesophageal echocardiogram (TEE) or transthoracic echocardiogram (TTE) may be performed on the patient after deployment is complete. Similarly, as in FIG. 16G, intracardiac imaging catheter 950 may be retained after the transseptal sheath, anchor drivers, and delivery catheter are removed, permitting angiographic evaluation of blood flow and confirmation that mitral regurgitation has been mitigated.

One of the advantages of some embodiments of the delivery system as contemplated is the ability to easily remove and redeploy one or both anchors during the procedure if intraoperative evaluation shows the initial placement to be suboptimal. Generally, anchor placement will comprise the following steps. First an anchor with attached tether may be coupled to an anchor driver and maneuvered through the delivery catheter and/or the transseptal sheath.

Once the desired intracardiac position is determined, the anchor may be placed while coupled to the anchor driver. The anchor driver may then be uncoupled from the anchor and pulled back, leaving the anchor attached to the cardiac structure and with tether in place. This places the anchor under minimal tension, and the attachment and location are then tested.

If the anchor is in a suboptimal position or the attachment is undesirably tenuous, the driver may be readvanced over the tether and the anchor re-engaged. The anchor may then be withdrawn using the driver and placed at a second site. The driver may again be uncoupled and pulled back and the anchor position tested. If either the first or second position is acceptable, the driver can be completely removed and the tether detached without disrupting the anchor. If a new anchor is needed to replace the first anchor, the original anchor may be withdrawn through the delivery catheter via its attachment to the tether.

Other embodiments are contemplated in which the tether, rather than being removed after verification of anchor placement, may be permanently implanted under the skin, allowing easy removal of the anchor at a later time. The tether can be comprised of any one of a variety of materials, and could be a suture, stainless steel wire, or any other flexible material. The steps disclosed above are intended to be non-limiting examples, not necessarily exact. As will be readily apparent to one skilled in the art, the steps may be performed in a different order, and additional or fewer steps may be performed.

Figure 17A:
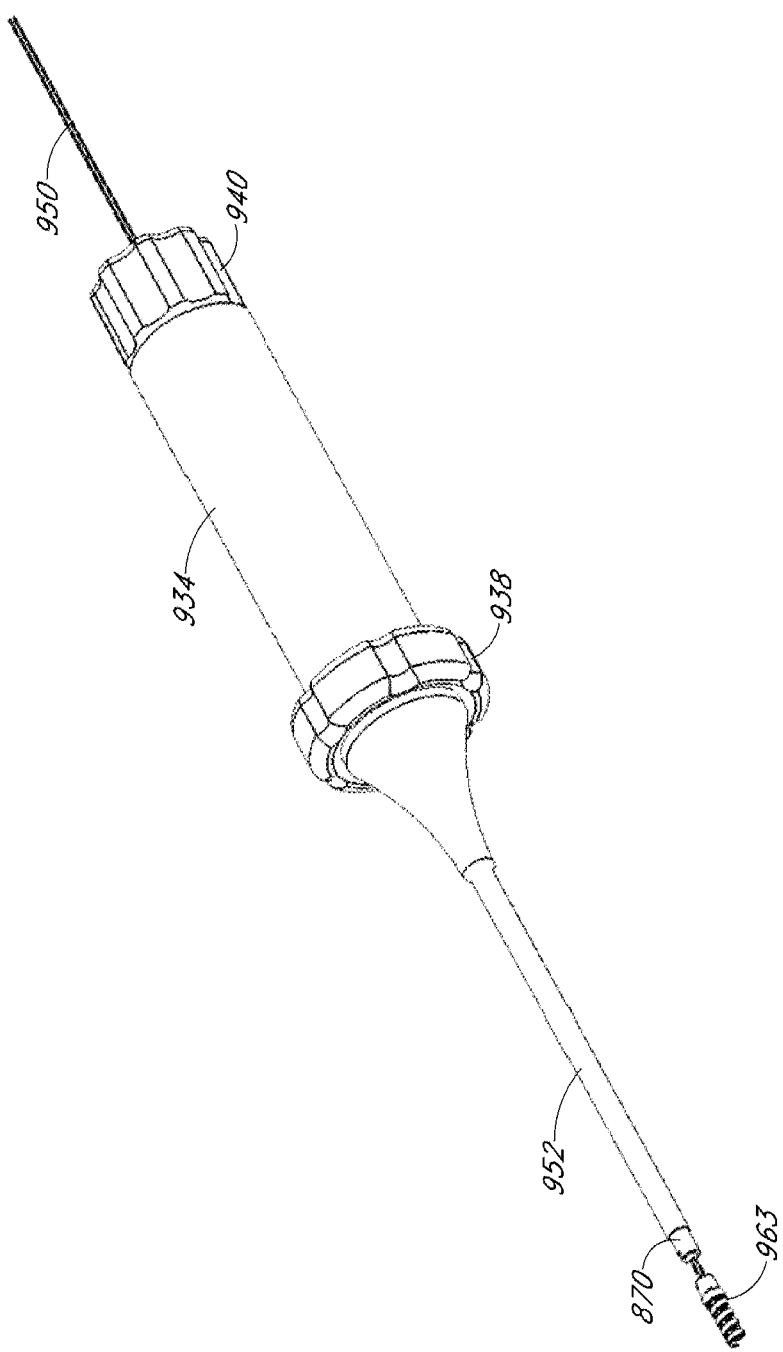
FIG. 17A illustrates an embodiment of an anchor driver with an anchor mounted to a tether element.

Referring now to FIG. 17A-17I, further aspects of the anchor delivery catheter are illustrated. FIG. 17A shows an embodiment of the delivery catheter 866 with a helical anchor 963 disposed toward the distal end of an anchor driver 870. The anchor driver emerges from the lumen of the delivery catheter sleeve 952 which is attached to delivery catheter control handle 934. A tether 950 passes from connection to the anchor, through the sleeve, and out of an inner lumen of the control handle through the proximal end of the control handle. The tether can be manipulated by the surgeon both manually and using the tether control knob 940. Delivery catheter sleeve 952 can be manipulated using the sleeve control knob 938 located in this embodiment at the distal aspect of the control handle.

Figure 17B:
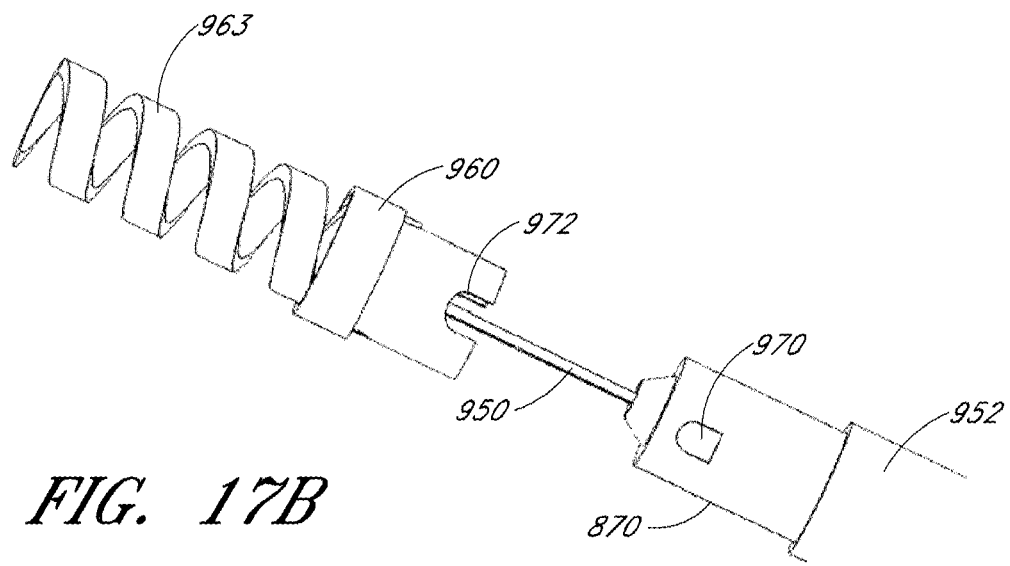
FIG. 17B schematically illustrates the tip of an anchor driver with an anchor mounted to the driver.
Figure 17C:
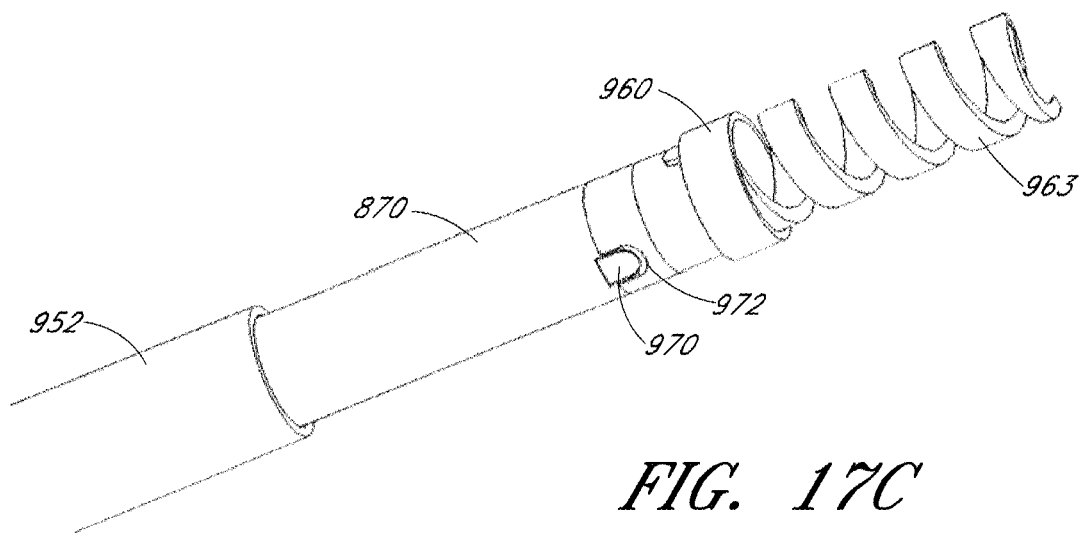
FIG. 17C illustrates the tip of an anchor driver with anchor released from the driver.

FIGS. 17B and 17C illustrate the distal end of the anchor driver 870 and delivery catheter 952 uncoupled (FIG. 17B) and coupled (FIG. 17C) to a helical anchor 963. In FIG. 17B, the driver and catheter have been partially retracted from the anchor, and the tether 950 can be seen maintaining control of the anchor. The anchor in FIGS. 17B-I has a sleeve lock ring 960 which, in the coupled position, retains the sleeve of the catheter. Also visible are the key 970 on the distal portion of the driver which may be configured to fit within the key hole 972 of the proximal, coupling portion of the anchor. This prevents rotational slippage between the driver and the anchor and permits the anchor to be screwed into the cardiac structure via driver rotation.

Figure 17D:
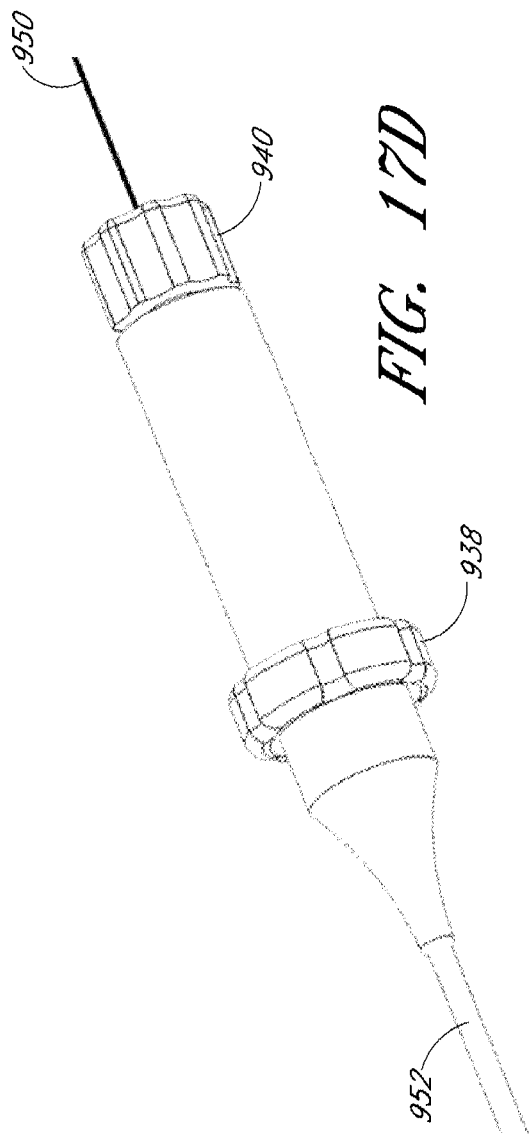
FIG. 17D schematically illustrates the proximal portion of an anchor delivery system in the anchor release position.
Figure 17E:
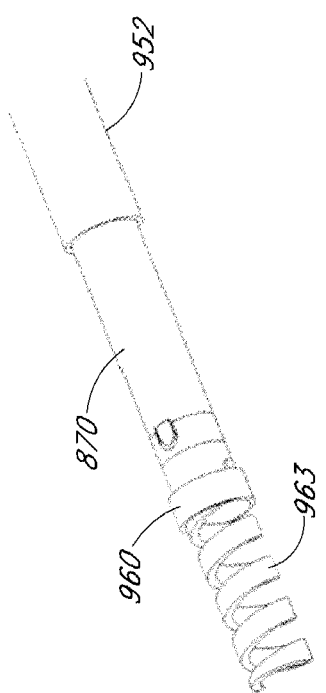
FIG. 17E schematically illustrates the distal portion of an anchor delivery system in the anchor release position FIG. 17F schematically illustrates the proximal portion of an anchor delivery system in the anchor locking position.

FIGS. 17D and 17E illustrate the unlocked position of the anchor, with sleeve 952 retracted from the proximal attachment area of the anchor and the sleeve lock ring 960. The sleeve control knob 938 is illustrated in the retracted position, proximal to its position during sleeve/anchor engagement, which retracts the sleeve proximally, releasing the anchor. The tether control knob 940 is also seen. Rotation of the tether control knob can lock the tether in position relative to the handle or unlock it relative to the handle, permitting tension to be placed on the anchor or removal of the tether from the anchor.

Figure 17F:
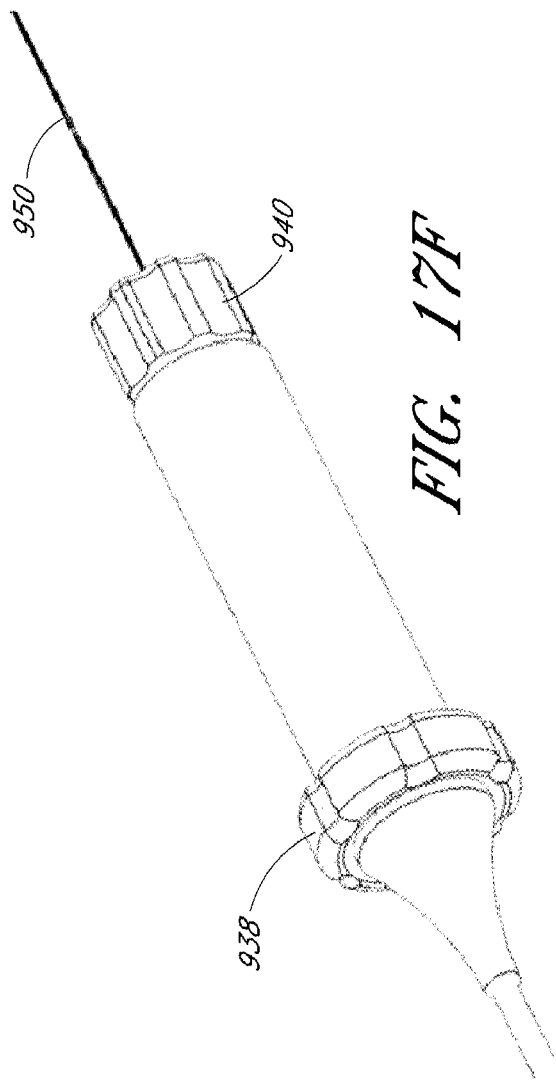
FIG. 17G schematically illustrates the distal portion of an anchor delivery system in the anchor locking position.
FIGS. 17H-I schematically illustrate an embodiment of an anchor delivery system, with the anchor deployed from the driver for testing, but still attached to the tether.
FIG. 17J schematically illustrates the distal end of an anchor driver, with anchor released from the driver for testing.
Figure 17G:
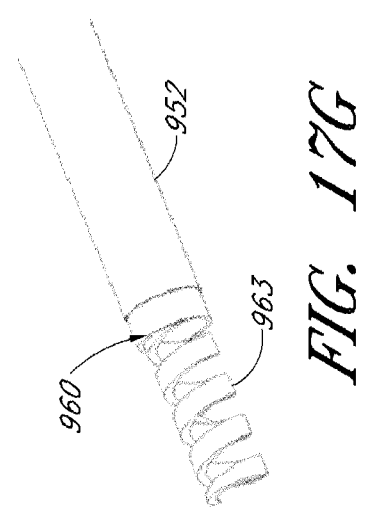
Figure 17H:
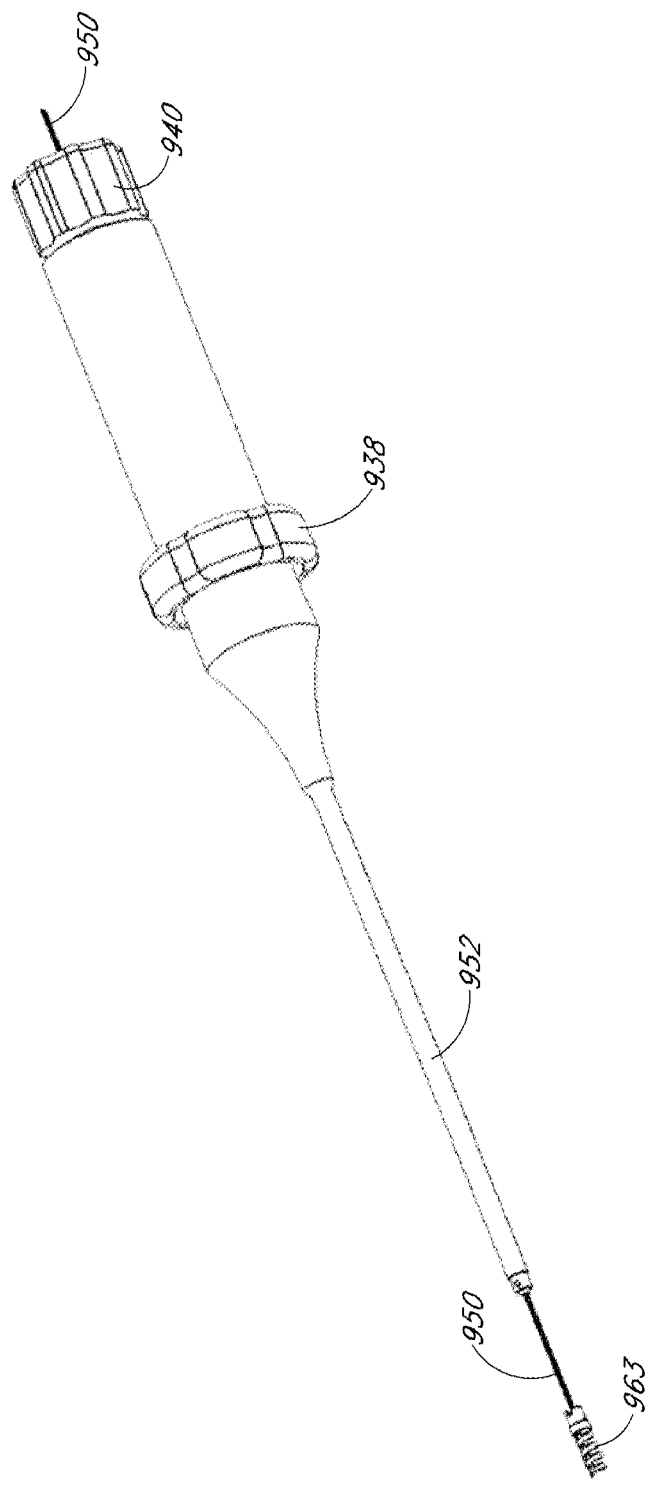
Figure 17I:
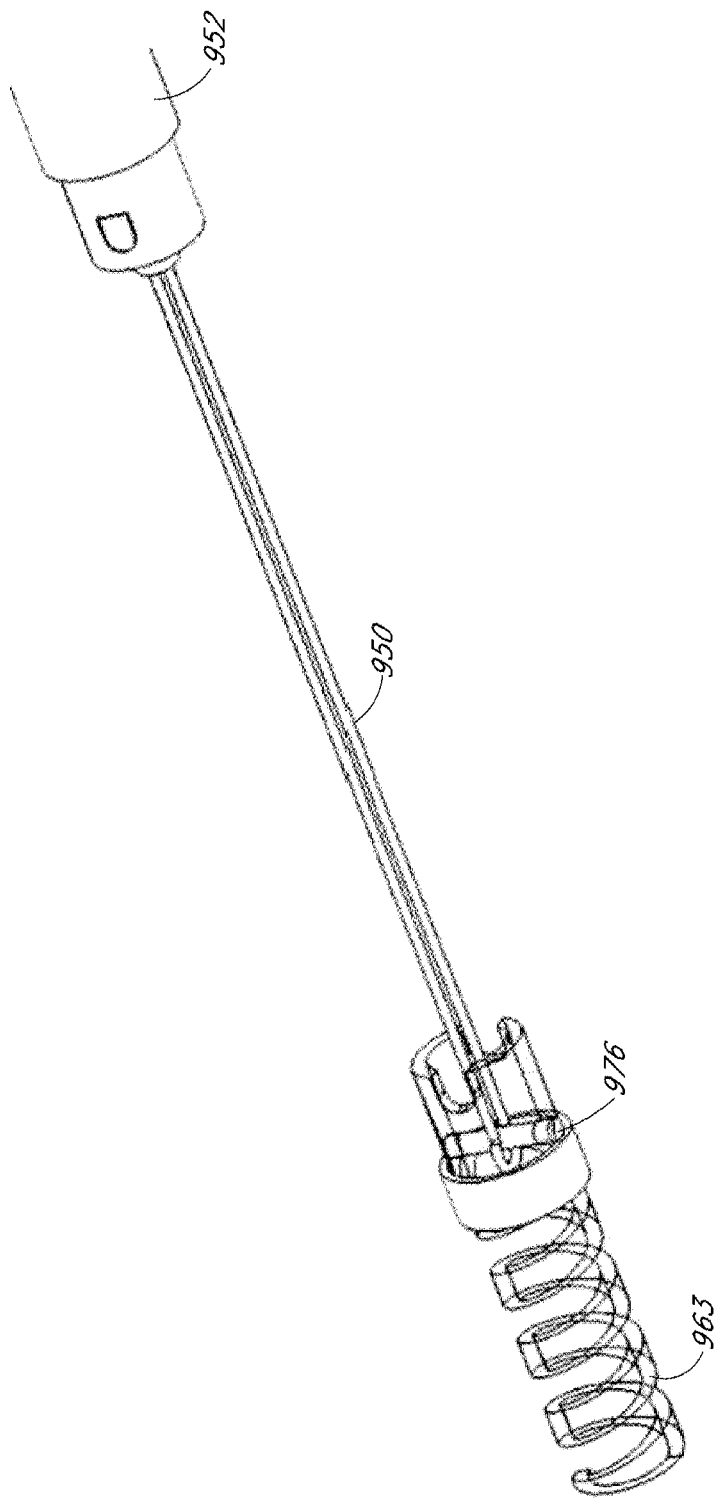
Figure 17J:
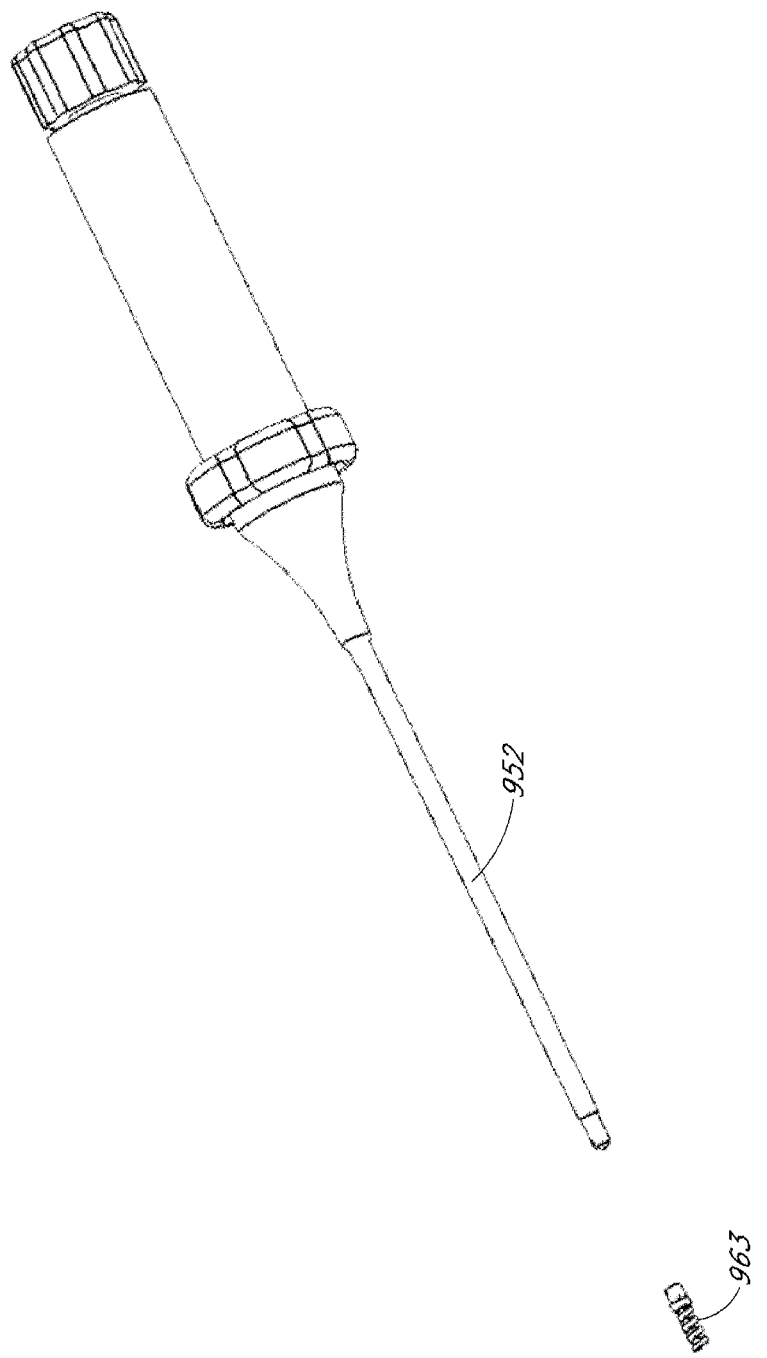

FIGS. 17F and 17G illustrate the locked position of the anchor, with sleeve 952 advanced onto the sleeve lock ring 960. The sleeve control knob 938 may be advanced distally to lock the anchor to the catheter. FIG. 17H illustrates the anchor uncoupled from the driver and the driver partially withdrawn to evaluate the function of the anchor. First, the tether control knob 940 may be unlocked to release the tether from the catheter, then the sleeve control knob 938 may be retracted to release the anchor from the catheter. Catheter may be withdrawn over the tether, exposing the tether distally, still coupled to the anchor. Manipulation of the tether may then be performed to test the fixation and imaging can be done to test the position of the anchor prior to removal of the tether from the anchor. Tether cross pin 976 is shown in FIG. 17I, allowing the tether to be easily attached to the anchor by threading a suture around the cross pin. Manipulation may be accomplished by exerting tension on both ends of the tether proximally. Removal of the tether may be easily accomplished by exerting tension on one end of the tether proximally. FIG. 17J illustrates the anchor 963 entirely removed from the tether and delivery catheter assembly after confirming optimal engagement and placement with respect to the cardiac tissue.

Figure 18A:
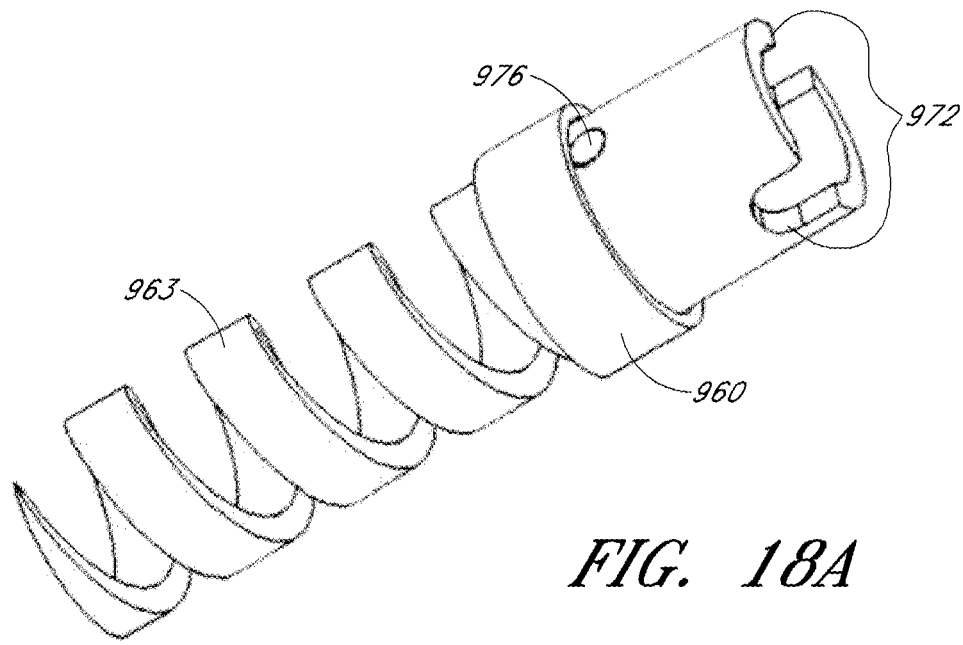
FIG. 18A schematically illustrates an embodiment of a helical anchor with coupling mechanism alone.
Figure 18B:
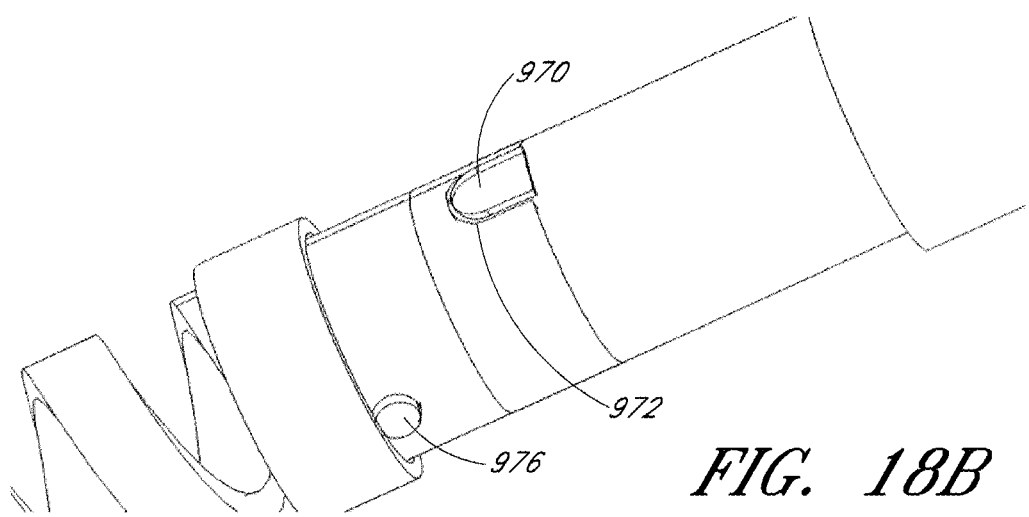
FIG. 18B schematically illustrates an embodiment of a helical anchor coupled to a driver.
Figure 18C:
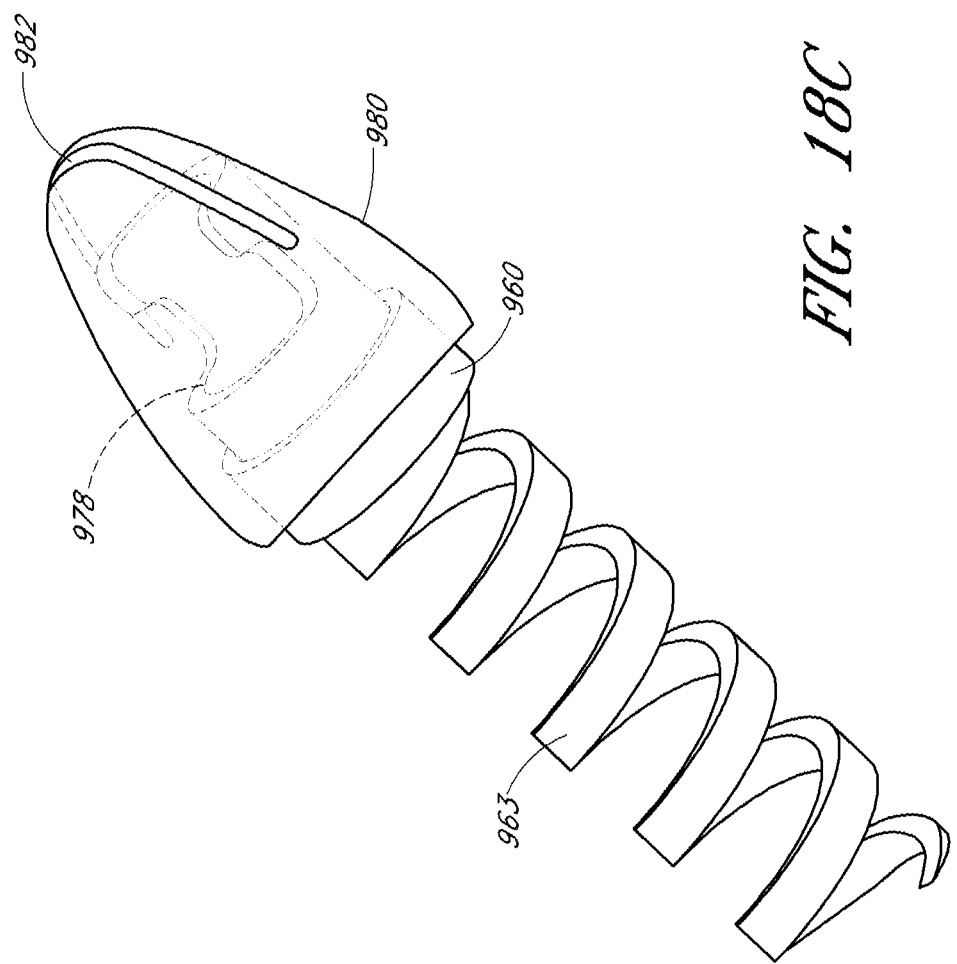

FIGS. 18A and 18B illustrate an embodiment of the anchor, further showing the key holes 872, tether cross pin 976, and sleeve lock ring 960 which engage with the driver and catheter system. In FIG. 18B, the key 970 of the driver shaft is illustrated engaged in the key hold of the anchor to allow rotation in clockwise and counter clockwise directions for placement and removal of the anchor from tissue. FIG. 18C illustrates an alternate embodiment of the anchor with a protective boot or gasket 980 which fits over the proximal aspect of the anchor. The boot or gasket has a slit or other opening 982 in its proximal aspect which permits passage of a driver during insertion of the anchor, but, upon retraction of the driver, seals over to protect tissues from the roughness of the proximal end of the anchor and enhance healing. The boot would be bonded to the proximal end of the helical anchor 963 or to the stop ring 960. An alternate coupling feature 978 for connecting an anchor to a driver is also shown, though many other variations are possible. The protective boot may be comprised of any one of a number of suitable materials, including but not limited to silicone, ePTFE, Dacron, pericardium, or other biologics.

While some embodiments have been described in some detail for clarity of understanding, a variety of adaptations and modification will be clear to those of skill in the art. For example, access to the left atrium can be provided at least in part via a minimally invasive entry in the left atrial appendage or pulmonary vein, or through the left ventricular apex. Additionally, as the devices and methods described herein may be faster, less skill dependent, and/or suitable for sicker patients than alternative valve treatments (that often involve larger access systems or are otherwise more traumatic), and as the implants described herein may be temporarily deployed, these techniques may be used as a short or intermediate-term therapy, giving patients time and allowing recovery so as to be better able to tolerate an alternative treatment. These techniques may also be suitable for re-treatment of patients that have previously had valve therapies. These techniques may also be appropriate for placement in positions at the mitral valve in a patient undergoing coronary artery bypass grafting or other cardiac surgery, such as aortic valve replacement.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. For example, while the features and embodiments shown herein have been described in the context of applications specific to the treatment of mitral valve insufficiency, the various features described can be used individually, or in combination, to produce valve assist for use in multiple and varied cardiac and vascular applications. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially. Hence, the scope of the present invention is limited solely by the claims.

What is claimed is:

1. A coaptation implant system comprising:
   a coaptation implant comprising:
      a coaptation surface and a leaflet surface;
      a superior edge, lateral edges, and an inferior edge, wherein a distance between the lateral edges generally decreases toward the inferior edge;
      a hub; and
      at least one strut, wherein a strut of the at least one strut extends from the hub toward the inferior edge; and
   a helical anchor configured to be rotated relative to the hub to engage tissue, wherein the coaptation implant is configured to be suspended across a valve plane of a valve from an atrium proximally and toward a ventricle distally, wherein the coaptation implant is configured to be suspended such that the coaptation surface coapts with a first leaflet and the leaflet surface overlies a second leaflet.

2. The coaptation implant system of claim 1, wherein the coaptation implant is configured to attach superiorly to a posterior aspect of an annulus.

3. The coaptation implant system of claim 1, wherein the hub is cylindrical.

4. The coaptation implant system of claim 1, wherein the hub is spaced inward from the superior edge.

5. The coaptation implant system of claim 1, wherein more than one anchor is configured to attach the coaptation implant to tissue.

6. The coaptation implant system of claim 1, wherein during diastole, the coaptation implant is configured to stay in substantially the same position while movement of the first leaflet opens the valve.

7. The coaptation implant system of claim 1, wherein during systole, a surface of the coaptation implant is configured to stretch away from the helical anchor while the helical anchor remains unmoved.

8. A coaptation implant system comprising:
   a coaptation implant comprising:
      a coaptation surface and a leaflet surface;
      a superior edge, lateral edges, and an inferior edge, wherein a distance between the lateral edges generally decreases toward the inferior edge;
      a hub configured to be located near a mitral valve annulus; and
      a strut extending from the hub toward the inferior edge; and
   a helical anchor configured to be rotated relative to the hub; and
   a driver configured to rotate the helical anchor, wherein the driver is configured to engage to the helical anchor extra-corporeally, the helical anchor is configured to engage to the hub extra-corporeally, wherein the driver is configured to be withdrawn into a catheter for delivery with the coaptation implant collapsed for delivery.

9. The coaptation implant system of claim 8, further comprising a secondary driver for engaging a secondary anchor.

10. The coaptation implant system of claim 9, wherein the driver and the secondary driver are configured to be separately manipulated.

11. The coaptation implant system of claim 8, wherein the coaptation implant is configured to cover a posterior leaflet so the coaptation implant coapts with an anterior leaflet during systole and maintains a valve seal.

12. The coaptation implant system of claim 8, wherein the hub is configured to extend toward the left atrium when the coaptation implant is positioned on the mitral valve annulus.

13. A coaptation implant system comprising:
   a coaptation implant comprising:
      a coaptation surface and a leaflet surface;
      a superior edge, lateral edges, and an inferior edge, wherein a distance between the lateral edges generally decreases toward the inferior edge;
      a central hub;
      a first anchoring location laterally spaced from the central hub; and
      a strut extending from the hub toward the inferior edge;
   a central anchor configured to be rotated relative to the central hub to engage an annulus of a heart valve; and
   a first anchor configured to be rotated relative to the first anchoring location to engage a first lateral commissure of the heart valve.

14. The coaptation implant system of claim 13, further comprising a second anchoring location laterally spaced from the central hub and a second anchor configured to be rotated relative to the second anchoring location to engage a second lateral commissure of the heart valve.

15. The coaptation implant system of claim 14, wherein the first anchoring location and the second anchoring location define a diameter which corresponds to the distance between the first and second lateral commissures, wherein the distance is between 35 mm and 45 mm.

16. The coaptation implant system of claim 13, wherein the first anchor and the second anchor are configured to maintain the shape and position of the coaptation implant once deployed.

17. The coaptation implant system of claim 13, wherein the coaptation implant is configured to cover a posterior leaflet.

18. The coaptation implant system of claim 13, wherein the central anchor comprises a helical anchor.

* * * * *